United States Patent
Nadji et al.

(10) Patent No.: US 9,255,119 B2
(45) Date of Patent: *Feb. 9, 2016

(54) PROCESS FOR PERPARING FONDAPARINUX SODIUM AND INTERMEDIATES USEFUL IN THE SYNTHESIS THEREOF

(71) Applicant: Reliable Biopharmaceutical Corporation, St. Louis, MO (US)

(72) Inventors: Sourena Nadji, Olivette, MO (US);
James T. Smoot, Mt. Zion, IL (US);
Joseph A. Vanartsdalen, Saint Charles, MO (US)

(73) Assignee: RELIABLE BIOPHARMACEUTICAL CORPORATION, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/256,235

(22) Filed: Apr. 18, 2014

(65) Prior Publication Data

US 2015/0018537 A1  Jan. 15, 2015

Related U.S. Application Data

(63) Continuation of application No. 13/618,786, filed on Sep. 14, 2012, now Pat. No. 8,703,923, which is a continuation of application No. 12/847,719, filed on Jul. 30, 2010, now Pat. No. 8,288,515.

(60) Provisional application No. 61/230,557, filed on Jul. 31, 2009.

(51) Int. Cl.

| C07H 15/00 | (2006.01) |
|---|---|
| C07G 3/00 | (2006.01) |
| C07H 17/00 | (2006.01) |
| C07H 1/00 | (2006.01) |
| C07H 5/08 | (2006.01) |
| C07H 5/10 | (2006.01) |
| C07H 5/04 | (2006.01) |
| A61K 31/737 | (2006.01) |
| C07H 13/04 | (2006.01) |
| C08B 37/00 | (2006.01) |
| C07H 5/06 | (2006.01) |
| C07H 19/01 | (2006.01) |

(52) U.S. Cl.
CPC ............... *C07H 1/00* (2013.01); *A61K 31/737* (2013.01); *C07H 5/04* (2013.01); *C07H 5/06* (2013.01); *C07H 5/08* (2013.01); *C07H 5/10* (2013.01); *C07H 13/04* (2013.01); *C07H 19/01* (2013.01); *C08B 37/0063* (2013.01)

(58) Field of Classification Search
None
See application file for complete search history.

(56) References Cited

U.S. PATENT DOCUMENTS

| 4,401,662 A | 8/1983 | Lormeau et al. |
|---|---|---|
| 4,607,025 A | 8/1986 | Petitou et al. |
| 4,774,231 A | 9/1988 | Petitou et al. |
| 4,801,583 A | 1/1989 | Petitou et al. |
| 4,818,816 A | 4/1989 | Petitou et al. |
| 4,841,041 A | 6/1989 | van Boeckel et al. |
| 4,987,223 A | 1/1991 | Choay et al. |
| 5,378,829 A | 1/1995 | Petitou et al. |
| 5,514,659 A | 5/1996 | Petitou et al. |
| 5,529,985 A | 6/1996 | Petitou et al. |
| 5,543,403 A | 8/1996 | Petitou et al. |
| 5,773,605 A | 6/1998 | Petitou et al. |
| 6,174,863 B1 | 1/2001 | van Boeckel et al. |
| 6,271,215 B1 | 8/2001 | Parish et al. |
| 6,462,183 B1 | 10/2002 | Toth et al. |
| 6,528,497 B1 | 3/2003 | Basten et al. |
| 6,534,481 B1 | 3/2003 | Driguez et al. |
| 6,670,338 B1 | 12/2003 | Petitou |
| 6,765,089 B1 | 7/2004 | Toth et al. |
| 6,846,917 B2 | 1/2005 | Seeberger et al. |
| 6,953,850 B1 | 10/2005 | Dekany et al. |
| 7,468,358 B2 | 12/2008 | Kennedy et al. |
| 7,541,445 B2 | 6/2009 | Seifert et al. |
| 7,582,737 B2 | 9/2009 | Hung et al. |
| 2005/0020536 A1 | 1/2005 | Branellec et al. |
| 2006/0079483 A1 | 4/2006 | Hung et al. |
| 2006/0167237 A1 | 7/2006 | West et al. |

FOREIGN PATENT DOCUMENTS

| JP | 63218691 A | 9/1988 |
|---|---|---|
| JP | 6094989 A | 4/1994 |

OTHER PUBLICATIONS

Synthesis from cellobiose, of a trisaccharide closely related to the GlcNAc->GlcA->GlcN segment of the anti-thrombin-binding sequence of heparin, Ichikawa et al., Carbohydrate Research, 141 (1985), 273-282.

Synthesis of heparin pentasaccharide fragment with a high affinity for antithrombin III employing cellobiose as a key starting material, Ichikawa et al., Tetrahedron Letters, vol. 27, No. 5, pp. 611-614 (1986).

(Continued)

*Primary Examiner* — Patrick Lewis
(74) *Attorney, Agent, or Firm* — Blank Rome LLP

(57) ABSTRACT

Processes for the synthesis of the Factor Xa anticoagulent Fondaparinux, and related compounds are described. Also described are protected pentasaccharide intermediates as well as efficient and scalable processes for the industrial scale production of Fondaparinux sodium by conversion of the protected pentasaccharide intermediates via a sequence of deprotection and sulfonation reactions.

3 Claims, 11 Drawing Sheets

(56) References Cited

OTHER PUBLICATIONS

Adinofli, et al., Activation of Disarmed 2-O-alkoxycarbonylated Glycosyl Trichloroacetimidates with Lanthanide Triflates: an Efficient Approach for the Synthesis of 1,2-trans Glycosides, Tetrahedron Letters 42 (2001) 5967-5969.

Adinofli, et al., Efficient Activation of Armed Glycosyl Trichloroacetimidates with Sm(Otf)3 in the Stereoselective Glycosidation of Saccharide Acceptors, Tetrahedron Letters 41 (2000) 9005-9008.

Allanson, et al., Synthesis of Phenyl 1-Thioglycopyranosiduronic Acids Using a Sonicated Jones Oxidation, Tetrahedrom Letters 39 (1998) 1889-1892.

Arndt, et al., Use of Cerny Epoxides for the Accelerated Synthesis of Glycosamingolycans; Organic Letters, 2003, vol. 5, No. 22, pp. 4179-4182.

Atha, et al., Contribution of 3-O- and 6-O-Sulfated Glucoasmine Residues in the Heparin-Induced Conformational Change in Antithrombin III, Biochemistry 1987, 26, 6454-6461.

Bongat, et al., Recent Trends in the Synthesis of O-glycosides of 2-amino-2-deoxysugars, Carbohydrate Research 342 (2007) 374-406.

Casu, et al., The Structure of Heparin Oligosaccharide Fragments with High Anit-(factor Xa) Activity Containing the Minimal Antithrombin III-binding Sequence, Biochem. J. (1981) 197, 599-609.

Chiba, et al., Chemical Synthesis of L-Iduronic Acid-containing Di-saccharide Fragments of Heparin, Carbohydrate Research, 174 (1988) 253-264.

Code, et al., A Modular Strategy Toward the Synthesis of Heparin-like Oligosaccharides Using Monomeric Building Blocks in a Sequential Glycosylation Strategy, J. Am. Chem. Soc., 2005, 127 (11), 3767-3773.

Das, et al., Synthesis of Conformationally Locked L-Iduronic Acid Derivatives: Direct Evidence for a Critical Role of the Skew-Boat 2S0 Conformer in the Activiation of Antithrombin by Heparin, Chem. Eur. J. 2001, 7, No. 22, pp. 4821-4834.

Duchaussoy, et al., The First Total Synthesis of the Antithrombin III Binding Site of Porcine Mucosa Heparin, Bioorganic & Medicinal Chemistry Letters, vol. 1, No. 2, pp. 99-102, 1991.

Ernst, et al., Haloenamines- II. A Rapid and Efficient Synthesis of Carbohydrate 1,2- Orthoesters, Tetrahedron Letters, vol. 31, No. 43, pp. 6167-6170, 1990.

Ganguli, et al., a-β Selectivity in the Synthesis of 3-substituted, 4-methyl Umbelliferone Glycosides of N-acetyl Glucoasmine and Chitobiose, Tetrahedron Asymmetry 16 (2005) 411-424.

Grundler, et al., Anwendung des Trichloroacetimidate-Verfahrens auf 2-Azidoglucose- und 2-Azidogalactose-Derivative, Liebigs Ann. Chem. 1984, 1826-1847.

Hadd, et al., Glycosyl iodides are Highly Efficient Donors Under Neutral Conditions, Carbohydrate Research 320 (1999) 61-69.

Hawley, et al., Investigation of the Hydrogen Bonding Properties of a Series of Monosaccharides in Aqueous Media by 1H NMR and IR Spectroscopy, Eur. J. Org. Chem., 2002, 1925-1936.

Hernandez, et al., General Stereoselective Synthesis of Chemically Differentiated α-Diamino Acids: Synthesis of 2,6-Disaminopimelic and 2,7-Diaminosuberic Acids, J. Org. Chem. 2001, 66, 4934-4938.

Hori, et al., Regioselective de-O-benzylation with Lewis Acids, J. Org. Chem., 1989, 54(6), 1346-1353.

Ichikawa, et al., Synthesis of a Heparin Pentasaccharide Fragment with a High Affinity for Antitrombin III Employing Cellobiose as a Key Starting Material, Tetrahedron Letters, vol. 27, No. 5, pp. 611-614, 1986.

Ichikawa, et al., Synthesis of Methyl Glycoside Derivatives of Tri- and Penta-saccharides related to the Antithrombin III-binding sequence of Heparin, Employing Cellobiose as a Key Starting-Material, Carbohydrate Research, 172 (1988) 37-64.

Ichikawa, et al., Synthesis, From Cellobiose, of a Trisaccharide Closely Related to the GlcNAc'GlcA'GlcN Segment of the Antithrombin-binding Sequence of Heparin, Carbohydrate Research, 141 (1985) 273-282.

Jiang, et al., Copper(II)-Catalyzed Aerobic Oxidation or Primary Alcohols to Aldehydes in Ionic Liquid [bmpy]PF6, Organic Letters, 2005, vol. 7, No. 17, 3689-3692.

Karst, et al., Stereocontrolled Total Synthesis of Shark Cartilage Chondroitin Sulfate D-Related Tetra- and Hexasaccharide Methyl Glycosides, Eur. J. Org. Chem. 2002, 815-825.

Karst, et al., Sulfo-Protected Hexosamine Monosaccharides: Potentially Versatile Building Blocks for Glycosaminoglycan Synthesis, Organic Letters, 2003, vol. 5, No. 25, 4839-4842.

Ke, et al., Development of Specific Inhibitors for Heparin-binding Proteins Based on the Cobra Cardiotoxin Structure: an Effective Synthetic Strategy for Rationally Modified Heparin-like Disaccharides and a Trisaccharide, Carbohydate Research 340 (2005) 355-372.

Ke, et al., A Short Route to L-iduronic Acid Building Blocks for the Synthesis of Heparin-like Disaccharides, Tetrahedron Letters 44 (2003) 7767-7770.

Kim, et al., Selective Benzoylation of Diols with 1-(Benzoyloxy)benzotriazole, J. Org. Chem. 1985, 50, 1751-1752.

Koshida, et al., Synthesis and Biological Activity of Oligomer-model Compounds Containing Units of a Key Platelet-binding disaccharide of Heparin, Tetrahedrom Letters 40 (1999) 5725-5728.

Kovensky, et al., Binding of Heparan Sulfate to Fibroblast Growth Factor-2 Total Synthesis of a Putative Pentasaccharide Binding Site, Tetrahedron: Asymmetry, vol. 7, No. 11, pp. 3119-3128, 1996.

Kovesnky, et al., a Synthetic Heparan Sulfate Pentasaccharide, Exclusively Containing L-Iduronic Acid, Displays Higher Affinity for FGF-2 than its D-Glucuronic Acid-containing Isomers, Bioorganic & Medicinal Chemistry 7 (1999) 1567-1580.

La Ferla, et al., Synthesis of Disacchahride Sub-Units of a New Series of Heparin Related Oligosaccharides, Tetrahedron 55 (1999) 9867-9880.

Lee, et al., Synthesis of Heparin Oligosaccharides, J. Am. Chem. Soc. 2004, 126, 476-477.

Lei, et al., Synthesis of a 3-Deoxy-L-iduronic Acid Containing Heparin Pentasaccharide to Probe the Conformation of the Antithrombin III Binding Sequence, Bioorganic & Medicinal Chemistry 6 (1998) 1337-1346.

Leteux, et al., an electroophile-mediated Cyclization on the 1,6-anhydro-D-Glucopyranose Framework, Carbohydate Research, 242 (1993) 119-130.

Litjens, et al., The Use of Cyclic Bifunctional Protecting Groups in Oligosaccharide Synthesis—an Overview, Carbohydrate Research, available online at www.sicencedirect.com.

Lohman, et al., A Stereochemical Surprise at the Late Stage of the Synthesis of Fully N-Differentiated Heparin Oligosaccharides Containing Amino, Acetamido, and N-Sulfonate Groups, J. Org. Chem., 2004, 69 (12) 4081-4093.

Lohman, et al., One-pot Conversion of Glycals to cis-1,2-lsopropylidene-α-glycosides, J. Org. Chem. 2003, 68, 7541-7543.

Lohman, et al., Synthesis of Iduronic Acid Building Blocks for the Modular Assembly of Glycosaminoglycans, J. Org. Chem. 2003, 68, 7559-7561.

Lu, et al., Synthesis of 48 Disaccharide Building Blocks for the Assembly of Heparin and Heparan Sulfate Oligosaccharide Library, Organic Letters, 2006, vol. 8, No. 26, 5995-5998.

Lubineau, et al., New Accesses to L-iduronyl Synthons, Tetrahedrom Letters 41 (2000) 307- 311.

Luo, et al., Synthesis of D-ribo-C18-phytosphingosine from D-glucosamine via the D-allosamine Derivatives as Key Intermediates, Tetrahedron Letters 43 (2002) 4889-4892.

Manabe, et al., N-Benzyl-2,3-oxazolidinon as a Glycosyl Donor for Selective α-Glycosylation and One-Pot Oligosaccharide Synthesis Involving 1,2-cis-Glycosylation, J. Am. Chem. Soc. 2006, 128, 10666-10667.

Ohashi, et al., Use of Polysytrene-Supported DBU in the Synthesis and ?-Selective Glycosylation Study of the Unstable Schmidt Donor of L-Kedaresamine, Organic Letters, 2004, vol. 6, No. 5, 719-722.

(56) References Cited

OTHER PUBLICATIONS

Orgueira, et al., Conformational Locking of the Glycosyl Acceptor for Stereocontrol in the Key Step in the Synthesis of Heparin, Angew. Chem. Int. Ed. 2002, 41, No. 12, pp. 2128-2131.

Orgueira, et al., Modular Synthesis of Heparin Oligosaccharides, Chem. Eur. J. 2003, 9, No. 1, pp. 140-169.

Paulsen, et al., Stereoselektive Synthese ?-glycosidisch verknupfter Di- and Oligosaccharide der 2-amino-2-desoxy-D-glucopyranose, H. Paulsen and W. Stenzel, Chem. Ber. 111, 2334-2347 (1978).

Petitou, et al., A Unique Trisaccharide Sequence in Heparin Mediates the Early Step of Antithrombin III Activation, Glycobiology vol. 7, No. 3, pp. 323-327, 1997.

Petitou, et al., Conformational Flexibility: A New Concept for Explaining Binding and Biological Properties of Iduronic Acid-Containing Glycosaminoglycans, © 1988, Elsevier Publications Cambridge, TIBS13, Jun. 1988, pp. 221-225.

Petitou, et al., Synthesis of Heparin Fragments, a Chemical Synthesis of the Pentasaccharide O-(2-Deoxy-2-Sulfamido-6-O-Sulfo-α-D-Glucopyranosyl)-1à4)-O-(2-Deoxy-2-sulfamido-3,6-di-o-sulfo-α-D-glucopyranosyl)-(1à4)-O-(2-O-sulfo-α-L-idopyranosyluronic acid)-(1à4)-2-deoxy-2-sulfamido-6-o-sulfo-D-glucopyranose decasodium salt, a Heparin Fragment Having High Affinity for Antithrombin III, Carbohydrate Research, 147 (1986) 221-236.

Petitou, et al., Synthesis of Heparin Fragments: A Methyl α-Pentaoside with High Affinity for Antithrombin III, Carbohydrate Research, 167 (1987) 67-75.

Poletti, et al., Chemical Contributions to Understanding Heparin Activity: Synthesis of Related Sulfated Oligosaccharides, Eur. J. Org. Chem. 2003, 2999-3024.

Popelova, et al., A Concise Synthesis of 4-nitrophenyl 2-azido-2-deoxy- and 2-acetamido-2-doexy-D-mannopyranosides, Carbohydrate Research 340 (2005) 161-166.

Sakairi, et al., Facile Preparation of 1,6-Anhydro-2-azido-3-O-benzyl-2-deoxy-?-D-glucopyranose and its 4-O-Substituted Derivatives, Bull Chem. Soc. Jpn., 67, 1756-1758 (1994).

Sakairi, et al., Insertion of a D-Glucosamine Residue into the α-Cyclodextrin Skeleton; A Model Synthesis of Chimera Cyclodextrains, J. Chem. Soci., Chem. Commun., 1991, pp. 289-290.

Tabeur, et al., L-iduronic Acid Derivatives as Glycosyl Donors, Carbohydrate Research 281 (1996) 253-276.

Tailler, et al., An Expeditious and Stereocontrolled Preparation of 2-Azido-2-deoxy-?-D-glucopyranose Derivatives from D-Glucal, J. Chem. Soc. Perkin Trans, 1992, pp. 3163-3164.

Thunberg, et al., Further Characterization of the Antithromobin-Binding Sequence in Heparin, Carbohydrate Research, 100 (1982) 393-410.

van Bockl, et al., Progress in the Chemistry of Organic Natural Product, Fortschritte der Chemi organischer Naturstoff, © 1992 by Springer-Verlag/Wien, Chemical Synthesis of Heparin Fragments and Analogues, Petitou, et al., pp. 144-209.

Van Boeckel, et al., Substituent Effects of Carbohydrate Coupling Reactions Promoted by Insoluble Silver Salts, Tetrahedron, vol. 40, No. 20 pp. 4097-4107 (1984).

Van Boeckel, et al., Synthesis of a Pentasaccharide Corresponding to the Antithrombin III Binding Fragment of Heparin, J. Carbohydrate Chemistry, 4(3), 293-321 (1985).

Van Boeckel, et al., t-Butyldimethylsilyl (TBDMS) as Protective Group in Carbohydrate Chemistry Migration of the TBDMS Group in Trans-Diol Systems, Recl. Tray. Clim Pays-Bas 102, 415-416 (1981).

van Boeckel, et al., The Unique Antithrombin III Binding Domain of Heparin: A Lead to New Synthetic Antithrombotics, Angewandte Chemie International Edition in English, vol. 32, No. 12, Dec. 1993, pp. 1671-1818.

Van den Bos, et al., Thioglycuronides: Synthesis and Application in the Assembly of Acidic Oligosaccharides, Organic Letters, 2004, vol. 6, No. 13, 2165-2168.

Van der Klein, et al., Synthesis of a Cell Wall Component of Haemophilus (Actinobacillus) Plueropneumoniae Serotype 5, Tetrahedron vol. 48, No. 22, pp. 4649-4658, 1992.

Wessel, et al., Synthesis of an N-acetylated Heparin Pentasaccharide and its Anticoagulant Activity in Comparison with the Heparin Pentasaccharide with High Anti-Factor-Xa Activity, Helvetica Chimca Acta, vol. 72 (1989), 72(6), 1268-77, 1989.

Xue, et al., A Facile Synthesis of Cerny Epoxides and Selectively Blocked Derivatives of 2-azido-2-deoxy-?-D-Glucopyranose, Tetrahedron Letters 42 (2001) 6487-6489.

Yu, et al., Novel Efficient Routes to Heparin Monosaccharides and Disaccharides Achieved via Regio- and Stereoselective Glycosidation, Organic Letters, 2004, vol. 6, No. 5, 723-726.

Zhou, et al., Toward Synthesis of the Regular Sequence of Heparin: Synthesis of Two Tetrasaccharide Precursors, Carbohydrate Research 341 (2006) 1619-1629.

Zhu, et al., New Principles for Glycoside-Bond Formation, Angew. Chem. Int. Ed. 2009, 48, 1900-1934.

Van Boeckel, et al., A Note on the Use of Porous Silver Silicates as Promoter in Carbohydrate Coupling Reactions; Recl. Tray. Chim. Pays-Bas 106, 596-598 (1987).

Tamura, et al., Synthetic Approach Towards Sulfated Chondroitin di-, tri- and tetrasaccharides corresponding to the Repeating Unit, Carbohydrate Research 305 (1998) 43-65.

Sinay, et al., Preliminary Communication, Total Synthesis of a Heparin Pentasaccharide Fragment Having High Affinity for Antithrombin III, Carbohydrate Research, 132 (1984) C5-C9.

Van den Bos, et al., Preparation of 1-Thio Uronic Acid Lactones and Their Use in Oligosaccharide Synthesis, Organic Letters, 2005, vol. 7, No. 10, 2007-2010.

Petursson, et al., Protecting Groups in Carbohydrates Chemistry, vol. 74, No. 11, Nov. 1997, Journal of Chemical Education (1297-1303.

Oikawa, et al., One-pot Preparation and Activation of Glycosyl Trichloroacetimidates: Operationally Simple Glycosylation Induced by Combined Use of Solid-supported, reactivity-opposing reagents, Tetrahedron Letters 45 (2004) 4039-4042.

Yu, et al., Glycosyl Trifluoroacetimidates. Part I: Preparation and Application as New Glycosyl Donors, Tetrahedron Letters 42 (2001) 2405-2407.

McBride, et al., A Novel Synthesis of 1,2-cis-Disaccharides, Journal of the American Chemical Society, 99:20, Sep. 28, 1977.

Basten, et al., Biologically Active Heparin-like Fragments with a "non-glycosamino" Glycan Structure. Part 3: o-alkylated-o-sulphated pentasaccharides, Bioorganic & Medicinal Chemistry Letter, vol. 2, Issue 9, Sep. 1992, pp. 905-910.

Dodoni, et al., Synthesis of α- and β-Glycosyl Asparagine Ethylene Isosteres (C-Glycosyl Asparagines) via Sugar Acetylenes and Garner Aldehyde Coupling, J. Org. Chem. 2002, 67, 4475-4486.

Fukuda, et al., Synthetic Approach Toward Antibiotic Tunicamycins. 3. Methyl 3,4,7,8-Tetra-O-acetyl-10-O-benzyl-2-benzyloxycarbonylamino-2,6-dideoxy-11,12-O-isopropylidene-β-L-dodecodialdo-(12R)-furanose-(12,9)-pyranosides-(1,5), Bull. Chem. Soc. Jpm., 55, 1574-1578 (1982).

Hung, et al., 1,6-Anhydro-β-L-hexopryanoses as Potent Synthons in the Synthesis of the Disaccharide Units of Bleomycin A2 and Heparin, J. Am. Chem. Soc. 2001, 123, 3153-3154.

Hung, et al., Novel Synthesis of 1,2:3,5-diO-isopropylidene-β-L-idofuranoside and its Derivatives at C6, Tetrahedron Letters 41 (2000) 77-80.

Izumi, et al., Synthesis of 5-Thio-l-fucose-Containing Disaccharides, as a Sequence-Specific Inhibitors, and 2'-Fucosyllactose, as a Substrate of α-l-Fucosidases, J. Org. Chem., 1997, 62, 992-998.

Figure 2 : β-configuration

FIGURE 5
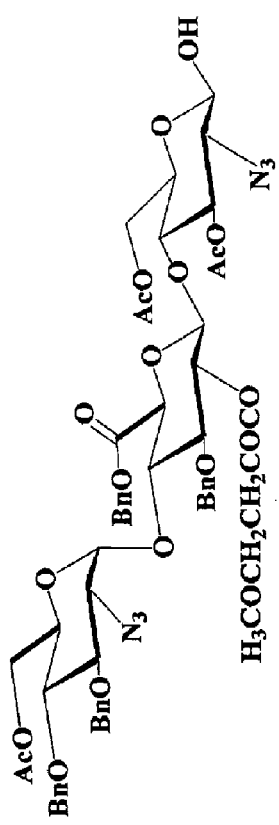
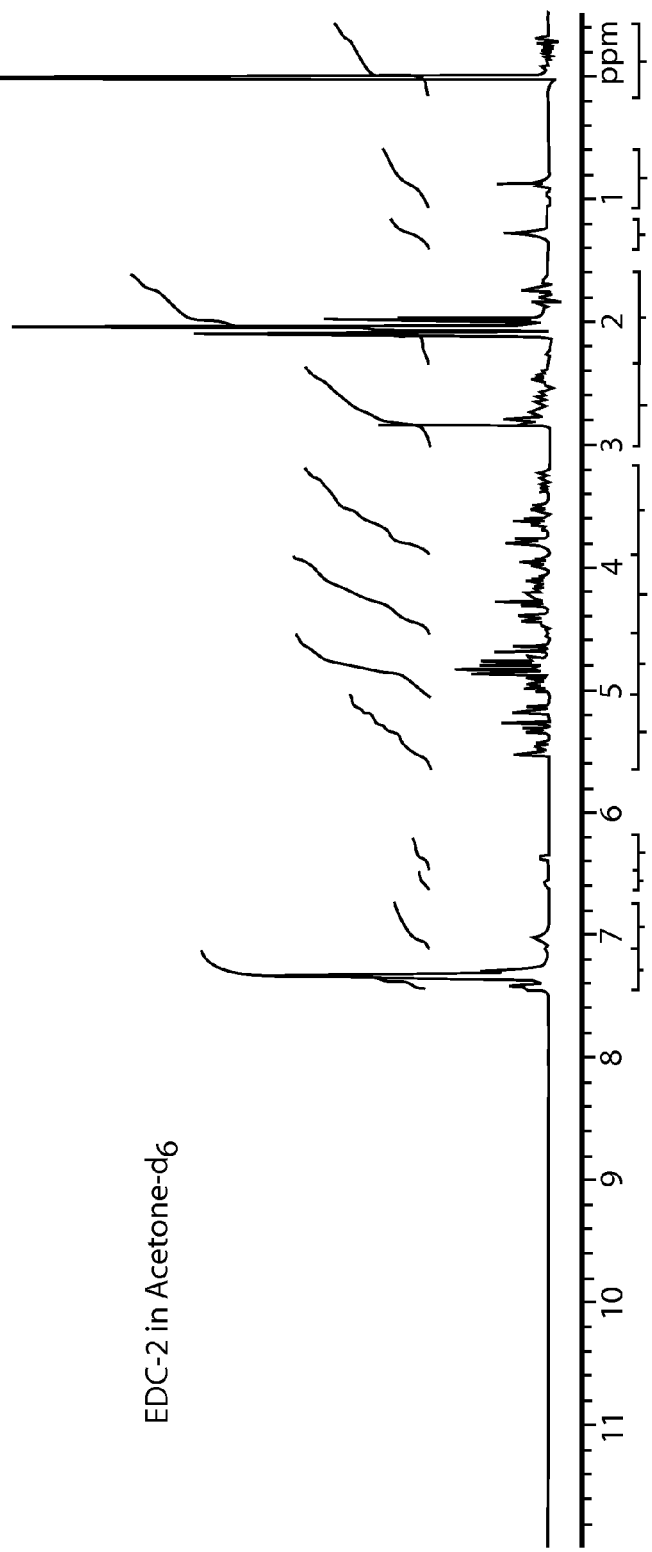
EDC-2 in Acetone-d$_6$

PROCESS FOR PERPARING FONDAPARINUX SODIUM AND INTERMEDIATES USEFUL IN THE SYNTHESIS THEREOF

CROSS-REFERENCE TO RELATED APPLICATIONS

This application is a continuation of U.S. patent application Ser. No. 13/618,786, filed Sep. 14, 2012, which is a continuation of U.S. patent application Ser. No. 12/847,719, filed Jul. 30, 2010, now U.S. Pat. No. 8,288,515, which claims the benefit of U.S. Provisional Application No. 61/230,557, filed Jul. 31, 2009, each of which is incorporated herein by reference in its entirety.

FIELD OF THE INVENTION

The present invention relates to processes for the synthesis of the Factor Xa anticoagulent Fondaparinux, and related compounds. The invention also relates to protected pentasaccharide intermediates and to an efficient and scalable process for the industrial scale production of Fondaparinux sodium by conversion of the protected pentasaccharide intermediates via a sequence of deprotection and sulfonation reactions.

BACKGROUND OF THE INVENTION

In U.S. Pat. No. 7,468,358, Fondaparinux sodium is described as the "only anticoagulant thought to be completely free of risk from HIT-2 induction." The biochemical and pharmacologic rationale for the development of a heparin pentasaccharide in *Thromb. Res.*, 86(1), 1-36, 1997 by Walenga et al. cited the recently approved synthetic pentasaccharide Factor Xa inhibitor Fondaparinux sodium. Fondaparinux has also been described in Walenga et al., *Expert Opin. Investig. Drugs*, Vol. 11, 397-407, 2002 and Bauer, *Best Practice & Research Clinical Hematology*, Vol. 17, No. 1, 89-104, 2004.

Fondaparinux sodium is a linear octasulfated pentasaccharide (oligosaccharide with five monosaccharide units) molecule having five sulfate esters on oxygen (O-sulfated moieties) and three sulfates on a nitrogen (N-sulfated moieties). In addition, Fondaparinux contains five hydroxyl groups in the molecule that are not sulfated and two sodium carboxylates. Out of five saccharides, there are three glucosamine derivatives and one glucuronic and one L-iduronic acid. The five saccharides are connected to each other in alternate α and β glycosylated linkages (see FIG. 1).

Fondaparinux sodium is a chemically synthesized methoxy derivative of the natural pentasaccharide sequence, which is the active site of heparin that mediates the interaction with antithrombin (Casu et al., *J. Biochem.*, 197, 59, 1981). It has a challenging pattern of O- and N-sulfates, specific glycosidic stereochemistry, and repeating units of glucosamines and uronic acids (Petitou et al., *Progress in the Chemistry of Organic Natural Product*, 60, 144-209, 1992).

The monosaccharide units comprising the Fondaparinux molecule are labeled as per the convention in FIG. 1, with the glucosamine unit on the right referred to as monosaccharide A and the next, an uronic acid unit to its left as B and subsequent units, C, D and E respectively. The chemical synthesis of Fondaparinux starts with monosaccharides of defined structures that are themselves referred to as Monomers A2, B1, C, D and E, for differentiation and convenience, and they become the corresponding monosaccharides in fondaparinux sodium.

Due to this complex mixture of free and sulfated hydroxyl groups, and the presence of N-sulfated moieties, the design of a synthetic route to Fondaparinux requires a careful strategy of protection and de-protection of reactive functional groups during synthesis of the molecule. Previously described syntheses of Fondaparinux all adopted a similar strategy to complete the synthesis of this molecule. This strategy can be envisioned as having four stages. The strategy in the first stage requires selective de-protection of five out of ten hydroxyl groups. During the second stage these five hydroxyls are selectively sulfonated. The third stage of the process involves the de-protection of the remaining five hydroxyl groups. The fourth stage of the process is the selective sulfonation of the 3 amino groups, in the presence of five hydroxyl groups that are not sulfated in the final molecule. This strategy can be envisioned from the following fully protected pentasaccharide, also referred to as the late-stage intermediate.

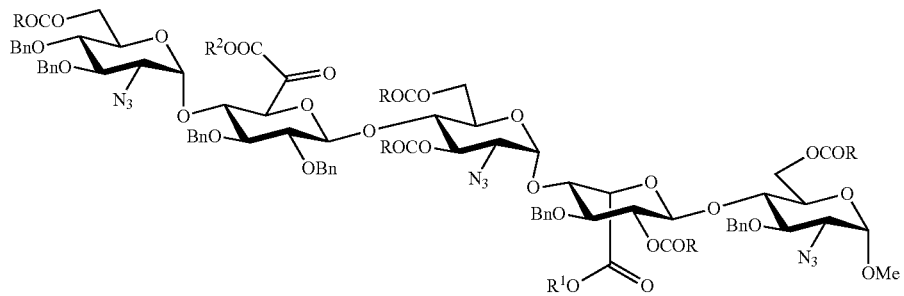

In this strategy, all of the hydroxyl groups that are to be sulfated are protected with an acyl protective group, for example, as acetates (R=CH$_3$) or benzoates (R=aryl) (Stages 1 and 2) All of the hydroxyl groups that are to remain as such are protected with benzyl group as benzyl ethers (Stage 3). The amino group, which is subsequently sulfonated, is masked as an azide (N$_3$) moiety (Stage 4). R$^1$ and R$^2$ are typically sodium in the active pharmaceutical compound (e.g., Fondaparinux sodium).

This strategy allows the final product to be prepared by following the synthetic operations as outlined below:

a) Treatment of the late-stage intermediate with base to hydrolyze (deprotect) the acyl ester groups to reveal the five hydroxyl groups. The two R$^1$ and R$^2$ ester groups are hydrolyzed in this step as well.

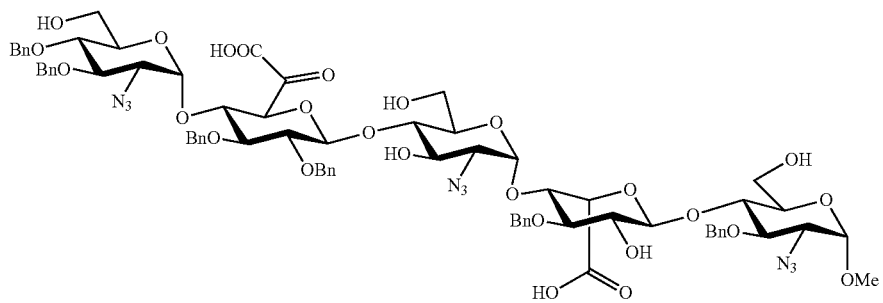

b) Sulfonation of the newly revealed hydroxyl groups.

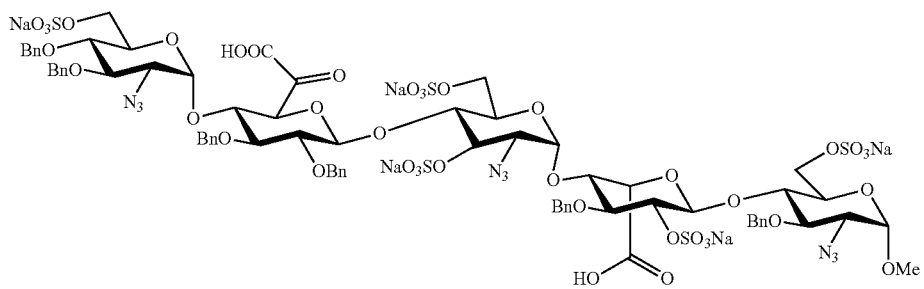

c) Hydrogenation of the O-sulfated pentasaccharide to debenzylate the five benzyl-protected hydroxyls, and at the same time, unmask the three azides to the corresponding amino groups.

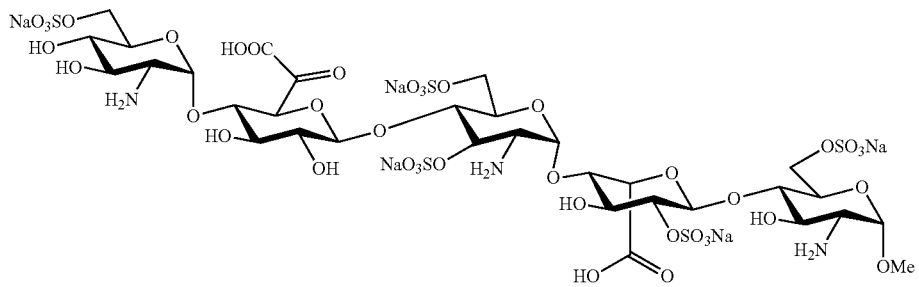

d) On the last step of the operation, the amino groups are sulfated selectively at a high pH, in the presence of the five free hydroxyls to give Fondaparinux (FIG. 1).

While the above strategy has been shown to be viable, it is not without major drawbacks. One drawback lies in the procedure leading to the fully protected pentasaccharide (late stage intermediate), especially during the coupling of the D-glucuronic acid to the next adjacent glucose ring (the D-monomer to C-monomer in the EDCBA nomenclature shown in FIG. 1). Sugar oligomers or oligosaccharides, such as Fondaparinux, are assembled using coupling reactions, also known as glycosylation reactions, to "link" sugar monomers together. The difficulty of this linking step arises because of the required stereochemical relationship between the D-sugar and the C-sugar, as shown in FIG. 2.

The stereochemical arrangement illustrated in FIG. 2 is described as having a β-configuration at the anomeric carbon of the D-sugar (denoted by the arrow). The linkage between the D and C units in Fondaparinux has this specific stereochemistry. There are, however, competing β- and α-glycosylation reactions.

The difficulties of the glycosylation reaction in the synthesis of Fondaparinux is well known. In 1991 Sanofi reported a preparation of a disaccharide intermediate in 51% yield having a 12/1 ratio of β/α stereochemistry at the anomeric position (Duchaussoy et al., Bioorg. & Med. Chem. Lett., 1(2), 99-102, 1991). In another publication (Sinay et al., Carbohydrate Research, 132, C5-C9, 1984) yields on the order of 50% with coupling times on the order of 6-days are reported. U.S. Pat. No. 4,818,816 (see e.g., column 31, lines 50-56) discloses a 50% yield for the β-glycosylation.

Alchemia's U.S. Pat. No. 7,541,445 is even less specific as to the details of the synthesis of this late-stage Fondaparinux synthetic intermediate. The '445 patent discloses several strategies for the assembly of the pentasaccharide (1+4, 3+2 or 2+3) using a 2-acylated D-sugar (specifically 2-allyloxycarbonyl) for the glycosylation coupling reactions. However, Alchemia's strategy involves late-stage pentasaccharides that all incorporate a 2-benzylated D-sugar. The transformation of acyl to benzyl is performed either under acidic or basic conditions. Furthermore, these transformations, using benzyl bromide or benzyl trichloroacetimidate, typically result in extensive decomposition and the procedure suffers from poor yields. Thus, such transformations (at a disaccharide, trisaccharide, and pentasaccharide level) are typically not acceptable for industrial scale production.

Examples of fully protected pentasaccharides are described in Duchaussoy et al., *Bioorg. Med. Chem. Lett.,* 1 (2), 99-102, 1991; Petitou et al., *Carbohydr. Res.,* 167, 67-75, 1987; Sinay et al., *Carbohydr. Res.,* 132, C5-C9, 1984; Petitou et al., *Carbohydr. Res.,* 1147, 221-236, 1986; Lei et al., *Bioorg. Med. Chem.,* 6, 1337-1346, 1998; Ichikawa et al., *Tet. Lett.,* 27(5), 611-614, 1986; Kovensky et al., *Bioorg. Med. Chem.,* 1999, 7, 1567-1580, 1999. These fully protected pentasaccharides may be converted to the O— and N-sulfated pentasaccharides using the four steps (described earlier) of: a) saponification with LiOH/$H_2O_2$/NaOH, b) O-sulfation by an $Et_3N$—$SO_3$ complex; c) de-benzylation and azide reduction via $H_2$/Pd hydrogenation; and d) N-sulfation with a pyridine-$SO_3$ complex.

Even though many diverse analogs of the fully protected pentasaccharide have been prepared, none use any protective group at the 2-position of the D unit other than a benzyl group. Furthermore, none of the fully protected pentasaccharide analogs offer a practical, scaleable and economical method for re-introduction of the benzyl moiety at the 2-position of the D unit after removal of any participating group that promotes β-glycosylation.

Furthermore, the coupling of benzyl protected sugars proves to be a sluggish, low yielding and problematic process, typically resulting in substantial decomposition of the pentasaccharide (prepared over 50 synthetic steps), thus making it unsuitable for a large [kilogram] scale production process.

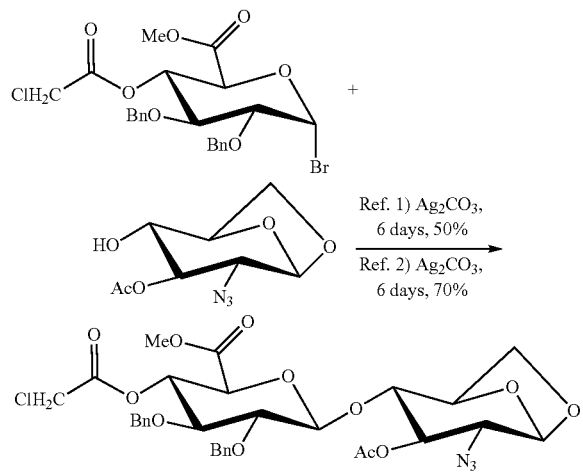

Ref. 1. Sinay et al., *Carbohydr. Res.,* 132, C5-C9, 1984.
Ref. 2. Petitou et al., *Carbohydr. Res.,* 147, 221-236, 1986

It has been a general strategy for carbohydrate chemists to use base-labile ester-protecting group at 2-position of the D unit to build an efficient and stereoselective β-glycosidic linkage. To construct the β-linkage carbohydrate chemists have previously acetate and benzoate ester groups, as described, for example, in the review by Poletti et al., *Eur. J. Chem.,* 2999-3024, 2003.

The ester group at the 2-position of D needs to be differentiated from the acetate and benzoates at other positions in the pentasaccharide. These ester groups are hydrolyzed and sulfated later in the process and, unlike these ester groups, the 2-hydroxyl group of the D unit needs to remain as the hydroxyl group in the final product, Fondaparinux sodium.

Some of the current ester choices for the synthetic chemists in the field include methyl chloro acetyl and chloro methyl acetate [MCA or CMA]. The mild procedures for the selective removal of theses groups in the presence of acetates and benzoates makes them ideal candidates. However, MCA/CMA groups have been shown to produce unwanted and serious side products during the glycosylation and therefore have not been favored in the synthesis of Fondaparinux sodium and its analogs. For by-product formation observed in acetate derivatives see Seeberger et al., *J. Org. Chem.,* 2004, 69, 4081-93. Similar by-product formation is also observed using chloroacetate derivatives. See Orgueira et al., *Eur. J. Chem.,* 9(1), 140-169, 2003.

Therefore, as will be appreciated, there are several limitations to current processes used for the synthesis of fondaparinux sodium. Thus, there is a need in the art for new synthetic procedures that produce fondaparinux and related compounds in high yield and with high stereoselectivity. The processes of the present invention address the limitations known in the art and provide a unique, reliable and scalable synthesis of compounds such as Fondaparinux sodium.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

SUMMARY OF THE INVENTION

Applicants have surprisingly found that in the synthesis of Fondaparinux, the use of a unique levulinate-protected 2-glucuronic acid-anhydro sugar coupling methodology allows for a highly efficient glycosylation reaction, thereby providing late stage intermediates or oligosaccharides (and Fondaparinux related oligomers) in high yield and in high β/α ratios. In particular, glycosylation of the 2-levulinate-protected glucuronic acid can occur with high coupling yields (>65%) of the β-isomer, rapidly (for example, in an hour reaction time), and with no detectable α-isomer upon column chromatography purification. The levulinate protecting group may be efficiently and selectively removed from the glycosylated product in the presence of potential competing moieties (such as two acetate and two benzoate groups) to generate a free 2-hydroxyl group. The newly generated hydroxyl group may be efficiently and quantitatively re-protected with a tetrahydropyran (THP) group to provide a fully protected 2-THP containing pentasaccharide that may be selectively and consequentially O-sulfated, hydrogenated and N-sulfated to produce the desired pentasaccharide, such as Fondaparinux, in excellent yields. The inventors have surprisingly found that the THP group remains intact and protected through all of the subsequent operations and is efficiently removed during work-up, after the final N-sulfonation step.

The present invention includes certain intermediate compounds identified below, including those of Formula I.

One embodiment of the invention is a process for making Fonadparinux sodium by converting at least one compound selected from

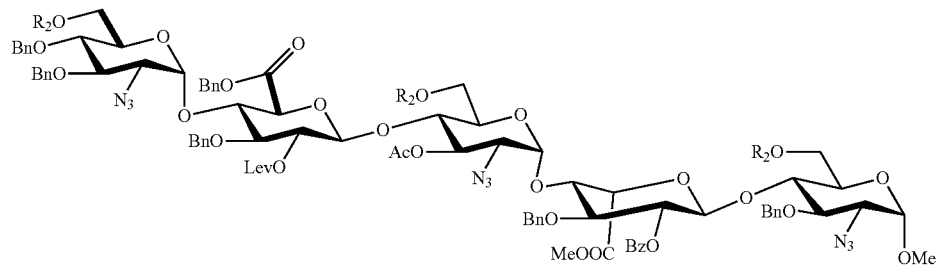
where R₂ is Ac or Bz,
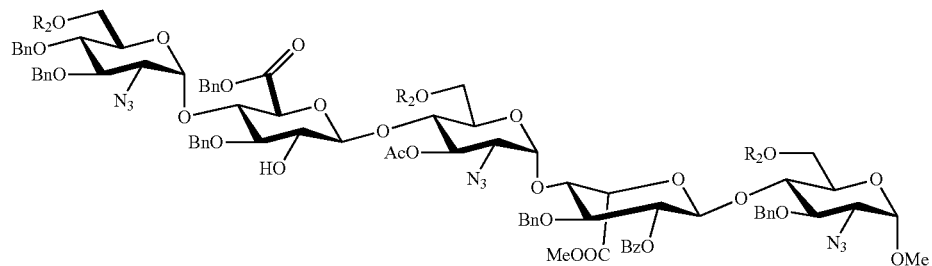
where R₂ is Ac or Bz,
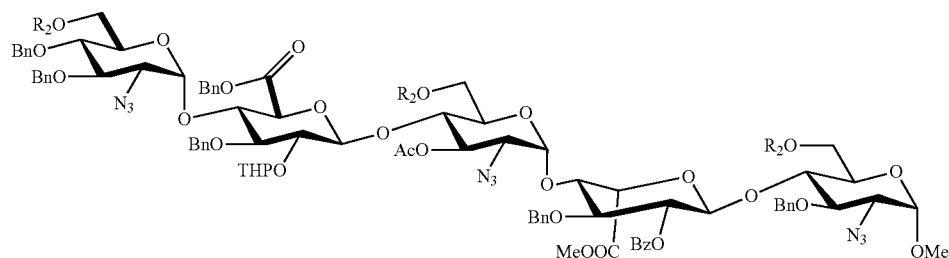
where R₂ is Ac or Bz,
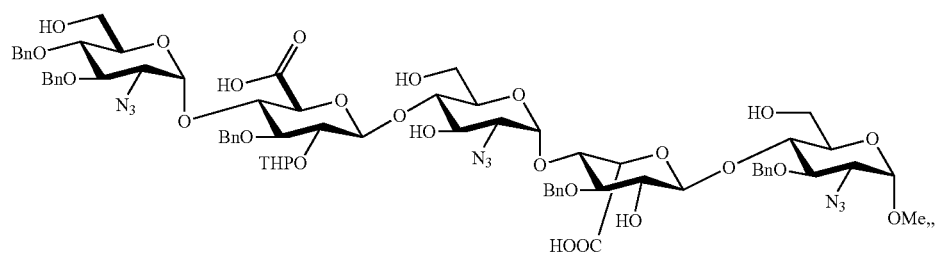
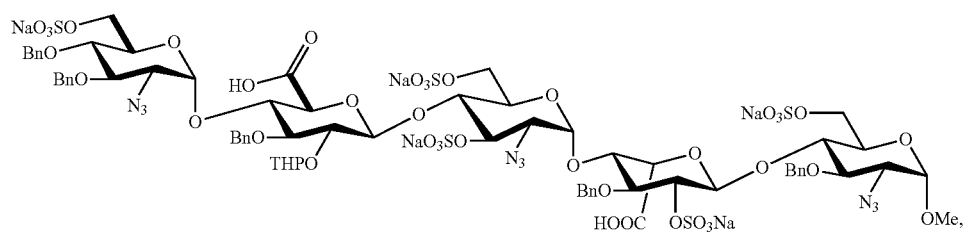

-continued

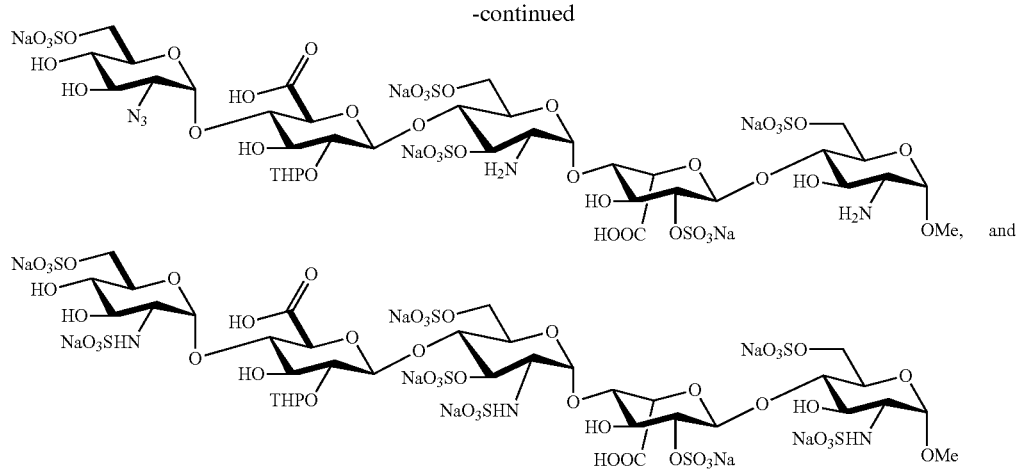

to Fonadaparinux sodium.

Yet another embodiment is a method of preparing an oligosaccharide having a β-glucosamine glycosidic linkage by reacting a 1,6-anhydro glucopyranosyl acceptor (e.g., 1,6-anhydro-β-D-glucopyranose) having an azide functional group at C2 and a hydroxyl group at C4 with a uronic acid glycopyranosyl donor having an activated anomeric carbon, a levulinate group at C2, and a protected acid group at C5 to form an oligosaccharide having a β-glycosidic linkage between the hydroxyl group of the glucopyranosyl acceptor and the anomeric carbon of the glycopyranosyl donor.

BRIEF DESCRIPTION OF THE FIGURES

FIG. 5 is a $^1$H NMR spectrum of the EDC-2 trimer.

DETAILED DESCRIPTION OF THE INVENTION

Figure 1:
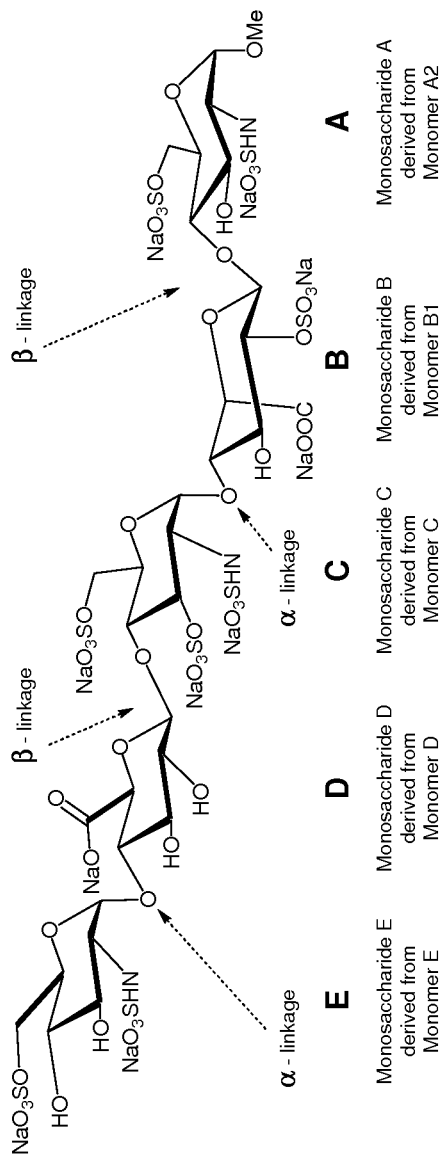
FIG. 1 depicts the structure of Fondaparinux sodium.
Figure 2:
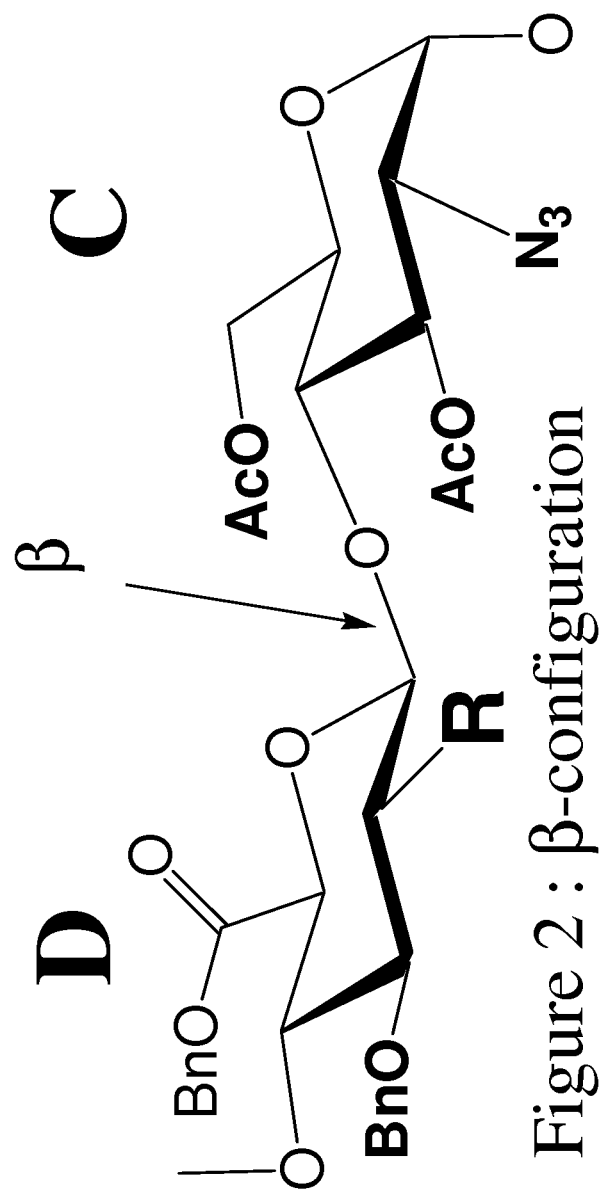
FIG. 2 depicts the stereochemical relationship between the D-sugar and the C-sugar in Fondaparinux sodium.

Applicants have surprisingly found that in the synthesis of Fondaparinux, the use of a unique levulinate-protected 2-glucuronic acid-anhydro sugar coupling methodology allows for an highly efficient glycosylation reaction, thereby providing late stage intermediates or oligosaccharides (and Fondaparinux related oligomers) in high yield and in high β/α ratios. In particular, glycosylation of the 2-levulinate-protected glucuronic acid with an anhydro sugar occurs quickly (for example, with a reaction time of about an hour), with high coupling yields (>65%) of the β-isomer, and with high selectivity (for example, with no detectable α-isomer upon column chromatography purification). The levulinate protecting group may be efficiently and selectively removed from the glycosylated product in the presence of potential competing moieties (such as two acetate and two benzoate groups) to generate a free 2-hydroxyl group. The newly generated hydroxyl group may be efficiently and quantitatively re-protected with a tetrahydropyran (THP) group to provide a fully protected 2-THP containing pentasaccharide that may be selectively and consequentially O-Sulfated, hydrogenated and N-sulfated to produce the desired pentasaccharide, such as Fondaparinux, in excellent yields. The THP group remains intact and protected through all of the subsequent operations and is efficiently removed during work-up, after the final N-sulfonation step.

The levulinyl group can be rapidly and almost quantitatively removed by treatment with hydrazine hydrate as the deprotection reagent as illustrated in the example below. Under the same reaction conditions primary and secondary acetate and benzoate esters are hardly affected by hydrazine hydrate. See, e.g., Seeberger et al., *J. Org. Chem.*, 69, 4081-4093, 2004.

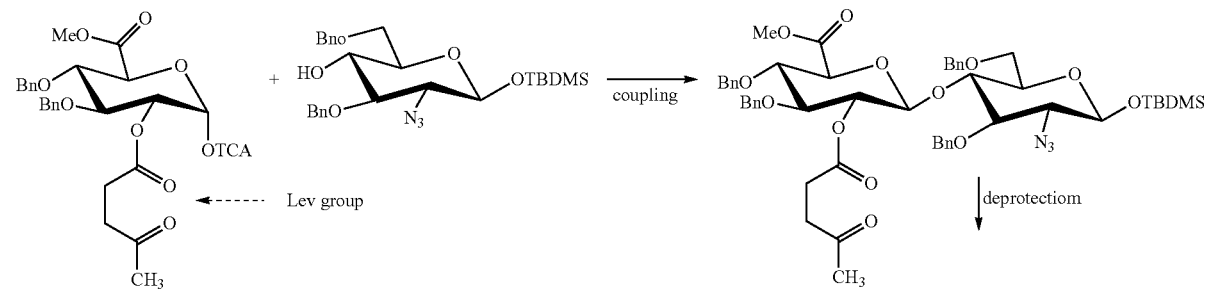

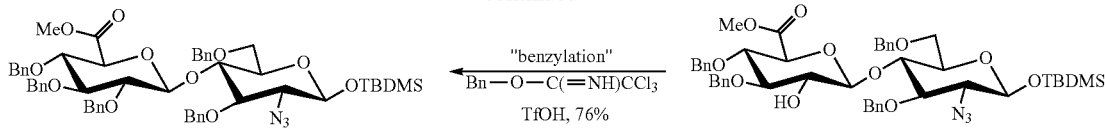

The syntheses of Fondaparinux sodium described herein takes advantage of the levulinyl group in efficient construction of the trisaccharide EDC with improved β-selectivity for the coupling under milder conditions and increased yields.

described herein, the THP group is incorporated at the 2-position of the D unit at this late stage of the synthesis (i.e., after the D and C units have been coupled through a 1,2-trans glycosidic (β-) linkage). The THP protective group typically

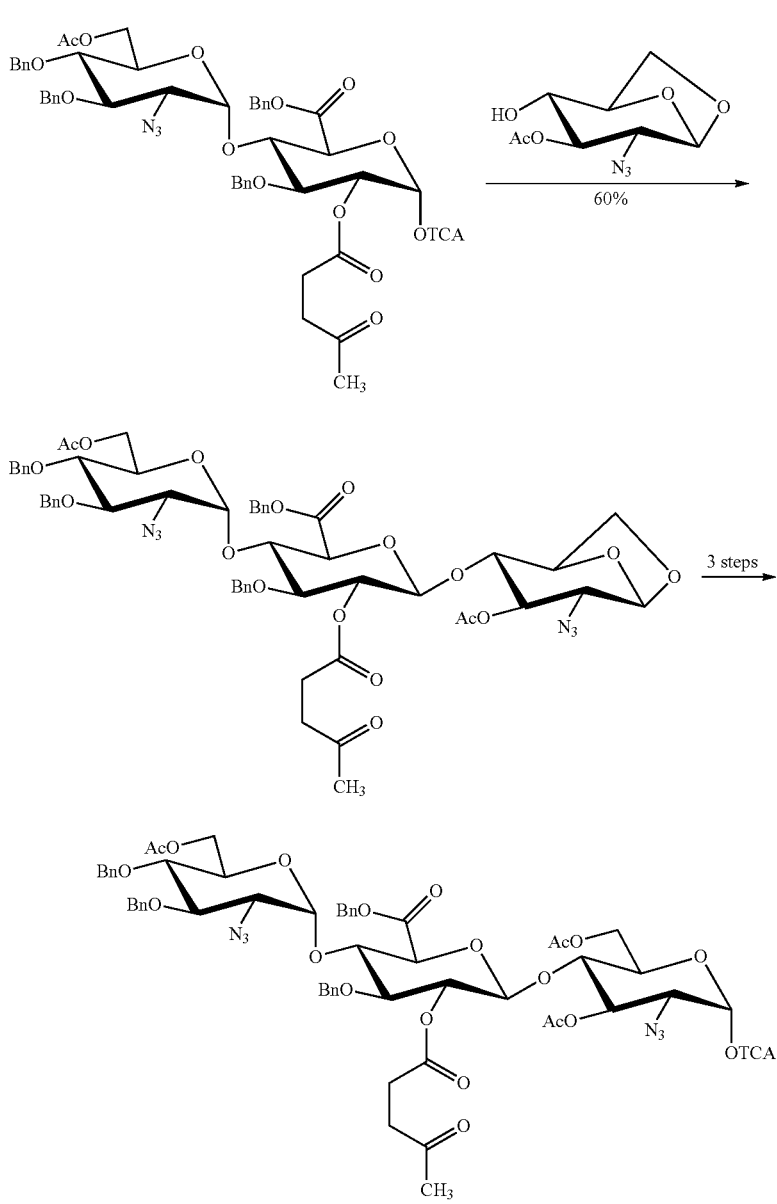

Substitution of the benzyl protecting group with a THP moiety provides its enhanced ability to be incorporated quantitatively in position-2 of the unit D of the pentasaccharide. Also, the THP group behaves in a similar manner to a benzyl ether in terms of function and stability. In the processes does not promote an efficient β-glycosylation and therefore is preferably incorporated in the molecule after the construction of the β-linkage.

The scheme below exemplifies some of the processes of the present invention disclosed herein.

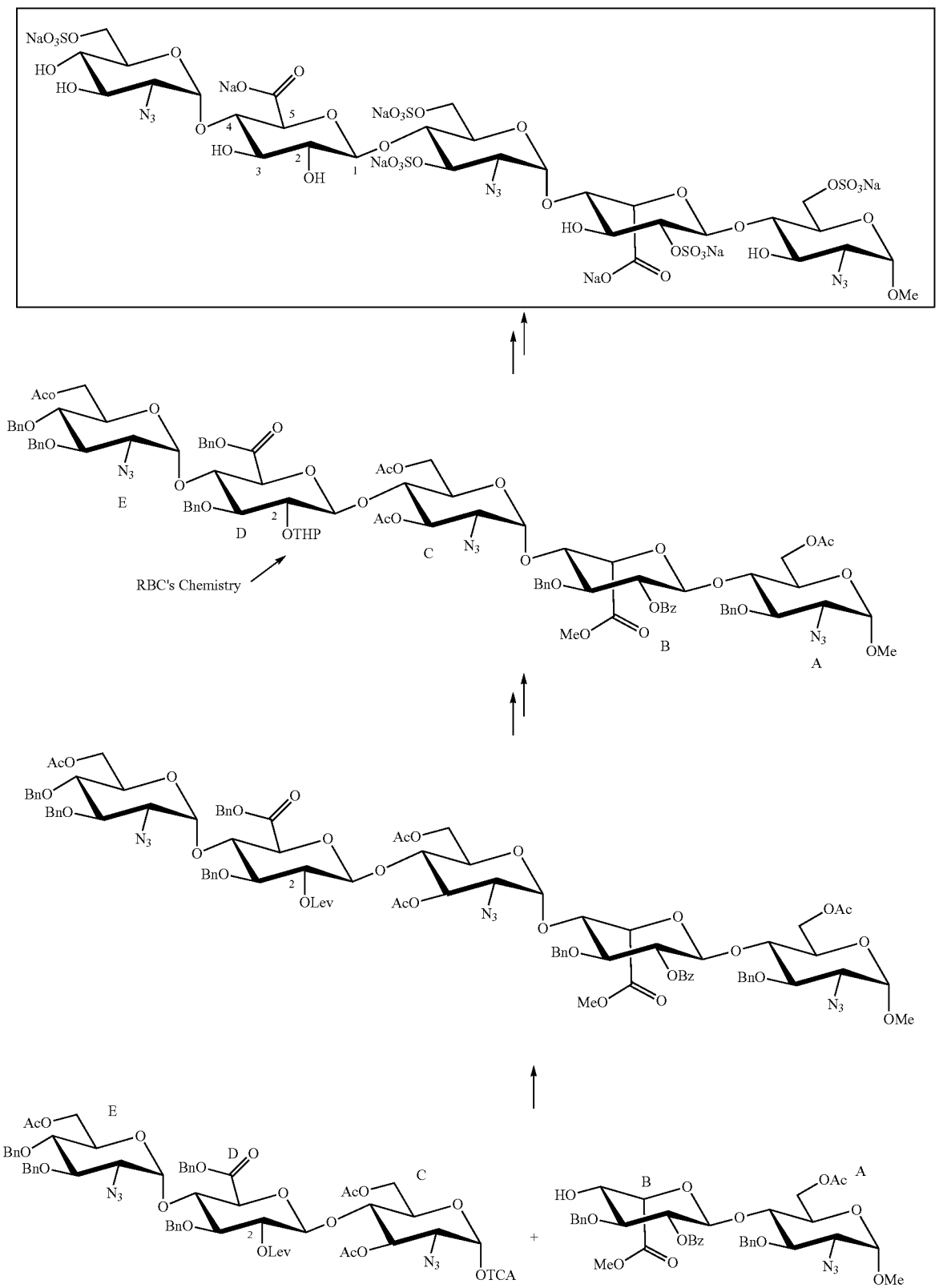
The tetrahydropyranyl (THP) protective group and the benzyl ether protective group are suitable hydroxyl protective groups and can survive the last four synthetic steps (described above) in the synthesis of Fondaparinux sodium, even under harsh reaction conditions. Certain other protecting groups do not survive the last four synthetic steps in high yield.

Thus, in one aspect, the present invention relates to novel levulinyl and tetrahydropyran pentasaccharides. Such compounds are useful as intermediates in the synthesis of Fondaparinux.

In one embodiment, the present invention relates to a compound of Formula I:

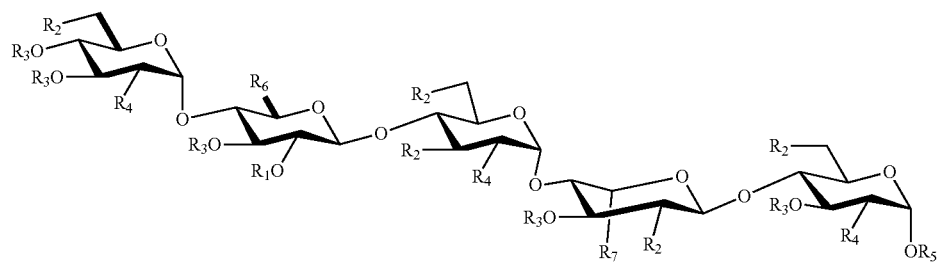

Formula I wherein $R_1$ is levulinyl (Lev) or tetrahydropyran (THP);

$R_2$ is —O⁻ or a salt thereof, —OH, —OAcyl, or —OSO$_3$⁻ or a salt thereof;

$R_3$ is H, benzyl or a protecting group removable by hydrogenation (a hydroxyl protecting group) (for example, —CO$_2$⁻ or a salt thereof);

$R_4$ is $N_3$ (azide), $NH_2$, NH-protecting group (i.e., —NH—R where R is an amino protecting group), or NHSO$_3$⁻ or a salt thereof (e.g., NHSO$_3$Na, NHSO$_3$Li, NHSO$_3$K, and NHSO$_3$NH$_4$);

$R_5$ is $C_1$-$C_6$ alkyl; and $R_6$ and $R_7$ are independently selected from —CO$_2$⁻ or a salt thereof, —CO$_2$H, and —CO$_2$R$_x$ (where $R_x$ is a $C_1$-$C_6$ alkyl, aryl, $C_1$-$C_4$ alkoxy(aryl), aryl($C_1$-$C_6$ alkyl), or $C_1$-$C_4$ alkoxy (aryl)($C_1$-$C_6$ alkyl)) (e.g., —CO$_2$Me, —CO$_2$CH$_2$C$_6$H$_5$ and —CO$_2$CH$_2$C$_6$H$_4$OMe); and wherein said compound has alpha (α) stereochemistry at the carbon bearing the —OR$_5$ group.

In one embodiment, $R_2$ is —O-Acetyl or —O-Benzoyl. In another embodiment, $R_2$ is —O⁻, —ONa, —OLi, —OK or —OCs. In a further embodiment, $R_2$ is —OSO$_3$⁻, —OSO$_3$Na, —OSO$_3$Li, —OSO$_3$K or —OSO$_3$Cs.

In another embodiment, $R_5$ is methyl.

In a further embodiment, $R_3$ is benzyl or p-methoxybenzyl. In yet a further embodiment, $R_3$ is —CO$_2$⁻, —CO$_2$Na, —CO$_2$Li, —CO$_2$K or —CO$_2$Cs.

In one embodiment of the compound of Formula (I), $R_1$ is levulinyl (Lev), $R_2$ is —OAcetyl or —OBenzoyl, $R_3$ is benzyl, $R_4$ is $N_3$ (azide), $R_5$ is methyl, $R_6$ is —CO$_2$CH$_2$C$_6$H$_5$ and $R_7$ is —CO$_2$Me.

In another embodiment of the compound of Formula (I), $R_1$ is tetrahydropyran (THP), $R_2$ is —OAcetyl or —OBenzoyl, $R_3$ is benzyl, $R_4$ is $N_3$ (azide), $R_5$ is methyl, $R_6$ is —CO$_2$CH$_2$C$_6$H$_5$ and $R_7$ is —CO$_2$Me.

In yet another embodiment of the compound of Formula (I), $R_1$ is tetrahydropyran (THP), $R_2$ is —O⁻ or a salt thereof, $R_3$ is benzyl, $R_4$ is $N_3$ (azide), $R_5$ is methyl, and $R_6$ and $R_7$ are —CO$_2$⁻ or a salt thereof.

In a further embodiment of the compound of Formula (I), $R_1$ is tetrahydropyran (THP), $R_2$ is —OSO$_3$⁻ or a salt thereof, $R_3$ is benzyl, $R_4$ is $N_3$ (azide), $R_5$ is methyl, and $R_6$ and $R_7$ are —CO$_2$ or a salt thereof.

In another embodiment of the compound of Formula (I), $R_1$ is tetrahydropyran (THP), $R_2$ is —OSO$_3$⁻ or a salt thereof, $R_3$ is H, $R_4$ is $NH_2$, $R_5$ is methyl, and $R_6$ and $R_7$ are —CO$_2$⁻ or a salt thereof.

In another embodiment of the compound of Formula (I), $R_1$ is tetrahydropyran (THP), $R_2$ is —OSO$_3$Na, $R_3$ is H, $R_4$ is NHSO$_3$Na, $R_5$ is methyl, and $R_6$ and $R_7$ are —CO$_2$Na.

In yet a further embodiment, the present invention relates to a compound of Formula I:

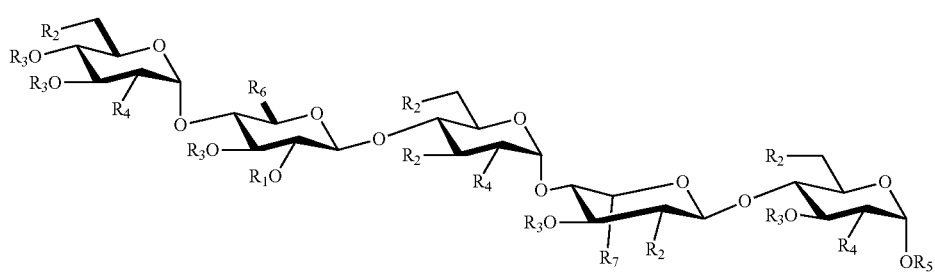

Formula I wherein $R_1$ is H, $R_2$ is —OAcetyl or —OBenzoyl, $R_3$ is benzyl, $R_4$ is $N_3$ (azide), $R_5$ is methyl, $R_6$ is —CO$_2$CH$_2$C$_6$H$_5$ and $R_7$ is —CO$_2$Me.

Synthetic Processes

In another aspect, the present invention relates to processes for the preparation of fondaparinux. The invention also relates to processes for the preparation of novel intermediates useful in the synthesis of fondaparinux. The processes described herein proceed in an efficient manner, thereby providing the desired compounds in good yield and in a manner that is scalable and reproducible on an industrial scale.

Selective Coupling Strategy

The present invention provides a procedure for the selective formation of a β-anomer product from a glycosylation coupling reaction. Without wishing to be bound by theory, the applicants believe that the β/α ratio observed during the processes described herein is due to the levulinate-directed glycosylation exemplified below:

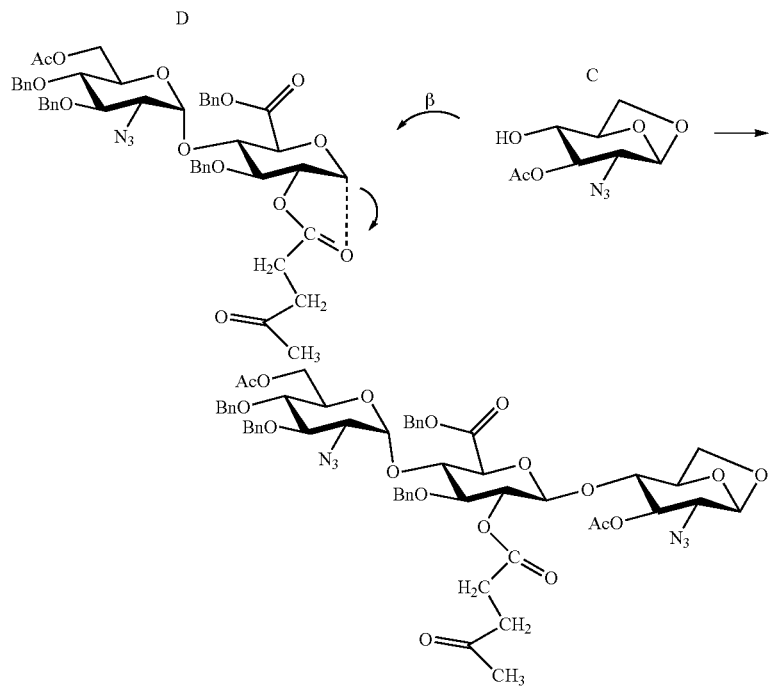

The 2-levulinate-mediated glycosylation reactions described herein provide a surprisingly high β/α ratio of coupled products. In the present invention, a high β-selectivity is obtained when the present, conformationally restricted, anhydro acceptor C is used. The high β-selectivity is unexpected and may be due the conformationally locked anhydroglucose.

Thus, in certain aspects, the present invention provides a levulinate ester/tetrandropyranyl ether (Lev/THP) strategy for the protection, deprotection and re-protection of the 2-position of a glucuronic saccharide, which is useful for the synthesis of Fondaparinux and related compounds.

In one embodiment, the present invention relates to a process for preparing fondaparinux sodium:

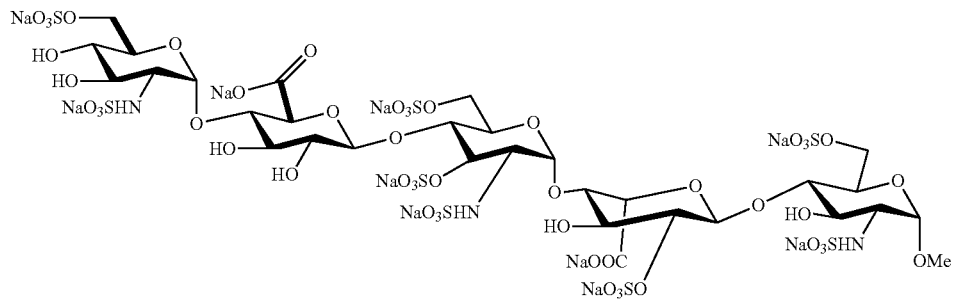

In certain embodiments, the process includes (a) at least one of:
(i) deprotecting and then THP protecting a levulinate pentamer of the formula:

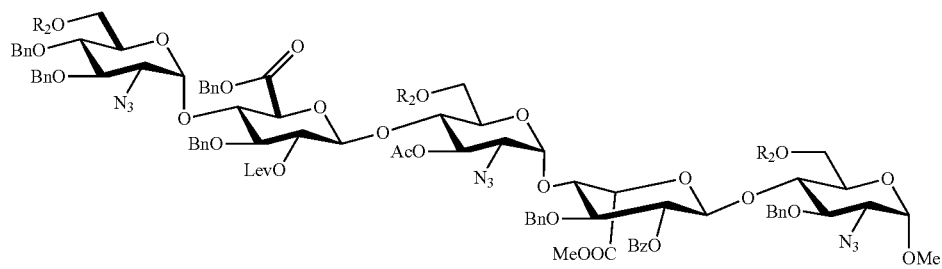

where $R_2$ is Ac or Bz to obtain a THP pentamer of the formula:
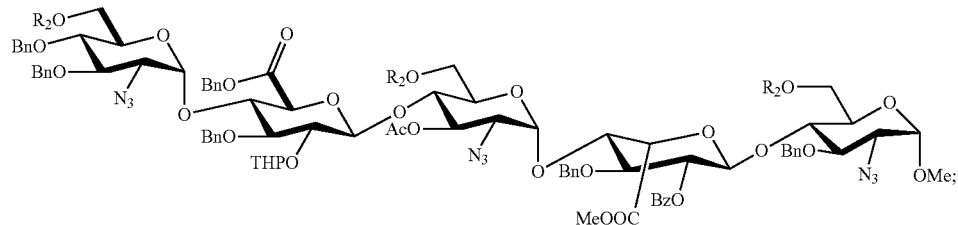
(ii) hydrolyzing a THP pentamer of the formula:
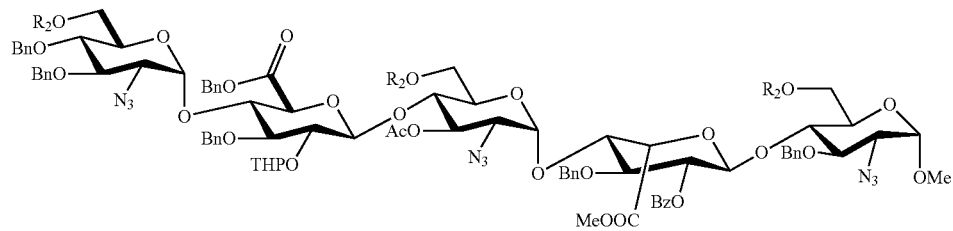
where $R_2$ is Ac or Bz to obtain a hydrolyzed pentamer of the formula:
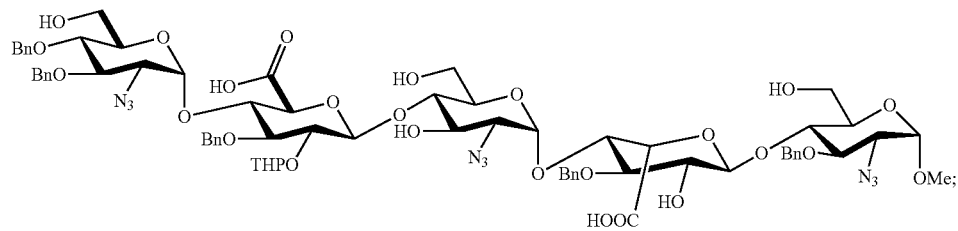
(iii) sulfating a hydrolyzed pentamer of the formula:
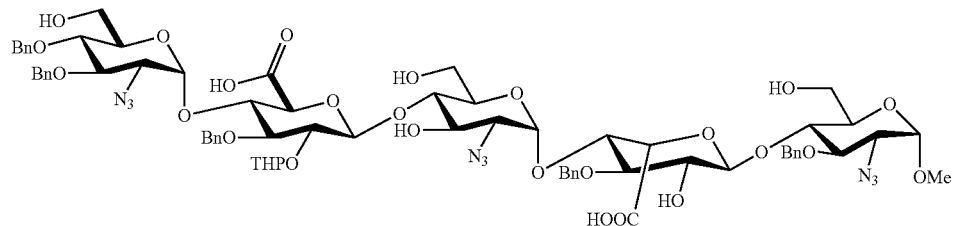
to obtain an O-sulfated pentamer of the formula:
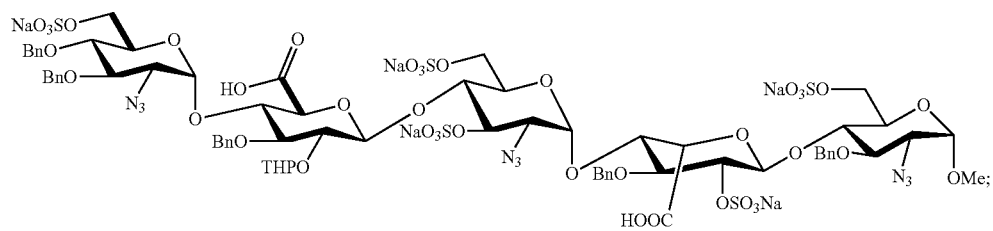

(iv) hydrogenating an O-sulfated pentamer of the formula:

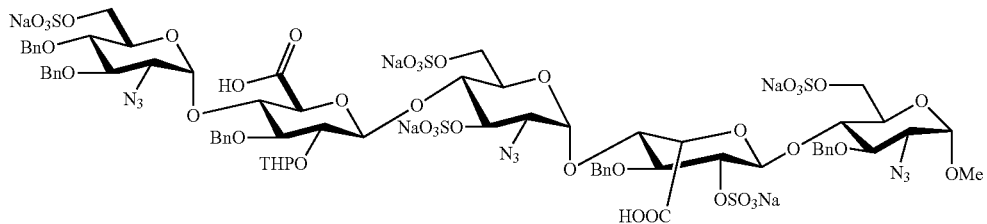

to obtain a hydrogenated pentamer of the formula:

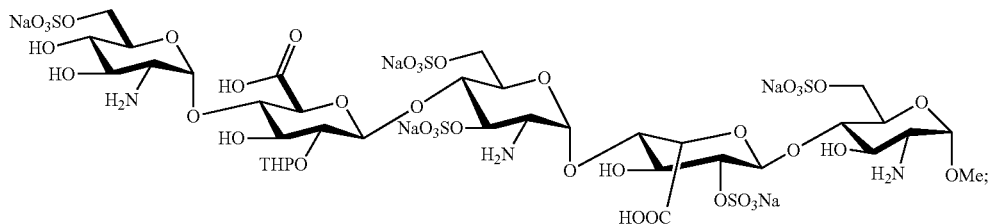

and
(vi) N-sulfating a hydrogenated pentamer of the formula:

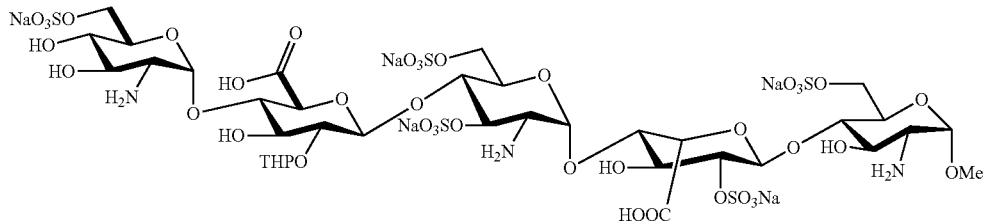

to obtain Fondaparinux-THP of the formula:

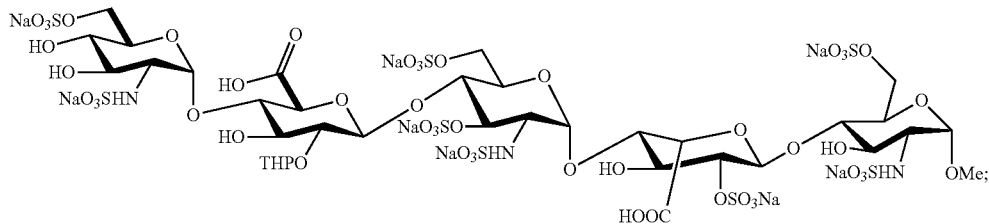

and
(b) optionally, converting the product of step (a) to Fondaparinux sodium. For instance, the Fondaparinux-THP intermediate shown above can be deprotected (i.e., the THP protecting group can be removed) to obtain Fondaparinux.

In another aspect, the present invention relates to a process for preparing a compound of Formula I:

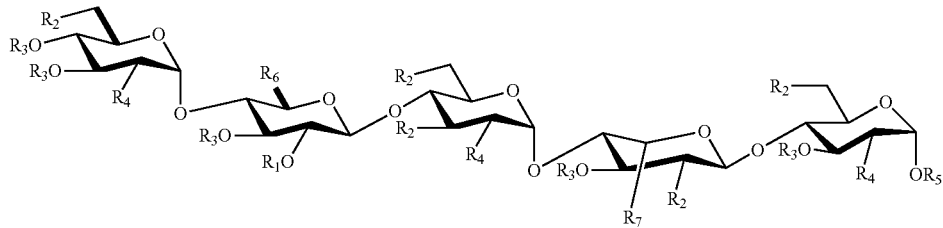

Formula I wherein $R_1$ is H, $R_2$ is —$OSO_3Na$, $R_3$ is H, $R_4$ is $NHSO_3Na$, $R_5$ is methyl, and $R_6$ and $R_7$ are —$CO_2Na$, the process including:

(a) deprotecting a compound of Formula I wherein $R_1$ is levulinyl (Lev), $R_2$ is —OAcetyl or —OBenzoyl, $R_3$ is benzyl, $R_4$ is $N_3$ (azide), $R_5$ is methyl, $R_6$ is —$CO_2CH_2C_6H_5$ and $R_7$ is —$CO_2Me$, to provide a compound of Formula I wherein $R_1$ is H, $R_2$ is —OAcetyl or —OBenzoyl, $R_3$ is benzyl, $R_4$ is $N_3$ (azide), $R_5$ is methyl, $R_6$ is —$CO_2CH_2C_6H_5$ and $R_7$ is —$CO_2Me$;

(b) protecting the product of step (a) to provide a compound of Formula I wherein $R_1$ is tetrahydropyran (THP), $R_2$ is —OAcetyl or —OBenzoyl, $R_3$ is benzyl, $R_4$ is $N_3$ (azide), $R_5$ is methyl, $R_6$ is —$CO_2CH_2C_6H_5$ and $R_7$ is —$CO_2Me$;

(c) hydrolyzing the product of step (b) to provide a compound of Formula I wherein $R_1$ is tetrahydropyran (THP), $R_2$ is —$O^-$ or a salt thereof, $R_3$ is benzyl, $R_4$ is $N_3$ (azide), $R_5$ is methyl, and $R_6$ and $R_7$ are —$CO_2^-$ or a salt thereof;

(d) sulfating the product of step (c) to provide a compound of Formula I wherein $R_1$ is tetrahydropyran (THP), $R_2$ is —$OSO_3^-$ or a salt thereof, $R_3$ is benzyl, $R_4$ is $N_3$ (azide), $R_5$ is methyl, and $R_6$ and $R_7$ are —$CO_2^-$ or a salt thereof;

(e) hydrogenating the product of step (d) to provide a compound of Formula I wherein $R_1$ is tetrahydropyran (THP), $R_2$ is —$OSO_3^-$ or a salt thereof, $R_3$ is H, $R_4$ is $NH_2$, $R_5$ is methyl, and $R_6$ and $R_7$ are —$CO_2^-$ or a salt thereof;

(f) sulfating the product of step (e) to provide a compound of Formula I wherein $R_1$ is tetrahydropyran (THP), $R_2$ is —$OSO_3Na$, $R_3$ is H, $R_4$ is $NHSO_3Na$, $R_5$ is methyl, and $R_6$ and $R_7$ are —$CO_2Na$; and (g) deprotecting the product of step (f) to provide a compound of Formula I wherein $R_1$ is H, $R_2$ is —$OSO_3Na$, $R_3$ is H, $R_4$ is $NHSO_3Na$, $R_5$ is methyl, and $R_6$ and $R_7$ are —$CO_2Na$.

In one embodiment, deprotecting step (a) includes treatment with a reagent selected from hydrazine, hydrazine hydrate, hydrazine acetate and $R_8NH$—$NH_2$ where $R_8$ is aryl, heteroaryl or alkyl.

In one embodiment, deprotecting step (a) includes treatment with hydrazine

In another embodiment, protecting step (b) includes treatment with dihyropyran or a dihydropyran derivative and an acid selected from camphor sulfonic acid (CSA), hydrochloric acid (HCl), p-toluenesulfonic acid (pTsOH) and Lewis acids.

In one embodiment protecting step (b) includes treatment with dihyropyran and an acid selected from hydrochloric acid and p-toluenesulfonic acid.

In another aspect, the present invention relates to a process for preparing a THP pentamer of the formula:

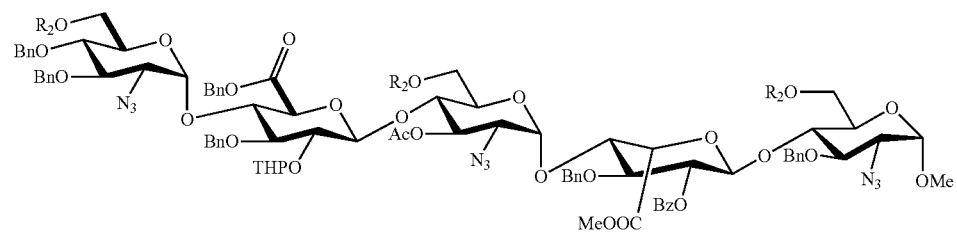

wherein $R_2$ is Ac or Bz;
the process including deprotecting and then THP protecting a compound of the formula:

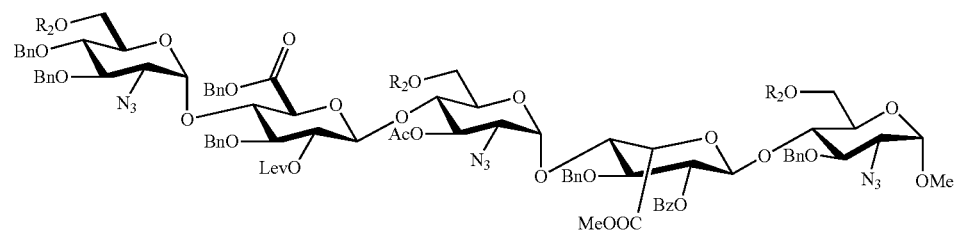

In a further embodiment of this aspect, the process further includes hydrolyzing the THP pentamer to produce a hydrolyzed pentamer of the formula:

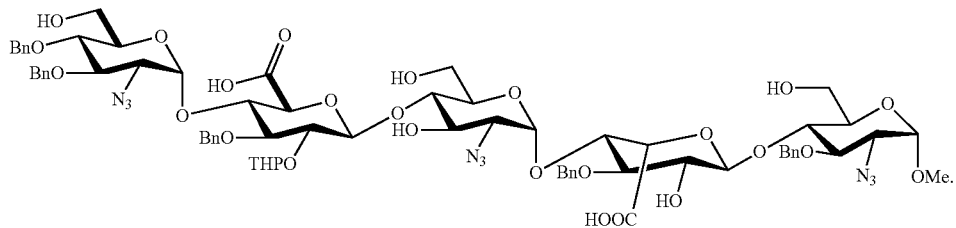

In a further embodiment of this aspect, the process further includes sulfating the hydrolyzed pentamer to obtain an O-sulfated pentamer of the formula:

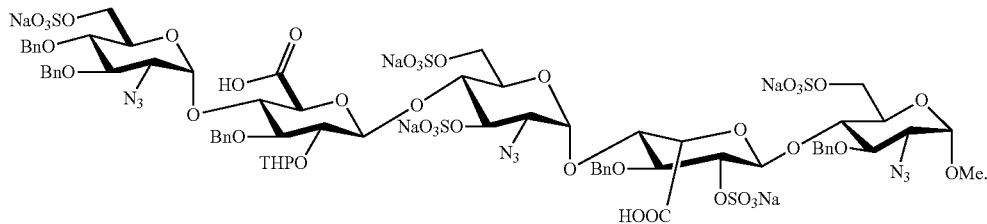

In a further embodiment of this aspect, the process further includes hydrogenating the O-sulfated pentamer to obtain a hydrogenated pentamer of the formula:

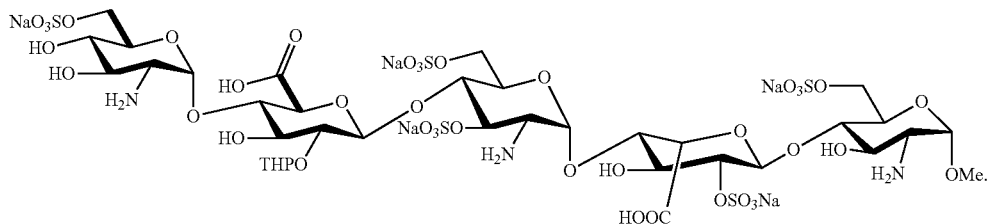

In a further embodiment of this aspect, the process further includes N-sulfating the hydrogenated pentamer to obtain fondaparinux-THP of the formula:

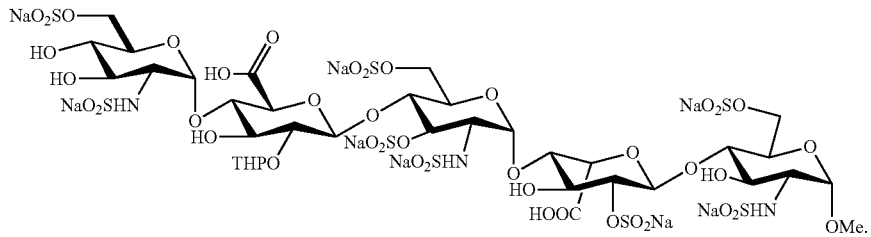

In a further embodiment of this aspect, the process further includes converting the Fondaparinux-THP to Fondaparinux sodium. In one embodiment, the conversion includes deprotecting the Fondaparinux-THP.

In another aspect, the present invention relates to a process for preparing a compound of Formula I:

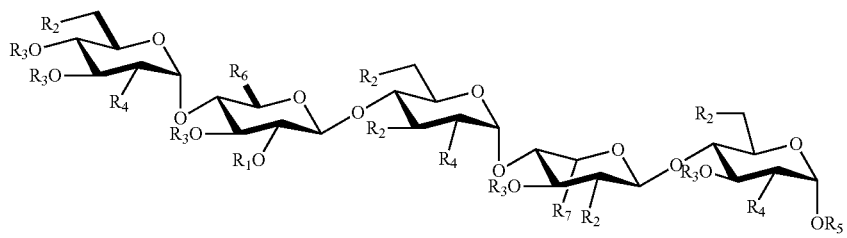

Formula I wherein $R_1$ is levulinyl (Lev), $R_2$ is —OAcetyl or —OBenzoyl, $R_3$ is benzyl, $R_4$ is $N_3$ (azide), $R_5$ is methyl, $R_6$ is —CO$_2$CH$_2$C$_6$H$_5$ and $R_7$ is —CO$_2$Me;

the process including linking a compound of Formula EDC

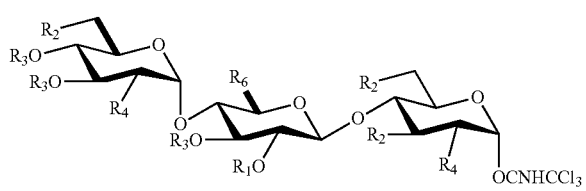

Formula EDC wherein $R_1$ is levulinyl (Lev), $R_2$ is —OAcetyl or —OBenzoyl, $R_3$ is benzyl, $R_4$ is $N_3$ (azide) and $R_6$ is —CO$_2$CH$_2$C$_6$H$_5$;

with a compound of Formula BA

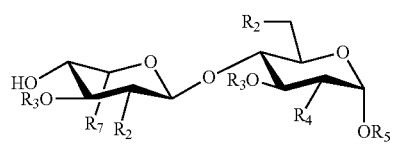

Formula BA wherein $R_2$ is —OAcetyl or —OBenzoyl, $R_3$ is benzyl, $R_4$ is $N_3$ (azide), $R_5$ is methyl and $R_7$ is —CO$_2$Me.

In one embodiment of this aspect, the process further includes converting the resulting product to fondaparinux sodium.

In yet another aspect, the present invention relates to a process for preparing a compound of Formula I:

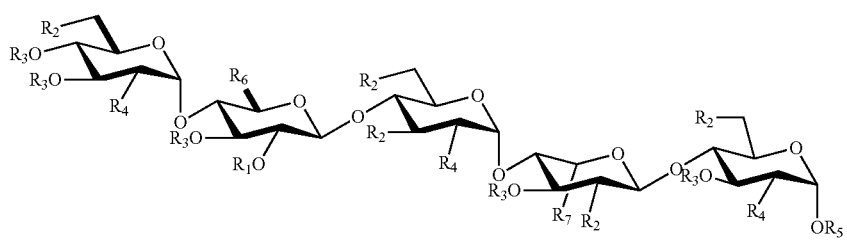

Formula I wherein
$R_1$ is H, levulinyl (Lev) or tetrahydropyran (THP);
$R_2$ is —O$^-$ or a salt thereof, —OH, —OAcyl, or —OSO$_3^-$ or a salt thereof;
$R_3$ is H, benzyl or a protecting group removable by hydrogenation;

$R_4$ is $N_3$ (azide), NH$_2$, NH-protecting group (i.e., —NH—R where R is an amino protecting group), or NHSO$_3^-$ or a salt thereof (e.g., NHSO$_3$Na, NHSO$_3$Li, NHSO$_3$K, and NHSO$_3$NH$_4$);

$R_5$ is $C_1$-$C_6$ alkyl; and $R_6$ and $R_7$ are independently selected from —CO$_2^-$ or a salt thereof, —CO$_2$H, and —CO$_2$R$_x$ (where R$_x$ is a $C_1$-$C_6$ alkyl, aryl, $C_1$-$C_4$ alkoxy(aryl), aryl($C_1$-$C_6$ alkyl), or $C_1$-$C_4$ alkoxy (aryl)($C_1$-$C_6$ alkyl)) (e.g., —CO$_2$Me, —CO$_2$CH$_2$C$_6$H$_5$ and —CO$_2$CH$_2$C$_6$H$_4$OMe); and wherein said compound has alpha (α) stereochemistry at the carbon bearing the —OR$_5$ group;

said process including linking a compound of Formula II:

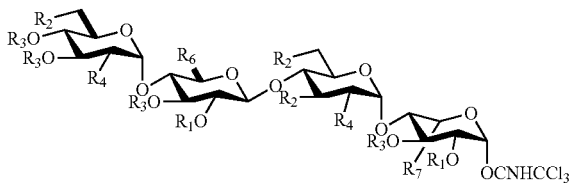

Formula II wherein,
$R_1$ is H, levulinyl (Lev) or tetrahydropyran (THP);
$R_2$ is —O$^-$ or a salt thereof, —OH, —OAcyl, —OSO$_3^-$ or a salt thereof;
$R_3$ is H, benzyl or a protecting group removable by hydrogenation;
$R_4$ is $N_3$ (azide), NH$_2$, NH-protecting group (i.e., —NH—R where R is an amino protecting group), or NHSO$_3^-$ or a salt thereof (e.g., NHSO$_3$Na, NHSO$_3$Li, NHSO$_3$K, and NHSO$_3$NH$_4$);

$R_6$ and $R_7$ are independently selected from —CO$_2^-$ or a salt thereof, —CO$_2$H, and —CO$_2$R$_x$ (where R$_x$ is a $C_1$-$C_6$ alkyl, aryl, $C_1$-$C_4$ alkoxy(aryl), aryl($C_1$-$C_6$ alkyl), or $C_1$-$C_4$ alkoxy (aryl)($C_1$-$C_6$ alkyl)) (e.g., —CO$_2$Me, —CO$_2$CH$_2$C$_6$H$_5$ and —CO$_2$CH$_2$C$_6$H$_4$OMe); and $R_9$ is $R_1$ or $R_2$, with a compound of Formula III

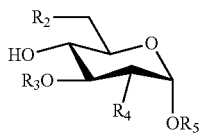

Formula III wherein
$R_2$ is —O⁻ or a salt thereof, —OH, —OAcyl, —OSO₃⁻ or a salt thereof;
$R_3$ is H, benzyl or a protecting group removable by hydrogenation;
$R_4$ is $N_3$ (azide), $NH_2$, NH-protecting group (i.e., —NH—R where R is an amino protecting group), or $NHSO_3^-$ or a salt thereof (e.g., $NHSO_3Na$, $NHSO_3Li$, $NHSO_3K$, and $NHSO_3NH_4$);
$R_5$ is $C_1$-$C_6$ alkyl.

In certain embodiments of this aspect, the compound of Formula II is wherein,
$R_1$ is H, levulinyl (Lev) or tetrahydropyran (THP);
$R_2$ is —O⁻ or a salt thereof, —OH, —OAcyl, or —OSO₃⁻ or a salt thereof;
$R_3$ is H, benzyl or a protecting group removable by hydrogenation;
$R_4$ is $N_3$ (azide), $NH_2$, NH-protecting group (i.e., —NH—R where R is an amino protecting group), or $NHSO_3^-$ or a salt thereof (e.g., $NHSO_3Na$, $NHSO_3Li$, $NHSO_3K$, and $NHSO_3NH_4$);
$R_5$ is $C_1$-$C_6$ alkyl; and
$R_6$ and $R_7$ are independently selected from —CO₂⁻ or a salt thereof, —CO₂H, and —CO₂$R_x$ (where $R_x$ is a $C_1$-$C_6$ alkyl, aryl, $C_1$-$C_4$ alkoxy(aryl), aryl($C_1$-$C_6$ alkyl), or $C_1$-$C_4$ alkoxy(aryl)($C_1$-$C_6$ alkyl)) (e.g., —CO₂Me, —CO₂CH₂C₆H₅ and —CO₂CH₂C₆H₄OMe); and wherein said compound has alpha (α) stereochemistry at the carbon bearing the —OR₅ group;

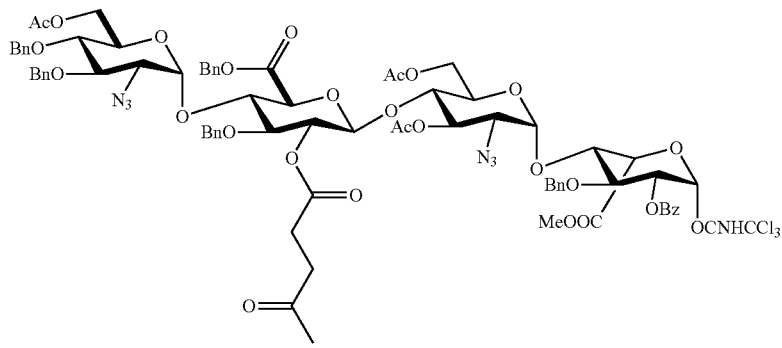

and the compound of Formula III is

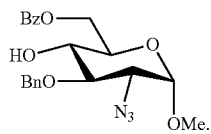

In yet another aspect, the present invention relates to a process for preparing a compound of Formula I:

the process including linking a compound of Formula IV:

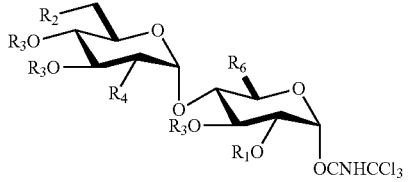

Formula IV

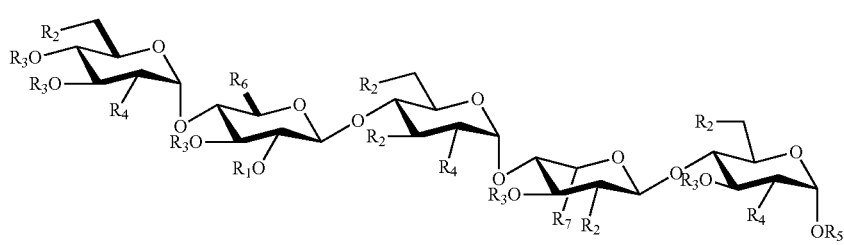

Formula I wherein, $R_1$ is H, levulinyl (Lev) or tetrahydropyran (THP);

$R_2$ is —O⁻ or a salt thereof, —OH, —OAcyl, —OSO₃⁻ or a salt thereof;

$R_3$ is H, benzyl or a protecting group removable by hydrogenation;

$R_4$ is $N_3$ (azide), $NH_2$, NH-protecting group (i.e., —NH—R where R is an amino protecting group), or $NHSO_3^-$ or a salt thereof (e.g., $NHSO_3Na$, $NHSO_3Li$, $NHSO_3K$, and $NHSO_3NH_4$); and $R_6$ is selected from —$CO_2^-$ or a salt thereof, —$CO_2H$, and —$CO_2R_x$ (where $R_x$ is a $C_1$-$C_6$ alkyl, aryl, $C_1$-$C_4$ alkoxy(aryl), aryl($C_1$-$C_6$ alkyl), or $C_1$-$C_4$ alkoxy(aryl)($C_1$-$C_6$ alkyl)) (e.g., —$CO_2Me$, —$CO_2CH_2C_6H_5$ and —$CO_2CH_2C_6H_4OMe$), with a compound of Formula V:

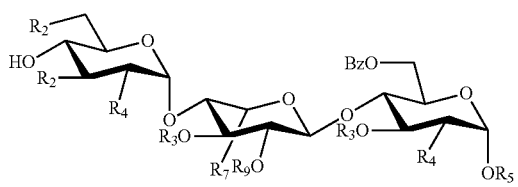

Formula V wherein, $R_1$ is H, levulinyl (Lev) or tetrahydropyran (THP);

$R_2$ is —O⁻ or a salt thereof, —OH, —OAcyl, —OSO₃⁻ or a salt thereof;

$R_3$ is H, benzyl or a protecting group removable by hydrogenation;

$R_4$ is $N_3$ (azide), $NH_2$, NH-protecting group (i.e., —NH-R where R is an amino protecting group), or $NHSO_3^-$ or a salt thereof (e.g., $NHSO_3Na$, $NHSO_3Li$, $NHSO_3K$, and $NHSO_3NH_4$);

$R_5$ is $C_1$-$C_6$ alkyl; and $R_7$ is selected from —$CO_2^-$ or a salt thereof, —$CO_2H$, and —$CO_2R_x$ (where $R_x$ is a $C_1$-$C_6$ alkyl, aryl, $C_1$-$C_4$ alkoxy(aryl), aryl($C_1$-$C_6$ alkyl), or $C_1$-$C_4$ alkoxy(aryl)($C_1$-$C_6$ alkyl)) (e.g., —$CO_2Me$, —$CO_2CH_2C_6H_5$ and —$CO_2CH_2C_6H_4OMe$); and $R_9$ is $R_1$ or $R_2$.

In certain embodiments of this aspect, the compound of Formula IV is

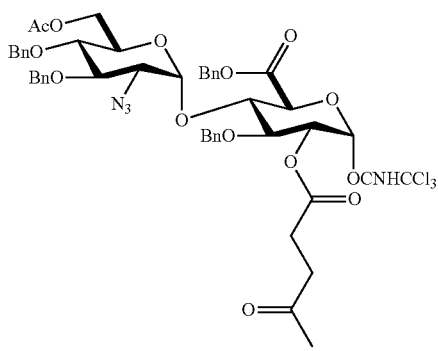

and the compound of Formula V is

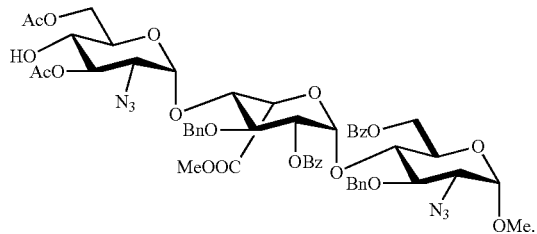

In another aspect, the present invention relates to a process for preparing a compound of Formula I wherein $R_1$ is tetrahydropyran (THP), $R_2$ is —OAcetyl or —OBenzoyl, $R_3$ is benzyl, $R_4$ is $N_3$ (azide), $R_5$ is methyl, $R_6$ is —$CO_2CH_2C_6H_5$ and $R_7$ is —$CO_2Me$, the process including:

(a) deprotecting a compound of Formula I wherein $R_1$ is levulinyl (Lev), $R_2$ is —OAcetyl or —OBenzoyl, $R_3$ is benzyl, $R_4$ is $N_3$ (azide), $R_5$ is methyl, $R_6$ is —$CO_2CH_2C_6H_5$ and $R_7$ is —$CO_2Me$ to afford a compound of Formula I wherein $R_1$ is H, $R_2$ is —OAcetyl or —OBenzoyl, $R_3$ is benzyl, $R_4$ is $N_3$ (azide), $R_5$ is methyl, $R_6$ is —$CO_2CH_2C_6H_5$, and $R_7$ is —$CO_2Me$; and (b) THP protecting the product of step (a).

In one embodiment, deprotecting step (a) includes treatment with a reagent selected from hydrazine, hydrazine hydrate, hydrazine acetate and $R_8NH$—$NH_2$ where $R_8$ is aryl, heteroaryl or alkyl. In one embodiment deprotecting step (a) comprises treatment with hydrazine.

In one embodiment, protecting step (b) comprises treatment with dihyropyran or a dihydropyran derivative and an acid selected from camphor sulfonic acid (CSA), hydrochloric acid (HCl), p-toluenesulfonic acid (pTsOH) and Lewis acids. In one embodiment, protecting step (b) comprises treatment with dihyropyran and an acid selected from hydrochloric acid and p-toluenesulfonic acid.

In another aspect, the present invention relates to a process for preparing a compound of Formula I wherein $R_1$ is tetrahydropyran (THP), $R_2$ is —O⁻ or a salt thereof, $R_3$ is benzyl, $R_4$ is $N_3$ (azide), $R_5$ is methyl, and $R_6$ and $R_7$ are —$CO_2^-$ or a salt thereof, comprising hydrolyzing a compound of Formula I wherein $R_1$ is tetrahydropyran (THP), $R_2$ is —OAcetyl or —OBenzoyl, $R_3$ is benzyl, $R_4$ is $N_3$ (azide), $R_5$ is methyl, $R_6$ is —$CO_2CH_2C_6H_5$, and $R_7$ is —$CO_2Me$.

In another aspect, the present invention relates to a process for preparing a compound of Formula I wherein $R_1$ is tetrahydropyran (THP), $R_2$ is —$OSO_3^-$ or a salt thereof, $R_3$ is benzyl, $R_4$ is $N_3$ (azide), $R_5$ is methyl, and $R_6$ and $R_7$ are —$CO_2^-$ or a salt thereof, comprising sulfating a compound of Formula I wherein $R_1$ is tetrahydropyran (THP), $R_2$ is —O⁻ or a salt thereof, $R_3$ is benzyl, $R_4$ is $N_3$ (azide), $R_5$ is methyl, and $R_6$ and $R_7$ are —$CO_2^-$ or a salt thereof.

In another aspect, the present invention relates to a process for preparing a compound of Formula I wherein $R_1$ is tetrahydropyran (THP), $R_2$ is —$OSO_3^-$ or a salt thereof, $R_3$ is H, $R_4$ is $NH_2$, $R_5$ is methyl, and $R_6$ and $R_7$ are —$CO_2^-$ or a salt thereof, comprising the step of hydrogenating a compound of Formula I wherein $R_1$ is tetrahydropyran (THP), $R_2$ is —$OSO_3^-$ or a salt thereof, $R_3$ is benzyl, $R_4$ is $N_3$ (azide), $R_5$ is methyl, and $R_6$ and $R_7$ are —$CO_2^-$ or a salt thereof.

In another aspect, the present invention relates to a process for preparing a compound of Formula I wherein $R_1$ is tetrahydropyran (THP), $R_2$ is —$OSO_3Na$, $R_3$ is H, $R_4$ is $NHSO_3Na$, $R_5$ is methyl, and $R_6$ and $R_7$ are —$CO_2Na$, comprising the step of sulfating a compound of Formula I wherein $R_1$ is tetrahydropyran (THP), $R_2$ is —$OSO_3^-$ or a salt thereof, $R_3$ is H, $R_4$ is $NH_2$, $R_5$ is methyl, and $R_6$ and $R_7$ are —$CO_2^-$ or a salt thereof.

In a further aspect, the present invention relates to a process for making a compound of Formula I:

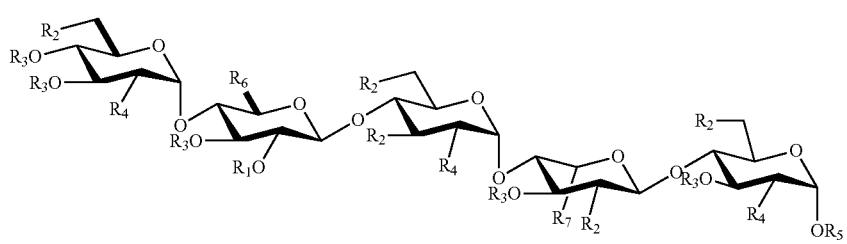

Formula I wherein $R_1$ is H, $R_2$ is —$OSO_3Na$, $R_3$ is H, $R_4$ is $NHSO_3Na$, $R_5$ is methyl, and $R_6$ and $R_7$ are —$CO_2Na$;

the process including deprotecting a compound of Formula I wherein $R_1$ is tetrahydropyran (THP), $R_2$ is —$OSO_3Na$, $R_3$ is H, $R_4$ is $NHSO_3Na$, $R_5$ is methyl, and $R_6$ and $R_7$ are —$CO_2Na$.

In yet a further aspect, the present invention relates to a process for making a compound of Formula 8:

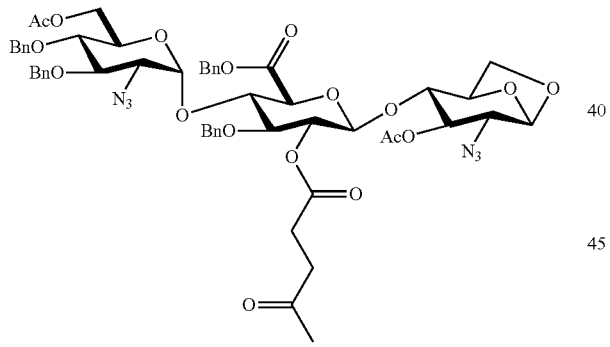

Formula 8 comprising reacting a compound of Formula 9:

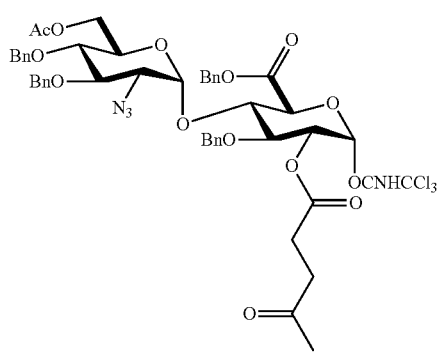

Formula 9 with a compound of Formula 10:

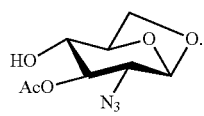

Formula 10

Fondaparinux Sodium

In a further aspect, the present invention relates to Fondaparinux, or a salt thereof (e.g., Fondaparinux sodium) containing a compound selected from P2, P3, P4, and combinations thereof.

Compound P2 (methylated nitrogen on the E ring):

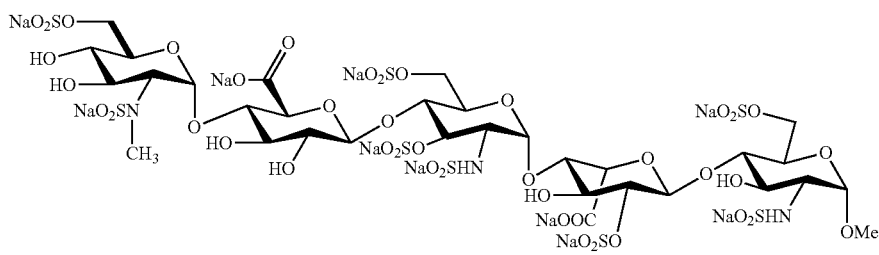

Compound P3 (methylated nitrogen on the A ring):

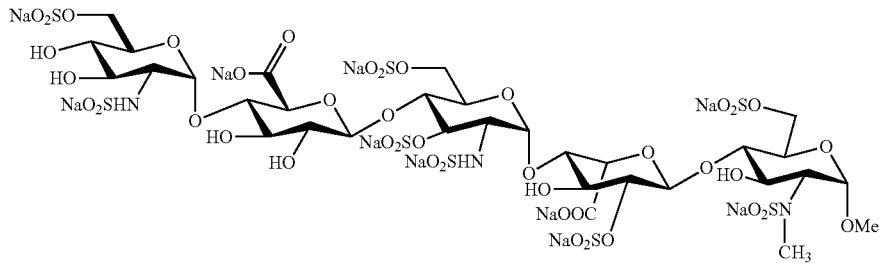

Compound P4 (N-formyl group on the C ring):

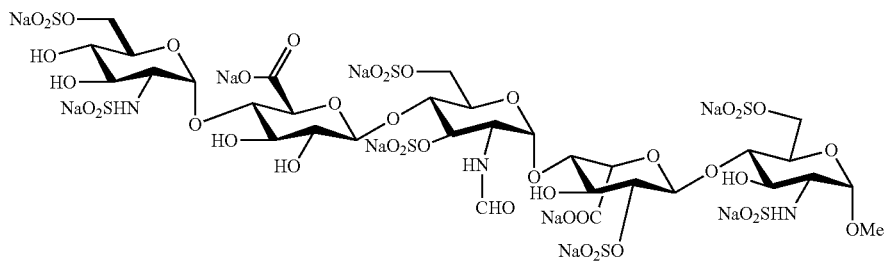

In additional embodiments, the present invention relates to a composition (such as a pharmaceutical composition) that includes Fondaparinux, or a salt thereof (e.g., Fondaparinux sodium) and a compound selected from P2, P3, P4, and combinations thereof.

In certain embodiments, the Fondaparinux, or a salt thereof (e.g., Fondaparinux sodium), or composition contains at least 90, 95, 98, 99 or 99.5% Fondaparinux, or salt thereof, based on the total weight of Fondaparinux or composition.

In certain embodiments, Compound P2 is present in an amount of greater than 0% and less than about 0.5%, such as greater than 0% and less than about 0.4%, greater than 0% and less than about 0.3%, greater than 0% and less than about 0.2% and greater than 0% and less than about 0.1%, based on the total weight of Fondaparinux or composition.

In certain embodiments, Compound P3 is present in an amount of greater than 0% and less than about 0.5%, such as greater than 0% and less than about 0.4%, greater than 0% and less than about 0.3%, greater than 0% and less than about 0.2% and greater than 0% and less than about 0.1%, based on the total weight of Fondaparinux or composition.

In certain embodiments, Compound P4 is present in an amount of greater than 0% and less than about 0.5%, such as greater than 0% and less than about 0.4%, greater than 0% and less than about 0.3%, greater than 0% and less than about 0.2% and greater than 0% and less than about 0.1%, based on the total weight of Fondaparinux or composition.

In additional embodiments, the Fondaparinux, or a salt thereof (e.g., Fondaparinux sodium) (or composition that includes Fondaparinux, or a salt thereof (e.g., Fondaparinux sodium)) may also contain Compound P1 (in addition to containing a compound selected from P2, P3, P4, and combinations thereof).

Compound P1 (beta-anomer of Fondaparinux sodium)

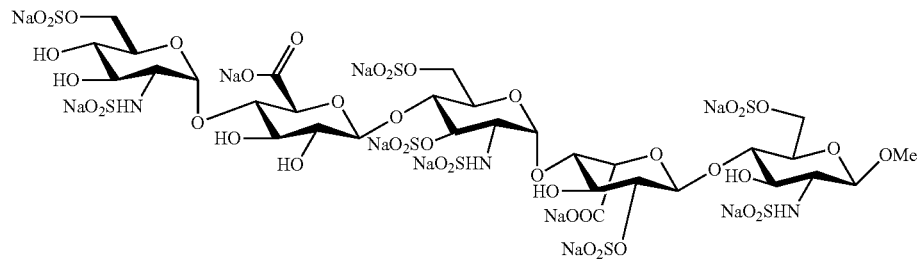

In certain embodiments, Compound P1 is present in an amount of greater than 0% and less than about 0.5%, such as greater than 0% and less than about 0.4%, greater than 0% and less than about 0.3%, greater than 0% and less than about 0.2% and greater than 0% and less than about 0.1%, based on the total weight of Fondaparinux or composition.

In additional embodiments, the present invention relates to a composition (such as a pharmaceutical composition) that includes Fondaparinux or a salt thereof (e.g., Fondaparinux sodium) and one or more tetrahydropyran protected pentasaccharides. In additional embodiments, the tetrahydropyran protected pentasaccharide is any of the tetrahydropyran protected pentasaccharides as described in any of the embodiments herein.

In certain embodiments, the tetrahydropyran protected pentasaccharide is present in an amount of greater than 0% and less than about 0.5%, such as greater than 0% and less than about 0.4%, greater than 0% and less than about 0.3%, greater than 0% and less than about 0.2%, greater than 0% and less than about 0.1%, based on the total weight of Fondaparinux or composition.

Any of the aforementioned forms of Fondaparinux (or a salt thereof) or compositions containing Fondaparinux (or a salt thereof) may be administered (e.g., 2.5 mg, 5 mg, 7.5 mg, 10 mg, solution for injection) for the prophylaxis of deep vein thrombosis (DVT) which may lead to pulmonary embolism (PE) in patients undergoing (i) hip fracture surgery (including extended prophylaxis), (ii) hip replacement surgery, (iii) knee replacement surgery and (iv) abdominal surgery (who are at risk for thromboembolic complications). The forms and compositions described herein may also be administered in conjunction with wafarin sodium for the treatment of acute DVT and PE.

Definitions

Examples of alkyl groups having one to six carbon atoms, are methyl, ethyl, propyl, butyl, pentyl, hexyl, and all isomeric forms and straight and branched thereof.

The term "acyl" unless otherwise defined refers to the chemical group —C(O)R. R can be, for example, aryl (e.g., phenyl) or alkyl (e.g., $C_1$-$C_6$ alkyl).

The term "aryl" refers to an aromatic group having 6 to 14 carbon atoms such as, for example, phenyl, naphthyl, tetrahydronapthyl, indanyl, and biphenyl. The term "heteroaryl" refers to an aromatic group having 5 to 14 atoms where at least one of the carbons has been replaced by N, O or S. Suitable examples include, for example, pyridyl, quinolinyl, dihydroquinolinyl, isoquinolinyl, quinazolinyl, dihydroquinazolyl, and tetrahydroquinazolyl.

It will be apparent to those skilled in the art that sensitive functional groups may need to be protected and deprotected during synthesis of a compound of the invention. This may be achieved by conventional methods, for example as described in "Protective Groups in Organic Synthesis" by Greene and Wuts, John Wiley & Sons Inc (1999), and references therein which can be added or removed using the procedures set forth therein. Examples of protected hydroxyl groups (i.e., hydroxyl protecting groups) include silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to, methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoroacetate. Examples of protected amine groups (i.e., amino protecting groups) include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and the like.

A protecting group that can be removed by hydrogenation is, by way of example, benzyl or a substituted benzyl group, for example benzyl ethers, benzylidene acetals. While the benzyl group itself is a commonly used protecting group that can be removed by hydrogenation, one example of a substituted benzyl protecting group is p-methoxy benzyl.

A number of hydrazine and hydrazine derivative are available for the deprotection (removal) of tetrahydropyran (THP) protecting group, including, but not limited to, hydrazine [$NH_2$—$NH_2$], hydrazine hydrate [$NH_2$—$NH_2 \cdot H_2O$] and hydrazine acetate [$NH_2$—$NH_2$.AcOH] and alkyl and aryl hydrazine derivatives such as $R_8NH$—$NH_2$ where $R_8$ is aryl, heteroaryl or alkyl.

Lewis acids known in the art include, for example, magnesium chloride, aluminum chloride, zinc chloride, boron trifluoride dimethyl etherate, titanium(IV) chloride and ferric chloride.

Throughout the description and claims of this specification the word "comprise" and other forms of the word, such as "comprising" and "comprises," means including but not limited to, and is not intended to exclude, for example, other additives, components, integers, or steps.

As used in the specification and the appended claims, the singular forms "a," "an" and "the" include plural referents unless the context clearly dictates otherwise. Thus, for example, reference to "a component" includes mixtures of two or more components.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

The following examples are merely illustrative of the present invention and should not be construed as limiting the scope of the invention in any way as many variations and equivalents that are encompassed by the present invention will become apparent to those skilled in the art upon reading the present disclosure.

EXAMPLES

In the synthesis of Fondaparinux sodium, the monomers A2, B1, C, D and E described herein may be made either by processes described in the art or, e.g., in the case of the D monomer, by a process as described herein. The B1 and A2 monomers may then linked to form a disaccharide, BA dimer. The E, D and C monomers may be linked to form a trisaccharide, EDC trimer. The EDC trimer may be derivatized to form an intermediate suitable for coupling with the BA dimer, thereby forming a pentasaccharides (EDCBA) pentamer. The EDCBA pentamer is an intermediate that may be converted through a series of reactions to Fondaparinux sodium. This strategy described herein provides an efficient method for multi kilograms preparation of Fondaparinux in high yields and high stereoselectivity.

Synthetic Procedures

The following abbreviations are used herein: Ac is acetyl; ACN is acetonitrile; MS is molecular sieves; DMF is dimethyl formamide; PMB is p-methoxybenzyl; Bn is benzyl; DCM is dichloromethane; THF is tetrahydrofuran; TFA is trifluoro acetic acid; CSA is camphor sulfonic acid; TEA is triethylamine; MeOH is methanol; DMAP is dimethylaminopyridine; RT is room temperature; CAN is ceric ammonium nitrate; $Ac_2O$ is acetic anhydride; HBr is hydrogen bromide; TEMPO is tetramethylpiperidine-N-oxide; TBACl is tetrabutyl ammonium chloride; EtOAc is ethyl acetate; HOBT is hydroxybenzotriazole; DCC is dicyclohexylcarbodiimide; Lev is levunlinyl; TBDPS is tertiary-butyl diphenylsilyl; TCA is trichloroacetonitrile; O-TCA is O-trichloroacetimidate; $Lev_2O$ is levulinic anhydride; DIPEA is diisopropylethylamine; Bz is benzoyl; TBAF is tetrabutylammonium fluoride; DBU is diazabicycloundecane; $BF_3.Et_2O$ is boron trifluoride etherate; TMSI is trimethylsilyl iodide; TBAI is tetrabutylammonium iodide; TES-Tf is triethylsilyl trifluoromethanesulfonate (triethylsilyl triflate); DHP is dihydropyran; PTS is p-toluenesulfonic acid.

The monomers used in the processes described herein may be prepared as described in the art, or can be prepared using the methods described herein.

Monomer A-2

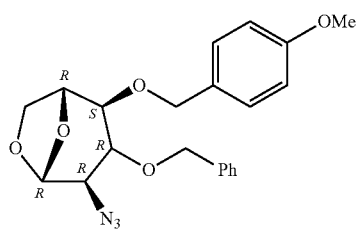

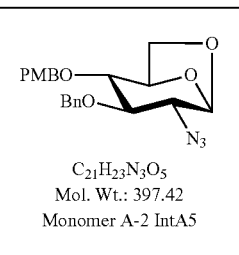

$C_{21}H_{23}N_3O_5$
Mol. Wt.: 397.42
Monomer A-2 IntA5

The synthesis of Monomer A-2 (CAS Registry Number 134221-42-4) has been described in the following references: Arndt et al., *Organic Letters*, 5(22), 4179-4182, 2003; Sakairi et al., *Bulletin of the Chemical Society of Japan*, 67(6), 1756-8, 1994; and Sakairi et al., *Journal of the Chemical Society, Chemical Communications*, (5), 289-90, 1991, and the references cited therein, which are hereby incorporated by reference in their entireties.

Monomer C

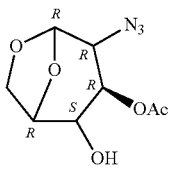

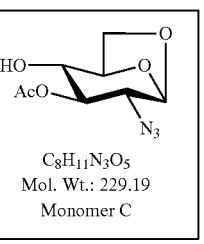

$C_8H_{11}N_3O_5$
Mol. Wt.: 229.19
Monomer C

Monomer C (CAS Registry Number 87326-68-9) can be synthesized using the methods described in the following references: Ganguli et al., *Tetrahedron: Asymmetry*, 16(2), 411-424, 2005; Izumi et al., *Journal of Organic Chemistry*, 62(4), 992-998, 1997; Van Boeckel et al., *Recueil: Journal of the Royal Netherlands Chemical Society*, 102(9), 415-16, 1983; Wessel et al., *Helvetica Chimica Acta*, 72(6), 1268-77, 1989; Petitou et al., U.S. Pat. No. 4,818,816 and references cited therein, which are hereby incorporated by reference in their entireties.

Monomer E

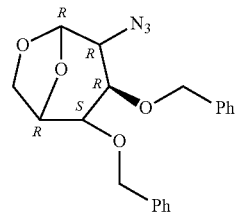

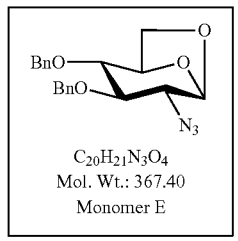

$C_{20}H_{21}N_3O_4$
Mol. Wt.: 367.40
Monomer E

Monomer E (CAS Registry Number 55682-48-9) can be synthesized using the methods described in the following literature references: Hawley et al., *European Journal of Organic Chemistry*, (12), 1925-1936, 2002; Dondoni et al., *Journal of Organic Chemistry*, 67(13), 4475-4486, 2002; Van der Klein et al., *Tetrahedron*, 48(22), 4649-58, 1992; Hori et al., *Journal of Organic Chemistry*, 54(6), 1346-53, 1989; Sakairi et al., *Bulletin of the Chemical Society of Japan*, 67(6), 1756-8, 1994; Tailler et al., *Journal of the Chemical Society, Perkin Transactions 1: Organic and Bio-Organic Chemistry*, (23), 3163-4, (1972-1999) (1992); Paulsen et al., *Chemische Berichte*, 111(6), 2334-47, 1978; Dasgupta et al., *Synthesis*, (8), 626-8, 1988; Paulsen et al., *Angewandte Chemie*, 87(15), 547-8, 1975; and references cited therein, which are hereby incorporated by reference in their entireties.

Monomer B-1

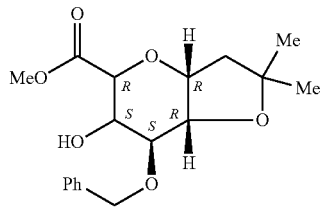

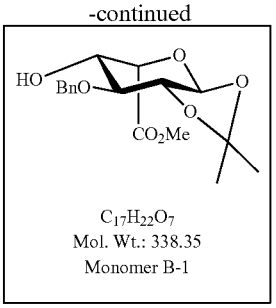

Monomer B-1 (CAS Registry Number 444118-44-9) can be synthesized using the methods described in the following literature references: Lohman et al., *Journal of Organic Chemistry*, 68(19), 7559-7561, 2003; Orgueira et al., *Chemistry—A European Journal*, 9(1), 140-169, 2003; Manabe et al., *Journal of the American Chemical Society*, 128(33), 10666-10667, 2006; Orgueira et al., *Angewandte Chemie, International Edition*, 41(12), 2128-2131, 2002; and references cited therein, which are hereby incorporated by reference in their entireties.

Synthesis of Monomer D

Monomer D was prepared in 8 synthetic steps from glucose pentaacetate using the following procedure:

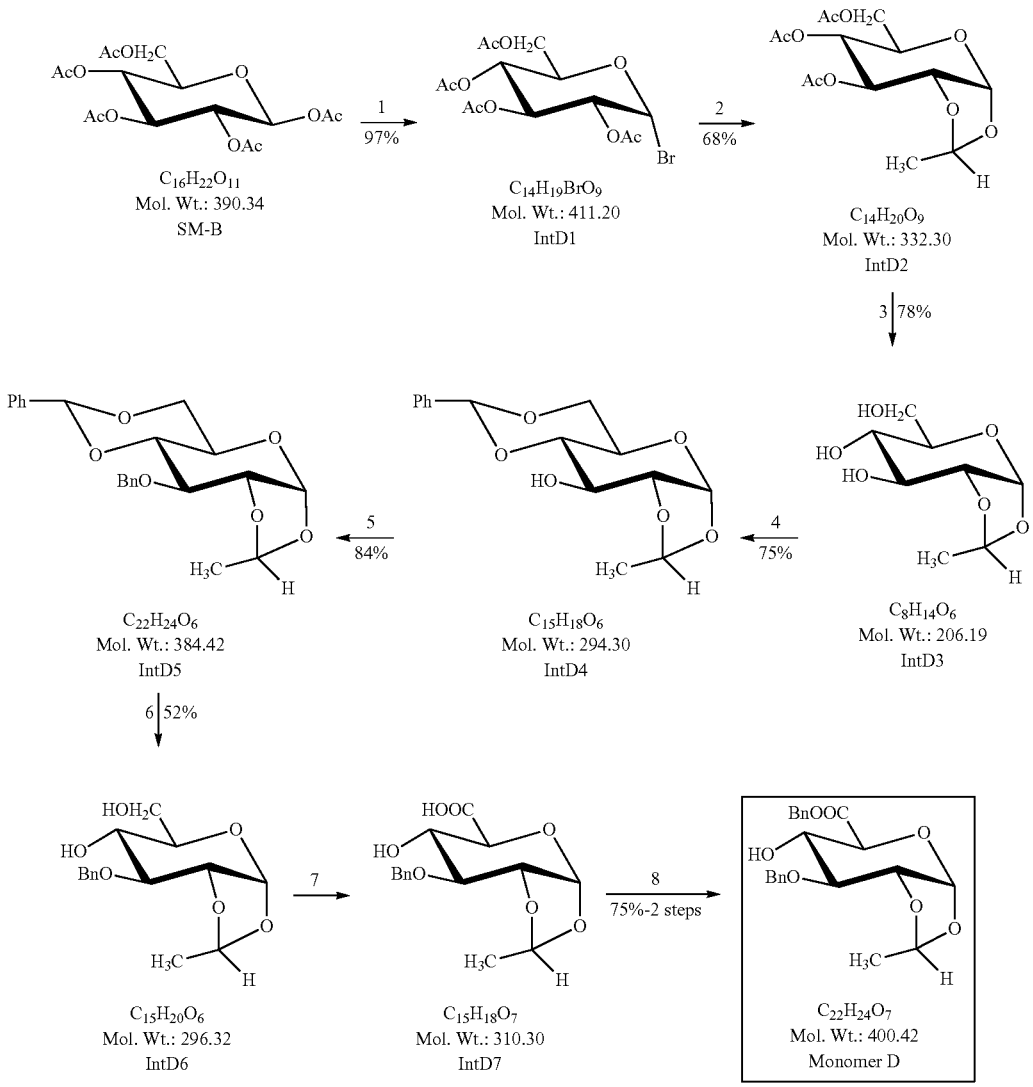

Reagents: 1. 33% HBr AcOH, DCM, 0° C. to RT, 3 hr; 2. NaBH$_4$, Bu$_4$NI, MS, ACN, 40° C., 16 h; 3. NaOMe, MeOH, 50° C., 3 h, 50wx resin; 4. PhCH(OMe)$_2$, CSA, 50° C., 2 h; 5. NaH, THF, BnBr, 0° C. to RT, 2 h; 6. TFA, THF, RT, 16 h; 7. TEMPO (2,3,6,6-tetramethyl-1-piperidine-N-oxide), TBACl, NaBr, EtOAc, NaClO, NaHCO3, RT, 16 h; 8. BnOH, HOBT, TEA, DCC, RT, 16 h.

Pentaacetate SM-B was brominated at the anomeric carbon using HBr in acetic acid to give bromide derivative IntD1. This step was carried out using the reactants SM-B, 33% hydrogen bromide, acetic acid and dichloromethane, stirring in an ice water bath for about 3 hours and evaporating at room temperature. IntD1 was reductively cyclized with sodium borohydride and tetrabutylammonium iodide in acetonitrile using 3 Å molecular sieves as dehydrating agent and stirring at 40° C. for 16 hours to give the acetal derivative, IntD2. The three acetyl groups in IntD2 were hydrolyzed by heating with sodium methoxide in methanol at 50° C. for 3 hours and the reaction mixture was neutralized using Dowex 50WX8-100 resin (Aldrich) in the acid form to give the trihydroxy acetal derivative IntD3.

The C4 and C6 hydroxyls of IntD3 were protected by mixing with benzaldehyde dimethyl acetate and camphor sulphonic acid at 50° C. for 2 hours to give the benzylidene-acetal derivative IntD4. The free hydroxyl at the C3 position of IntD4 was deprotonated with sodium hydride in THF as solvent at 0° C. and alkylated with benzyl bromide in THF, and allowing the reaction mixture to warm to room temperature with stirring to give the benzyl ether IntD5. The benzylidene moiety of IntD5 was deprotected by adding trifluoroacetic acid in dichloromethane at 0° C. and allowing it to warm to room temperature for 16 hours to give IntD6 with a primary hydroxyl group. IntD6 was then oxidized with TEMPO (2,2,6,6-tetramethyl-1-piperdine-N-oxide) in the presence of tetrabutylammonium chloride, sodium bromide, ethyl acetate, sodium chlorate and sodium bicarbonate, with stirring at room temperature for 16 hours to form the carboxylic acid derivative IntD7. The acid IntD7 was esterified with benzyl alcohol and dicyclohexylcarbodiimide (other reactants being hydroxybenzotriazole and triethylamine) with stirring at room temperature for 16 hours to give Monomer D.

Synthesis of the BA Dimer

The BA Dimer was prepared in 12 synthetic steps from Monomer B1 and Monomer A2 using the following procedure:

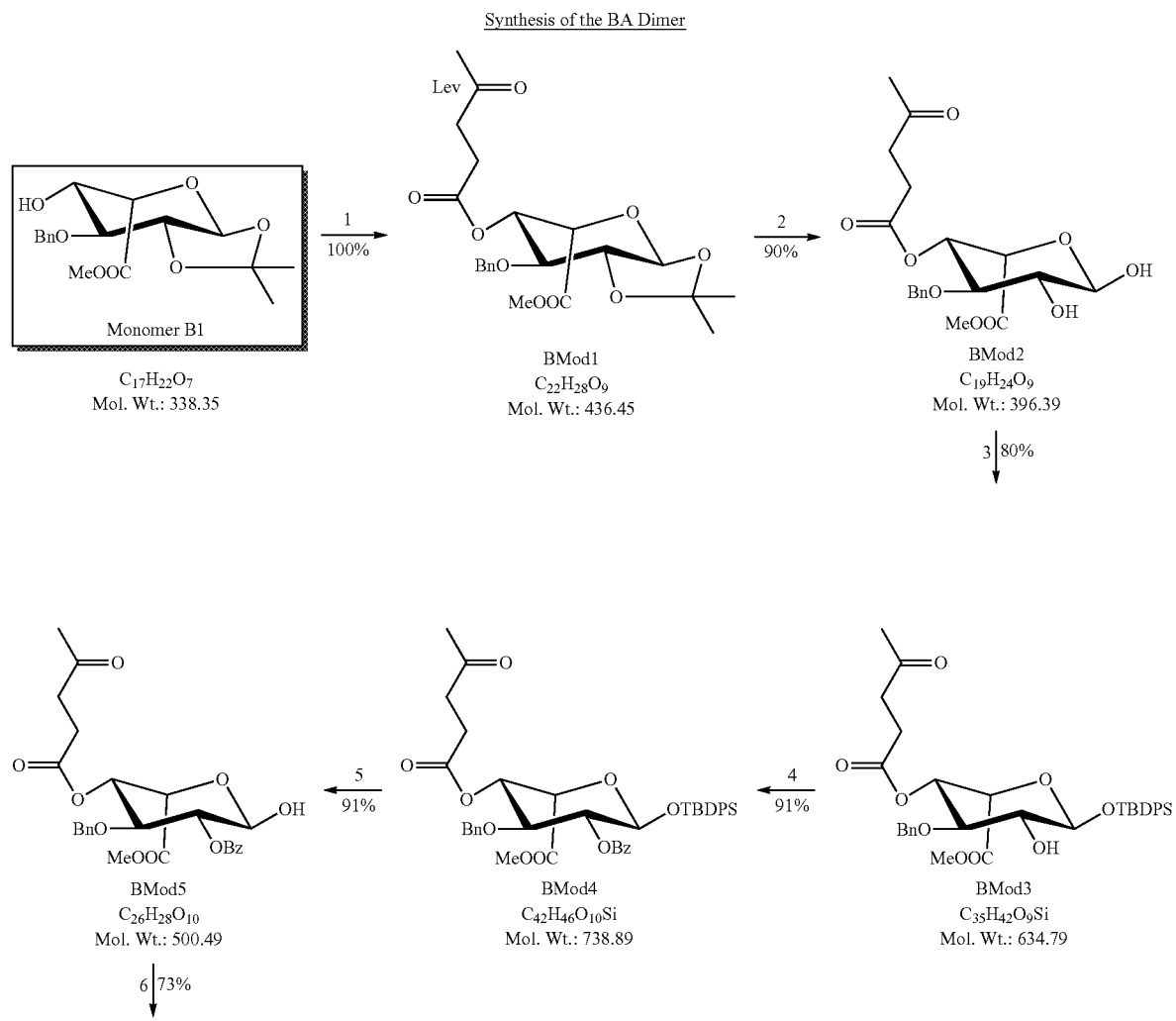

Synthesis of the BA Dimer

-continued

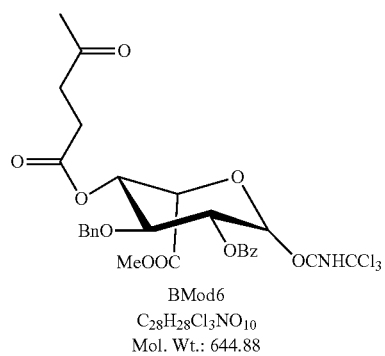
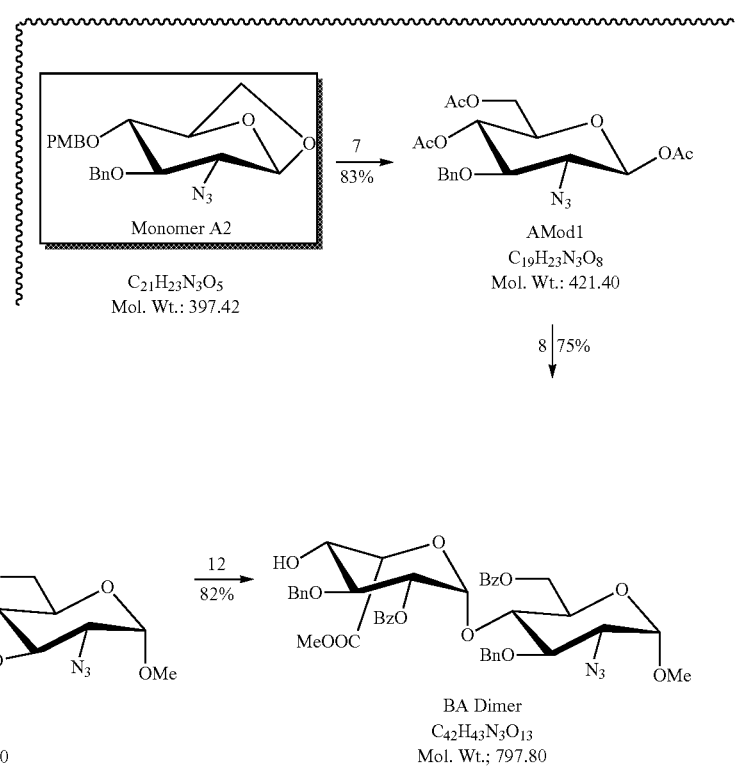

Reagents: 1. Lev₂O, DIPEA, RT, 16 h; 2. 90% TFA, RT, 4 h; 3. Imidazole, TBDPSi-Cl, RT, 3 h; 4. Pyridine, BzCl,
RT, 3 h; 5. TBAF, RT, 3 h; 6. TCA, DBU, RT, 2 h; 7. BF₃, Et₂O, Ac₂O, DCM, -20° C. to RT, 3 h; 8. (a) TMS-I, TBAI,
RT, 2 h; (b) DIPEA, MeOH, 16 h, RT; 9. NaOMe, Dowex 50WX8-100 resin H+ form, RT, 3 h; 10. Pyridine, Bz-Cl,
-40° C. to -10° C., 2 h; 11. BF₃•Et₂O, DMC, -20° C.-RT, 3 h; 12. NH₂NH₂•H₂O, RT, 3 h.

The C4-hydroxyl of Monomer B-1 was levulinated using levulinic anhydride and diisopropylethylamine (DIPEA) with mixing at room temperature for 16 hours to give the levulinate ester BMod1, which was followed by hydrolysis of the acetonide with 90% trifluoroacetic acid and mixing at room temperature for 4 hours to give the diol BMod2. The C1 hydroxyl of the diol BMod2 was silylated with tert-butyl-diphenylsilylchloride by mixing at room temperature for 3 hours to give silyl derivative BMod3. The C2-hydroxyl was then benzoylated with benzoyl chloride in pyridine, and mixed at room temperature for 3 hours to give compound BMod4. The silyl group on BMod4 was then deprotected with tert-butyl ammonium fluoride and mixing at room temperature for 3 hours to give the C1-hydroyl BMod5. The C1-hydroxyl is then allowed to react with trichloroacetonitrile in the presence of diazobicycloundecane (DBU) and mixing at room temperature for 2 hours to give the trichloroacetamidate (TCA) derivative BMod6, which suitable for coupling, for example with Monomer A-2.

Monomer A-2 was prepared for coupling by opening the anhydro moiety with BF₃.Et₂O followed by acetylation of the resulting hydroxyl groups to give the triacetate derivative AMod1.

Monomer A2 was prepared for the coupling reaction by opening the anhydro moiety and acetylation of the resulting hydroxyl groups to give the triacetate derivative AMod1. This transformation occurs using boron trifluoride etherate, acetic anhydride and dichloromethane, between −20° C. and room temperature for 3 hours. The C1-Acetate of AMod1 was then hydrolyzed and methylated in two steps to give the diacetate AMod3. That is, first AMod1 was reacted with trimethylsilyl iodide and mixed at room temperature for 2 hours, then reacted with and tetrabutyl ammonium iodide. This mixture was reacted with diisoproylethylamine and methanol and stirred for 16 hours at room temperature, thus forming AMod3. The C4 and C6 acetates of AMod3 are hydrolyzed with sodium methoxide to give the diol Amod4. The AMod3 mixture was also subjected to mixing at room temperature for 3 hours with Dowex 50 Wx4X8-100 resin in the acid form for neutralization. This formed Amod4. The C6-hydroxyl of AMod4 is then benzoylated by treating with benzoyl chloride in pyridine at −40° C. and then allowing it to warm up to −10° C. over 2 hours to give AMod5.

Coupling of monomer AMod5 with the free C4-hydroxyl group of BMod6 was performed in the presence of BF₃.Et₂O and dichloromethane with mixing between −20° C. and room temperature for 3 hours to provide disaccharide BA1. The C4-levulinyl moiety of the disaccharide was then hydrolyzed with hydrazine to give the BA Dimer, which is suitable for subsequent coupling reactions.

Synthesis of EDC Trimer

The EDC Trimer was prepared in 10 synthetic steps from Monomer E, Monomer D and Monomer C using the following procedure:

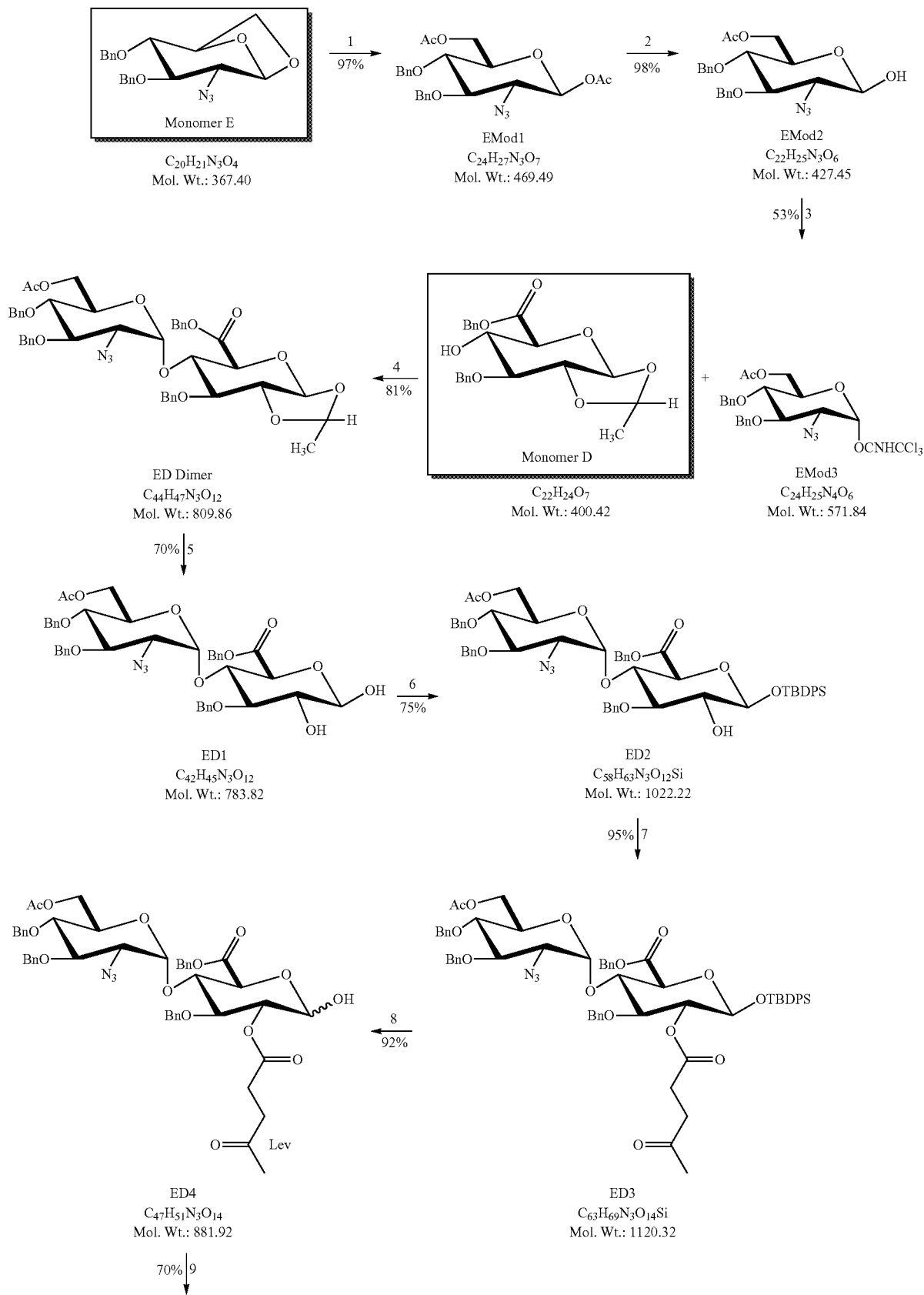

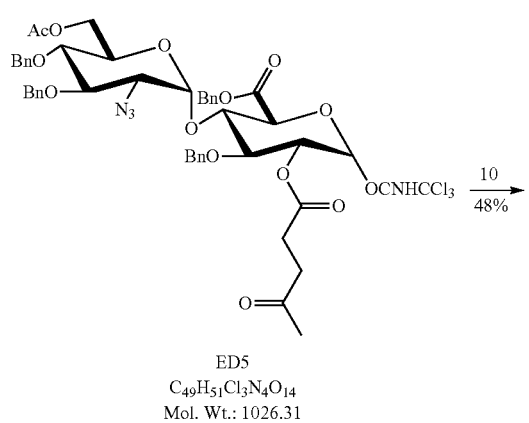

ED5
C$_{49}$H$_{51}$Cl$_{3}$N$_{4}$O$_{14}$
Mol. Wt.: 1026.31

+

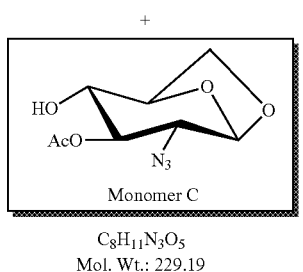

Monomer C

C$_{8}$H$_{11}$N$_{3}$O$_{5}$
Mol. Wt.: 229.19

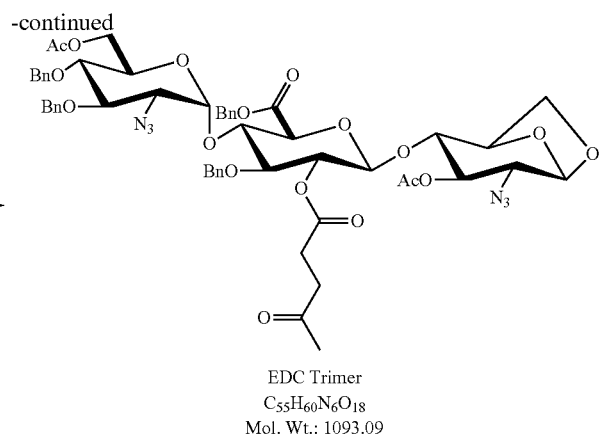

EDC Trimer
C$_{55}$H$_{60}$N$_{6}$O$_{18}$
Mol. Wt.: 1093.09

Reagents: 1. BF$_{3}$·Et$_{2}$O, Ac$_{2}$O, DCM, -10° C. to RT, 3 h; 2. NH$_{2}$NH$_{2}$·Ac, DMF, RT, 3 h; 3. TCA, DBU, DCM, RT, 2 h; 4. TES-Tf, -40° C., 2 h; 5. 90% TFA, -5° C. to RT, 4 h; 6. Imidazole, TBDPSi-Cl, -20° C. to RT, 4-6 h; 7. Lev$_{2}$O, DMAP, DIPEA, 16 h; 8. TBAF, AcOH, 0° C. to RT, 3 h; 9. TCA, DBU, DCM, RT, 2 h; 10. TES-Tf, -20° C., 2 h;

Monomer E was prepared for coupling by opening the anhydro moiety with BF$_{3}$.Et$_{2}$O followed by acetylation of the resulting hydroxyl groups to give diacetate EMod1. This occurs by the addition of Monomer E with boron trifluoride etherate, acetic anhydride and dichloromethane at −10° C., and allowing the reaction to warm to room temperature with stirring for 3 hours. The C1-Acetate of EMod1 is then hydrolyzed to give the alcohol, EMod2. This occurs by reacting Emod1 with hydrazine acetate and dimethylformamide and mixing at room temperature for 3 hours. The C1-hydroxyl of Emod2 is then reacted with trichloroacetonitrile to give the trichloro acetamidate (TCA) derivative EMod3 suitable for coupling, which reaction also employs diazabicycloundecane and dichloromethane and mixing at room temperature for 2 hours.

Monomer D, having a free C4-hydroxyl group, was coupled with monomer EMod3 in the presence of triethylsilyl triflate with mixing at −40° C. for 2 hours to give the disaccharide ED Dimer. The acetal on ring sugar D of the ED Dimer is hydrolyzed to give the C1,C2-diol ED1. This occurs by reacting the ED Dimer with 90% trifluoro acetic acid and mixing at room temperature for 4 hours. The C1-hydroxyl moiety of ED1 was then silylated with tert-butyldiphenylsilyl chloride to give the silyl derivative ED2. The C2-hydroxyl of ED2 was then allowed to react with levulinic anhydride in the presence of dimethylaminopyridine (DMAP) and diethylisopropylamine for approximately 16 hours to give the levulinate ester ED3. The TBDPS moiety is then deprotected by removal with tert-butylammonium fluoride in acetic acid with mixing at room temperature for 3 hours to give ED4 having a C1-hydroxyl. The C1-hydroxyl moiety of ED4 was then allowed to react with trichloroacetonitrile to give the TCA derivative ED5, which is suitable for coupling.

The C1-hydroxyl moiety of ED4 is then allowed to react with trichloroacetonitrile to give the TCA derivative ED5 suitable for coupling using diazabicycloundecane and dichloromethane, and mixing at room temperature for 2 hours. Monomer C, having a free C4-hydroxyl group, was then coupled with the disaccharide ED5 in the presence of triethylsilyl triflate and mixed at −20° C. for 2 hours to give the trisaccharide EDC Trimer.

Synthesis of the EDCBA Pentamer

The EDCBA Pentamer was prepared using the following procedure:

EDCBA Pentamer Synthesis-Part 1

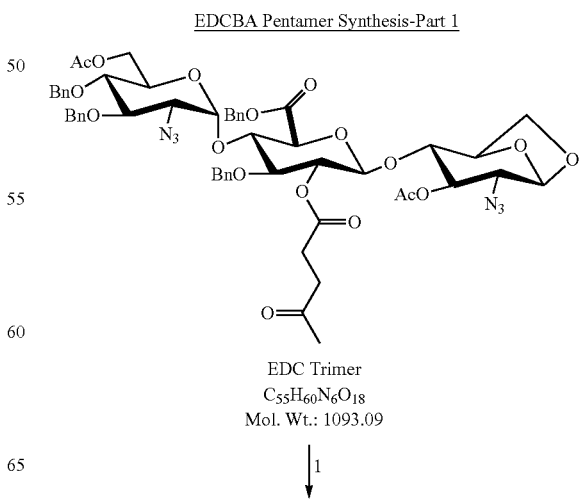

EDC Trimer
C$_{55}$H$_{60}$N$_{6}$O$_{18}$
Mol. Wt.: 1093.09

↓1

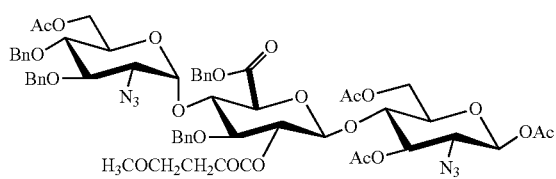

EDC-1
C$_{59}$H$_{66}$N$_6$O$_{21}$
Mol. Wt.: 1195.18

57% over 2 steps | 2

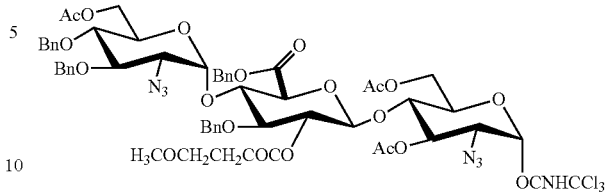

EDC-3
C$_{59}$H$_{64}$Cl$_3$N$_7$O$_{20}$
Mol. Wt.: 1297.53

Reagents: 1. BF$_3$•Et$_2$O, Ac$_2$O, DCM, -45 to -35° C., 3 h; 2. BnNH$_2$, THF, 10-15° C., 5-6 h; 3. TCA, DBU, DCM, -15 to -20° C., 2 h.

The preparation of EDCBA Pentamer is accomplished in two parts as follows. In part 1, the EDC Trimer, a diacetate intermediate, is prepared for the coupling reaction with Dimer BA by initially opening the anhydro moiety and acetylation of the resulting hydroxyl groups to give the tetraacetate derivative EDC1. This occurs by reacting the EDC Trimer with boron trifluoride etherate, acetic anhydride and dichloromethane and stirring between −10° C. and room temperature for 3 hours. The C1-Acetate of EDC1 is then hydrolyzed to give the alcohol, EDC2, by reacting EDC1 with benzylamine [BnNH$_2$] and tetrahydrofuran and mixing at −10° C. for 3 hours. The C1-hydroxyl of EDC2 is then reacted with trichloroacetonitrile and diazabicycloundecane, with mixing at room temperature for 2 hours, to give the trichloro acetamidate (TCA) derivative EDC3 suitable for coupling.

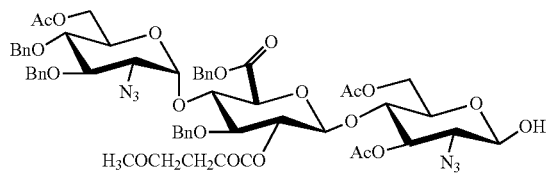

EDC-2
C$_{57}$H$_{64}$N$_6$O$_{20}$
Mol. Wt.: 1153.15

72% | 3

EDCBA Pentamer Synthesis-Part 2

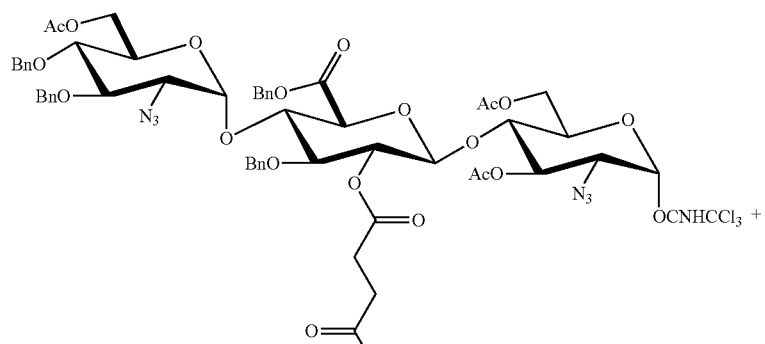

EDC-3
C$_{59}$H$_{64}$Cl$_3$N$_7$O$_{20}$
Mol. Wt.: 1297.53

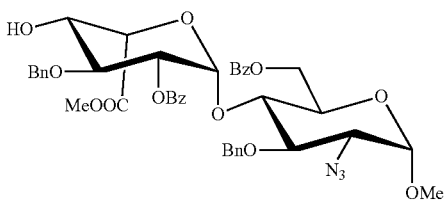

BA Dimer
C$_{42}$H$_{43}$N$_3$O$_{13}$
Mol. Wt.: 797.80 not isolated | 4

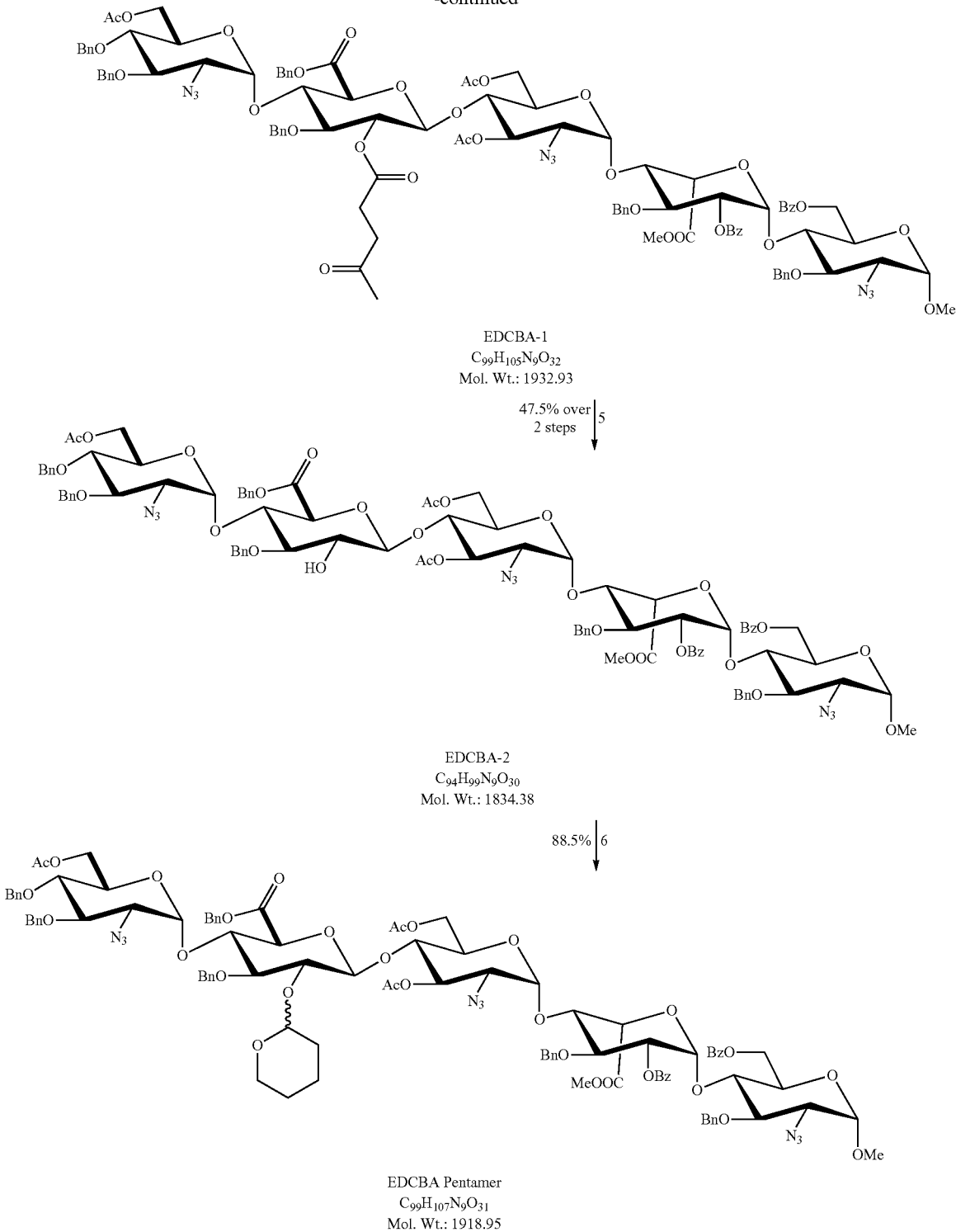

Reagents: 4. TES-Tf, DCM, -15 to -20° C., 3 h; 5. NH₂NH₂•Ac, NH₂NH₂•H₂O, MeOH, -25 to -20° C., 3 h; 6. DHP, CSA, DCE, 10 to 15° C. to RT, 3 h.

In Part 2 of the EDCBA Pentameter synthesis, the Dimer BA, having a free C4-hydroxyl group, is coupled with trisaccharide EDC3 in the presence of trimethylsilyltriflate at -30° C. mixing for 2 hours to give the pentasaccharide EDCBA1. The levulinyl ester on C2 of sugar D in EDCBA1 is hydrolyzed with a mixture of deprotecting agents, hydrazine hydrate and hydrazine acetate and stirring at room temperature for 3 hours to give the C2-hydroxyl containing intermediate EDCBA2. The C2-hydroxyl moiety on sugar D of EDCBA2 is then alkylated with dihydropyran (DHP) in the presence of camphor sulfonic acid (CSA) and tetrahydrofuran with mixing at room temperature for 3 hours to give the tetrahydropyranyl ether (THP) derivative, EDCBA Pentamer.

Synthesis of Fondaparinux

Fondaparinux was prepared using the following procedure:

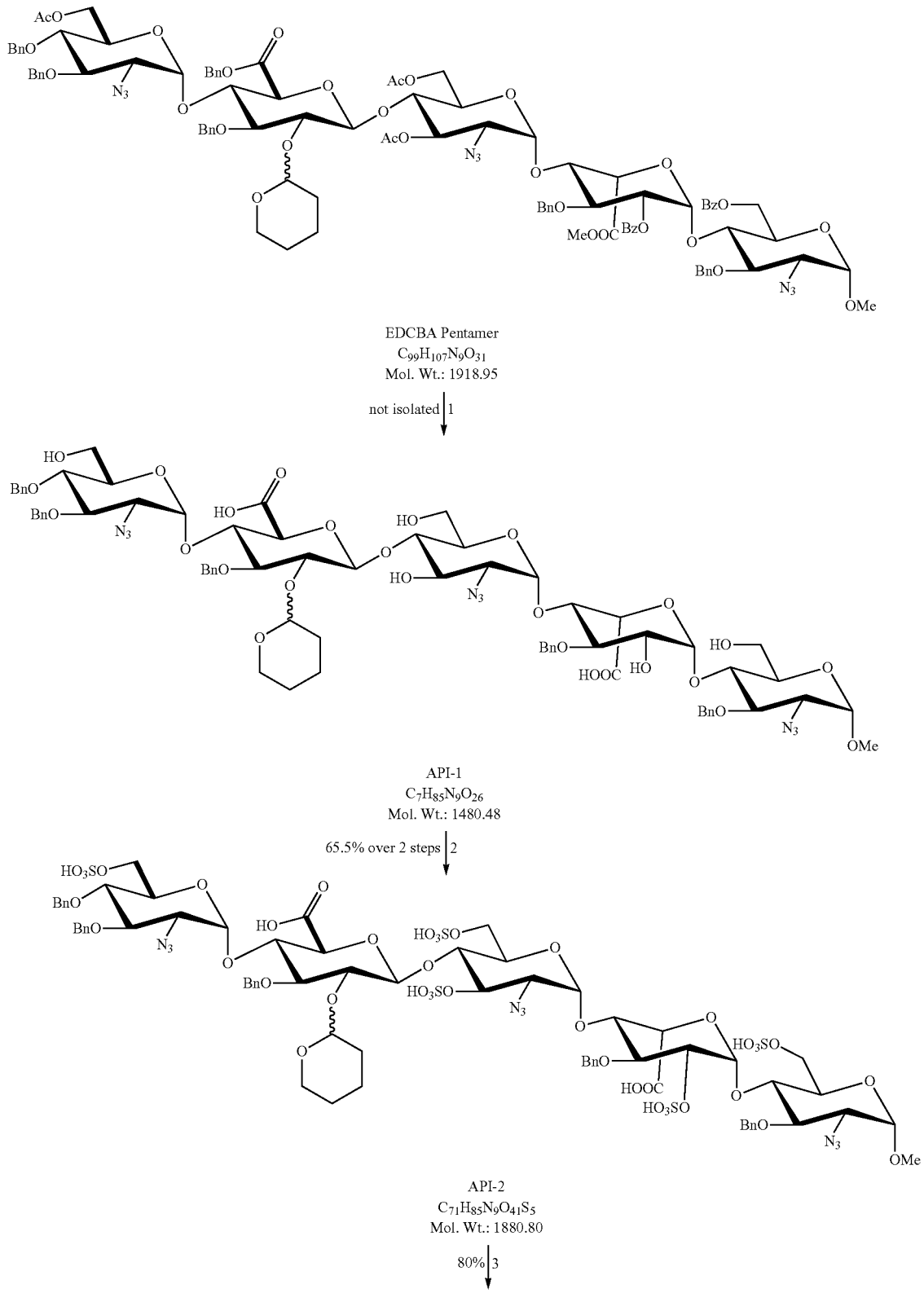

Fondaparinux API Scheme

EDCBA Pentamer
$C_{99}H_{107}N_9O_{31}$
Mol. Wt.: 1918.95 not isolated | 1

API-1
$C_7H_{85}N_9O_{26}$
Mol. Wt.: 1480.48

65.5% over 2 steps | 2

API-2
$C_{71}H_{85}N_9O_{41}S_5$
Mol. Wt.: 1880.80

80% | 3

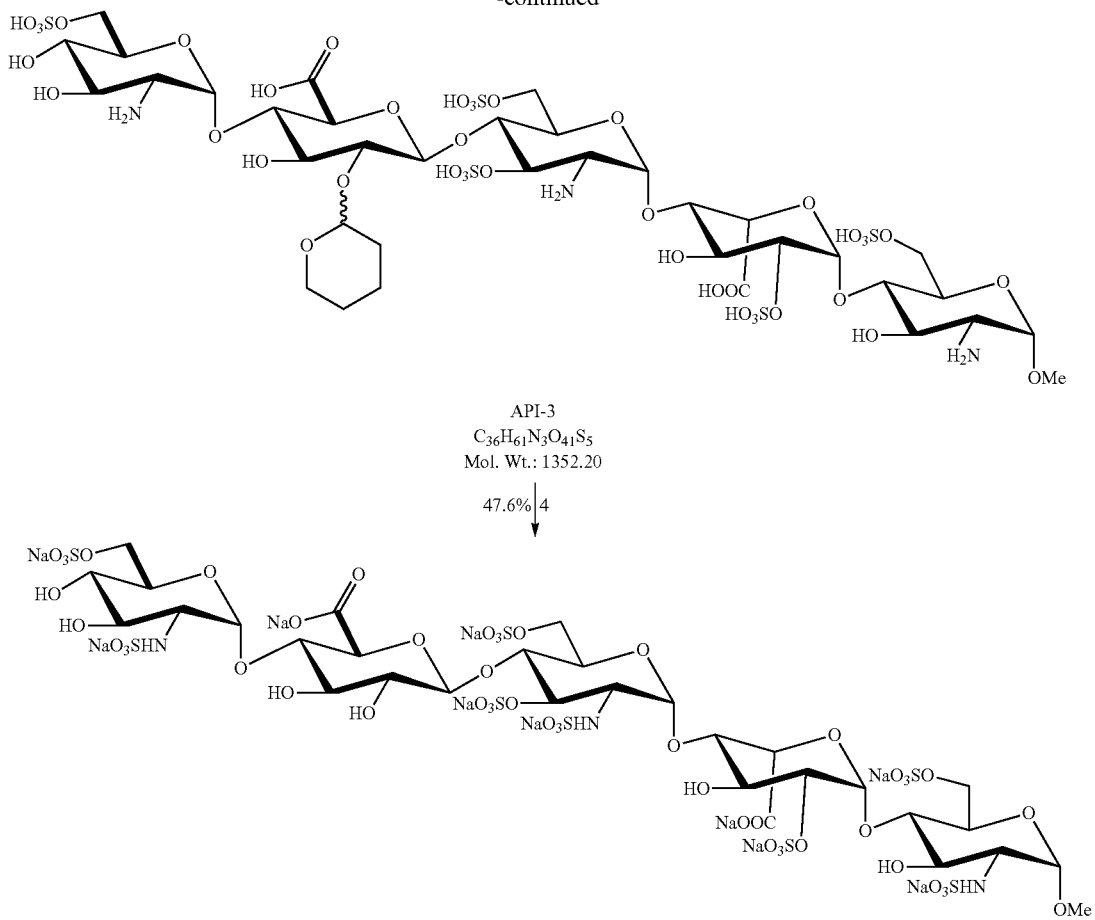

API-3
C₃₆H₆₁N₃O₄₁S₅
Mol. Wt.: 1352.20

47.6% | 4

FONDAPARINUX SODIUM
C₃₁H₄₃N₃Na₁₀O₄₉S₈
Mol. Wt.: 1728.09

Reagents: 1. NaOH, H₂O₂, LiOH, Dioxane, THF, RT, 34 h to 68 h; 2. Py•SO₃, DMF, Pyridine, 50° C., 2 h, CG-161 purification; 3. 10% Pd/C, H₂, MeOH, H2O, 60-65° C., 60 h; 4. (a) Py•SO₃, NaOH, NH₄OAc, RT, 12 h, (b) HiQ NH₄OAc/NaCl ion-exchange, Sephadex Desalt (c) Charcoal treatment and (d) HiQ NaCl ion-exchange, Sephadex Desalt.

The ester moieties in EDCBA Pentamer were hydrolyzed with sodium and lithium hydroxide in the presence of hydrogen peroxide in dioxane mixing at room temperature for 16 hours to give the pentasaccharide intermediate API1. The five hydroxyl moieties in API1 were sulfated using a pyridine-sulfur trioxide complex in dimethylformamide, mixing at 60° C. for 2 hours and then purified using column chromatography (CG-161), to give the pentasulfated pentasaccharide API2. The intermediate API2 was then hydrogenated to reduce the three azides on sugars E, C and A to amines and the reductive deprotection of the five benzyl ethers to their corresponding hydroxyl groups to form the intermediate API3. This transformation occurs by reacting API2 with 10% palladium/carbon catalyst with hydrogen gas for 72 hours. The three amines on API3 were then sulfated using the pyridine-sulfur trioxide complex in sodium hydroxide and ammonium acetate, allowing the reaction to proceed for 12 hours. The acidic work-up procedure of the reaction removes the THP group to provide crude fondaparinux which is purified and is subsequently converted to its salt form. The crude mixture was purified using an ion-exchange chromatographic column (HiQ resin) followed by desalting using a size exclusion resin or gel filtration (Biorad Sephadex G25) to give the final API, fondaparinux sodium Experimental Procedures Preparation of IntD1

Bromination of Glucose Pentaacetate

To a 500 ml flask was added 50 g of glucose pentaacetate (C₆H₂₂O₁₁) and 80 ml of methylene chloride. The mixture was stirred at ice-water bath for 20 min HBr in HOAc (33%, 50 ml) was added to the reaction mixture. After stirring for 2.5 hr another 5 ml of HBr was added to the mixture. After another 30 min, the mixture was added 600 ml of methylene chloride. The organic mixture was washed with cold water (200 ml×2), Saturated NaHCO₃(200 ml×2), water (200 ml) and brine (200 ml×2). The organic layer was dried over Na₂SO₄ and the mixture was evaporated at RT to give white solid as final product, bromide derivative, IntD1 (~95% yield). $C_{14}H_{19}BrO_9$, TLC $R_f$=0.49, $SiO_2$, 40% ethyl acetate/60% hexanes; Exact Mass 410.02.

Preparation of IntD2 by Reductive Cyclization

To a stirring mixture of bromide IntD1 (105 g), tetrabutylammonium iodide (60 g, 162 mmol) and activated 3 Å molecular sieves in anhydrous acetonitrile (2 L), solid $NaBH_4$ (30 g, 793 mmol) was added. The reaction was heated at 40° C. overnight. The mixture was then diluted with dichloromethane (2 L) and filtered through Celite®. After evaporation, the residue was dissolved in 500 ml ethyl acetate. The white solid ($Bu_4NI$ or $Bu_4NBr$) was filtered. The ethyl acetate solution was evaporated and purified by chromatography on silica gel using ethyl acetate and hexane as eluent to give the acetal-triacetate IntD2 (~60-70% yield). TLC $R_f$=0.36, $SiO_2$ in 40% ethyl acetate/60% hexanes.

Preparation of IntD3 by De-Acetylation

To a 1000 ml flask was added triacetate IntD2 (55 g) and 500 ml of methanol. After stirring 30 min, the reagent NaOMe (2.7 g, 0.3 eq) was added and the reaction was stirred overnight. Additional NaOMe (0.9 g) was added to the reaction mixture and heated to 50° C. for 3 hr. The mixture was neutralized with Dowex 50W×8 cation resin, filtered and evaporated. The residue was purified by silica gel column to give 24 g of trihydroxy-acetal IntD3. TLC $R_f$=0.36 in $SiO_2$, 10% methanol/90% ethyl acetate.

Preparation of IntD4 by Benzylidene Formation

To a 1000 ml flask was added trihydroxy compound IntD3 (76 g) and benzaldehyde dimethyl acetal (73 g, 1.3 eq). The mixture was stirred for 10 min, after which D(+)-camphorsulfonic acid (8.5 g, CSA) was added. The mixture was heated at 50° C. for two hours. The reaction mixture was then transferred to separatory funnel containing ethyl acetate (1.8 L) and sodium bicarbonate solution (600 ml). After separation, the organic layer was washed with a second sodium bicarbonate solution (300 ml) and brine (800 ml). The two sodium carbonate solutions were combined and extracted with ethyl acetate (600 ml×2). The organic mixture was evaporated and purified by silica gel column to give the benzylidene product IntD4 (77 g, 71% yield). TLC $R_f$=0.47, $SiO_2$ in 40% ethyl acetate/60% hexanes.

Preparation of IntD5 by Benzylation

To a 500 ml flask was added benzylidene acetal compound IntD4 (21 g,) in 70 ml THF. To another flask (1000 ml) was added NaH (2 eq). The solution of IntD4 was then transferred to the NaH solution at 0° C. The reaction mixture was stirred for 30 min, then benzyl bromide (16.1 ml, 1.9 eq) in 30 ml THF was added. After stirring for 30 min, DMF (90 ml) was added to the reaction mixture. Excess NaH was neutralized by careful addition of acetic acid (8 ml). The mixture was evaporated and purified by silica gel column to give the benzyl derivative IntD5. (23 g) TLC $R_f$=0.69, $SiO_2$ in 40% ethyl acetate/60% hexanes.

Preparation of IntD6 by Deprotection of Benzylidene

To a 500 ml flask was added the benzylidene-acetal compound IntD5 (20 g) and 250 ml of dichloromethane, the reaction mixture was cooled to 0° C. using an ice-water-salt bath. Aqueous TFA (80%, 34 ml) was added to the mixture and stirred over night. The mixture was evaporated and purified by silica gel column to give the dihydroxy derivative IntD6. (8 g, 52%). TLC $R_f$=0.79, $SiO_2$ in 10% methanol/90% ethyl acetate.

Preparation of IntD7 by Oxidation of 6-Hydroxyl

To a 5 L flask was added dihydroxy compound IntD6 (60 g), TEMPO (1.08 g), sodium bromide (4.2 g), tetrabutylammonium chloride (5.35 g), saturated $NaHCO_3$ (794 ml) and EtOAc (1338 ml). The mixture was stirred over an ice-water bath for 30 min To another flask was added a solution of NaOCl (677 ml), saturated $NaHCO_3$ (485 ml) and brine (794 ml). The second mixture was added slowly to the first mixture (over about two hrs). The resulting mixture was then stirred overnight. The mixture was separated, and the inorganic layer was extracted with EtOAc (800 ml×2). The combined organic layers were washed with brine (800 ml). Evaporation of the organic layer gave 64 g crude carboxylic acid product IntD7 which was used in the next step use without purification. TLC $R_f$=0.04, $SiO_2$ in 10% methanol/90% ethyl acetate.

Preparation of Monomer D by Benzylation of the Carboxylic Acid

To a solution of carboxylic acid derivative IntD7 (64 g) in 600 ml of dichloromethane, was added benzyl alcohol (30 g) and N-hydroxybenzotriazole (80 g, HOBt). After stirring for 10 min triethylamine (60.2 g) was added slowly. After stirring another 10 min, dicyclohexylcarbodiimide, (60.8 g, DCC) was added slowly and the mixture was stirred overnight. The reaction mixture was filtered and the solvent was removed under reduced pressure followed by chromatography on silica gel to provide 60.8 g (75%, over two steps) of product, Monomer D. TLC $R_f$=0.51, $SiO_2$ in 40% ethyl acetate/60% hexanes.

Synthesis of the BA Dimer

Step 1. Preparation of BMod1, Levulination of Monomer B1

A 100 L reactor was charged with 7.207 Kg of Monomer B1 (21.3 moles, 1 equiv), 20 L of dry tetrahydrofuran (THF) and agitated to dissolve. When clear, it was purged with nitrogen and 260 g of dimethylamino pyridine (DMAP, 2.13 moles, 0.1 equiv) and 11.05 L of diisopropylethylamine (DIPEA, 8.275 kg, 63.9 moles, 3 equiv) was charged into the reactor. The reactor was chilled to 10-15° C. and 13.7 kg levulinic anhydride (63.9 mol, 3 equiv) was transferred into the reactor. When the addition was complete, the reaction was warmed to ambient temperature and stirred overnight or 12-16 hours. Completeness of the reaction was monitored by TLC (40:60 ethyl acetate/hexane) and HPLC. When the reaction was complete, 20 L of 10% citric acid, 10 L of water and 25 L of ethyl acetate were transferred into the reactor. The mixture was stirred for 30 min and the layers were separated. The organic layer (EtOAc layer) was extracted with 20 L of water, 20 L 5% sodium bicarbonate and 20 L 25% brine solutions. The ethyl acetate solution was dried in 4-6 Kg of anhydrous sodium sulfate. The solution was evaporated to a syrup (bath temp. 40° C.) and dried overnight. The yield of the isolated syrup of BMod1 was 100%.

Synthesis of the BA Dimer

Step 2. Preparation of BMod2, TFA Hydrolysis of BMod1

A 100 L reactor was charged with 9296 Kg of 4-Lev Monomer B1 (BMod1) (21.3 mol, 1 equiv). The reactor chiller was turned to <5° C. and stirring was begun, after which 17.6 L of 90% TFA solution (TFA, 213 mole, 10 equiv) was transferred into the reactor. When the addition was complete, the reaction was monitored by TLC and HPLC. The reaction took approximately 2-3 hours to reach completion. When the reaction was complete, the reactor was chilled and 26.72 L of triethylamine (TEA, 19.4 Kg, 191.7 mole, 0.9 equiv) was transferred into the reactor. An additional 20 L of water and 20 L ethyl acetate were transferred into the reactor. This was stirred for 30 min and the layers were separated. The organic layer was extracted (EtOAc layer) with 20 L 5% sodium bicarbonate and 20 L 25% brine solutions. The ethyl acetate solution was dried in 4-6 Kg of anhydrous sodium sulfate. The solution was evaporated to a syrup (bath temp. 40° C.). The crude product was purified in a 200 L silica column using 140-200 L each of the following gradient profiles: 50:50, 80:20 (EtOAc/heptane), 100% EtOAc, 5:95, 10:90 (MeOH/EtOAc). The pure fractions were pooled and evaporated to a syrup. The yield of the isolated syrup, BMod2 was 90%.

Synthesis of the BA Dimer

Step 3. Preparation of BMod3, Silylation of BMod2

A 100 L reactor was charged with 6.755 Kg 4-Lev-1,2-DiOH Monomer B1 (BMod2) (17.04 mol, 1 equiv), 2328 g of imidazole (34.2 mol, 2 equiv) and 30 L of dichloromethane. The reactor was purged with nitrogen and chilled to −20° C., then 5.22 L tert-butyldiphenylchloro-silane (TBDPS-Cl, 5.607 Kg, 20.4 mol, 1.2 equiv) was transferred into the reactor. When addition was complete, the chiller was turned off and the reaction was allowed to warm to ambient temperature. The reaction was monitored by TLC (40% ethyl acetate/hexane) and HPLC. The reaction took approximately 3 hours to reach completion. When the reaction was complete, 20 L of water and 10 L of DCM were transferred into the reactor and stirred for 30 min, after which the layers were separated. The organic layer (DCM layer) was extracted with 20 L water and 20 L 25% brine solutions. Dichloromethane solution was dried in 4-6 Kg of anhydrous sodium sulfate. The solution was evaporated to a syrup (bath temp. 40° C.). The yield of BMod3 was about 80%.

Synthesis of the BA Dimer

Step 4. Preparation of BMod4, Benzoylation

A 100 L reactor was charged with 8.113 Kg of 4-Lev-1-Si-2-OH Monomer B1 (BMod3) (12.78 mol, 1 equiv), 9 L of pyridine and 30 L of dichloromethane. The reactor was purged with nitrogen and chilled to −20° C., after which 1.78 L of benzoyl chloride (2155 g, 15.34 mol, 1.2 equiv) was transferred into the reactor. When addition was complete, the reaction was allowed to warm to ambient temperature. The reaction was monitored by TLC (40% ethyl acetate/heptane) and HPLC. The reaction took approximately 3 hours to reach completion. When the reaction was complete, 20 L of water and 10 L of DCM were transferred into the reactor and stirred for 30 min, after which the layers were separated. The organic layer (DCM layer) was extracted with 20 L water and 20 L 25% brine solutions. The DCM solution was dried in 4-6 Kg of anhydrous sodium sulfate. The solution was evaporated to a syrup (bath temp. 40° C.). Isolated syrup BMod4 was obtained in 91% yield.

Synthesis of the BA Dimer

Step 5. Preparation of BMod5, Desilylation

A 100 L reactor was charged with 8.601 Kg of 4-Lev-1-Si-2-Bz Monomer B1 (BMod4) (11.64 mol, 1 equiv) in 30 L tetrahydrofuran. The reactor was purged with nitrogen and chilled to 0° C., after which 5.49 Kg of tetrabutylammonium fluoride (TBAF, 17.4 mol, 1.5 equiv) and 996 mL (1045 g, 17.4 mol, 1.5 equiv) of glacial acetic acid were transferred into the reactor. When the addition was complete, the reaction was stirred at ambient temperature. The reaction was monitored by TLC (40:60 ethyl acetate/hexane) and HPLC. The reaction took approximately 6 hours to reach completion. When the reaction was complete, 20 L of water and 10 L of DCM were transferred into the reactor and stirred for 30 min, after which the layers were separated. The organic layer (DCM layer) was extracted with 20 L water and 20 L 25% brine solutions. The dichloromethane solution was dried in 4-6 Kg of anhydrous sodium sulfate. The solution was evaporated to a syrup (bath temp. 40° C.). The crude product was purified in a 200 L silica column using 140-200 L each of the following gradient profiles: 10:90, 20:80, 30:70, 40:60, 50:50, 60:40, 70:30, 80:20 (EtOAc/heptane) and 200 L 100% EtOAc. Pure fractions were pooled and evaporated to a syrup. The intermediate BMod5 was isolated as a syrup in 91% yield.

Synthesis of the BA Dimer

Step 6: Preparation of BMod6, TCA Formation

A 100 L reactor was charged with 5.238 Kg of 4-Lev-1-OH-2-Bz Monomer B1 (BMod5) (10.44 mol, 1 equiv) in 30 L of DCM. The reactor was purged with nitrogen and chilled to 10-15° C., after which 780 mL of diazabicyclo undecene (DBU, 795 g, 5.22 mol, 0.5 equiv) and 10.47 L of trichloroacetonitrile (TCA, 15.08 Kg, 104.4 mol, 10 equiv) were transferred into the reactor. Stirring was continued and the reaction was kept under a nitrogen atmosphere. After reagent addition, the reaction was allowed to warm to ambient temperature. The reaction was monitored by HPLC and TLC (40:60 ethyl acetate/heptane). The reaction took approximately 2 hours to reach completion. When the reaction was complete, 20 L of water and 10 L of dichloromethane were transferred into the reactor. This was stirred for 30 min and the layers were separated. The organic layer (DCM layer) was separated with 20 L water and 20 L 25% brine solutions. The dichloromethane solution was dried in 4-6 Kg of anhydrous sodium sulfate. The solution was evaporated to a syrup (bath temp. 40° C.). The crude product was purified in a 200 L silica column using 140-200 L each of the following gradient profiles: 10:90, 20:80, 30:70, 40:60 and 50:50 (EtOAc/Heptane). Pure fractions were pooled and evaporated to a syrup. The isolated yield of BMod6 was 73%.

Synthesis of the BA Dimer

Step 7. Preparation of AMod1, Acetylation of Monomer A2

A 100 L reactor was charged with 6.772 Kg of Monomer A2 (17.04 mole, 1 eq.), 32.2 L (34.8 Kg, 340.8 moles, 20 eq.) of acetic anhydride and 32 L of dichloromethane. The reactor was purged with nitrogen and chilled to −20° C. When the temperature reached −20° C., 3.24 L (3.63 Kg, 25.68 mol, 1.5 equiv) of boron trifluoride etherate ($BF_3.Et_2O$) was transferred into the reactor. After complete addition of boron trifluoride etherate, the reaction was allowed to warm to room temperature. The completeness of the reaction was monitored by HPLC and TLC (30:70 ethyl acetate/heptane). The reaction took approximately 3-5 hours for completion. When the reaction was complete, extraction was performed with 3×15

L of 10% sodium bicarbonate and 20 L of water. The organic phase (DCM) was evaporated to a syrup (bath temp. 40° C.) and allowed to dry overnight. The syrup was purified in a 200 L silica column using 140 L each of the following gradient profiles: 5:95, 10:90, 20:80, 30:70, 40:60 and 50:50 (EtOAc/heptane). Pure fractions were pooled and evaporated to a syrup. The isolated yield of AMod1 was 83%.

Synthesis of the BA Dimer

Step 8. Preparation of AMod3, 1-Methylation of AMod1

A 100 L reactor was charged with 5891 g of acetyl Monomer A2 (AMod1) (13.98 mole, 1 eq.) in 32 L of dichloromethane. The reactor was purged with nitrogen and was chilled to 0° C., after which 2598 mL of trimethylsilyl iodide (TMSI, 3636 g, 18 mol, 1.3 equiv) was transferred into the reactor. When addition was complete, the reaction was allowed to warm to room temperature. The completeness of the reaction was monitored by HPLC and TLC (30:70 ethyl acetate/heptane). The reaction took approximately 2-4 hours to reach completion. When the reaction was complete, the mixture was diluted with 20 L of toluene. The solution was evaporated to a syrup and was co-evaporated with 3×6 L of toluene. The reactor was charged with 36 L of dichloromethane (DCM), 3.2 Kg of dry 4A Molecular Sieves, 15505 g (42 mol, 3 equiv) of tetrabutyl ammonium iodide (TBAI) and 9 L of dry methanol. This was stirred until the TBAI was completely dissolved, after which 3630 mL of diisopropyl-ethylamine (DIPEA, 2712 g, 21 moles, 1.5 equiv) was transferred into the reactor in one portion. The completion of the reaction was monitored by HPLC and TLC (30:70 ethyl acetate/heptane). The reaction took approximately 16 hours for completion. When the reaction was complete, the molecular sieves were removed by filtration. Added were 20 L EtOAc and extracted with 4×20 L of 25% sodium thiosulfate and 20 L 10% NaCl solutions. The organic layer was separated and dried with 8-12 Kg of anhydrous sodium sulfate. The solution was evaporated to a syrup (bath temp. 40° C.). The crude product was purified in a 200 L silica column using 140-200 L each of the following gradient profiles: 5:95, 10:90, 20:80, 30:70 and 40:60 (EtOAc/heptane). The pure fractions were pooled and evaporated to give intermediate AMod3 as a syrup. The isolated yield was 75%.

Synthesis of the BA Dimer

Step 9. Preparation of AMod4, DeAcetylation of AMod3

A 100 L reactor was charged with 4128 g of 1-Methyl 4,6-Diacetyl Monomer A2 (AMod3) (10.5 mol, 1 equiv) and 18 L of dry methanol and dissolved, after which 113.4 g (2.1 mol, 0.2 equiv) of sodium methoxide was transferred into the reactor. The reaction was stirred at room temperature and monitored by TLC (40% ethyl acetate/hexane) and HPLC. The reaction took approximately 2-4 hours for completion. When the reaction was complete, Dowex 50W×8 cation resin was added in small portions until the pH reached 6-8. The Dowex 50W×8 resin was filtered and the solution was evaporated to a syrup (bath temp. 40° C.). The syrup was diluted with 10 L of ethyl acetate and extracted with 20 L brine and 20 L water. The ethyl acetate solution was dried in 4-6 Kg of anhydrous sodium sulfate. The solution was evaporated to a syrup (bath temp. 40° C.) and dried overnight at the same temperature. The isolated yield of the syrup AMod4 was about 88%.

Synthesis of the BA Dimer

Step 10. Preparation of AMod5, 6-Benzoylation

A 100 L reactor was charged with 2858 g of Methyl 4,6-diOH Monomer A2 (AMod4) (9.24 mol, 1 equiv) and co-evaporated with 3×10 L of pyridine. When evaporation was complete, 15 L of dichloromethane, 6 L of pyridine were transferred into the reactor and dissolved. The reactor was purged with nitrogen and chilled to −40° C. The reactor was charged with 1044 mL (1299 g, 9.24 mol, 1 equiv) of benzoyl chloride. When the addition was complete, the reaction was allowed to warm to −10° C. over a period of 2 hours. The reaction was monitored by TLC (60% ethyl acetate/hexane). When the reaction was completed, the solution was evaporated to a syrup (bath temp. 40° C.). This was co-evaporated with 3×15 L of toluene. The syrup was diluted with 40 L ethyl acetate. Extraction was carried out with 20 L of water and 20 L of brine solution. The Ethyl acetate solution was dried in 4-6 Kg of anhydrous sodium sulfate. The solution was evaporated to a syrup (bath temp. 40° C.). The crude product was purified in a 200 L silica column using 140-200 L each of the following gradient profiles: 5:95, 10:90, 20:80, 25:70 and 30:60 (EtOAc/heptane). The pure fractions were pooled and evaporated to a syrup. The isolated yield of the intermediate AMod5 was 84%.

Synthesis of the BA Dimer

Step 11. Preparation of BA1, Coupling of Amod5 with BMod6

A 100 L reactor was charged with 3054 g of methyl 4-Hydroxy-Monomer A2 (AMod5) from Step 10 (7.38 mol, 1 equiv) and 4764 g of 4-Lev-1-TCA-Monomer B1 (BMod6) from Step 6 (7.38 mol, 1 equiv). The combined monomers were dissolved in 20 L of toluene and co-evaporated at 40° C. Co evaporation was repeated with an additional 2×20 L of toluene, after which 30 L of dichloromethane (DCM) was transferred into the reactor and dissolved. The reactor was purged with nitrogen and was chilled to below −20° C. When the temperature was between −20° C. and −40° C., 1572 g (1404 mL, 11.12 moles, 1.5 equiv) of boron trifluoride etherate ($BF_3.Et_2O$) were transferred into the reactor. After complete addition of boron trifluoride etherate, the reaction was allowed to warm to 0° C. and stirring was continued. The completeness of the reaction was monitored by HPLC and TLC (40:70 ethyl acetate/heptane). The reaction required 3-4 hours to reach completion. When the reaction was complete, 926 mL (672 g, 6.64 mol, 0.9 equiv) of triethylamine (TEA) was transferred into the mixture and stirred for an additional 30 minutes, after which 20 L of water and 10 L of dichloromethane were transferred into the reactor. The solution was stirred for 30 min and the layers were separated. The organic layer (DCM layer) was separated with 2×20 L water and 20 L 25% 4:1 sodium chloride/sodium bicarbonate solution. The dichloromethane solution was dried in 4-6 Kg of anhydrous sodium sulfate. The solution was evaporated to a syrup (bath temp. 40° C.) and used in the next step. The isolated yield of the disaccharide BA1 was about 72%.

Synthesis of the BA Dimer

Step 12, Removal of Levulinate (Methyl [(methyl 2-O-benzoyl-3-O-benzyl-α-L-Idopyranosyluronate)-(1→4)-2-azido-6-O-benzoyl-3-O-benzyl]-2-deoxy-α-D-glucopyranoside)

A 100 L reactor was charged with 4.104 Kg of 4-Lev BA Dimer (BA1) (4.56 mol, 1 equiv) in 20 L of THF. The reactor was purged with nitrogen and chilled to −20 to −25° C., after which 896 mL of hydrazine hydrate (923 g, 18.24 mol, 4 equiv) was transferred into the reactor. Stirring was continued and the reaction was monitored by TLC (40% ethyl acetate/heptane) and HPLC. The reaction took approximately 2-3 hour for the completion, after which 20 L of 10% citric acid, 10 L of water and 25 L of ethyl acetate were transferred into the reactor. This was stirred for 30 min and the layers were separated. The organic layer (ETOAc layer) was extracted with 20 L 25% brine solutions. The ethyl acetate solution was dried in 4-6 Kg of anhydrous sodium sulfate. The solution was evaporated to a syrup (bath temp. 40° C.). The crude product was purified in a 200 L silica column using 140-200 L each of the following gradient profiles: 10:90, 20:80, 30:70, 40:60 and 50:50 (EtOAc/heptane). The pure fractions were pooled and evaporated to dryness. The isolated yield of the BA Dimer was 82%. Formula: $C_{42}H_{43}N_3O_{13}$; Mol. Wt. 797.80.

Synthesis of the EDC Trimer

Step 1. Preparation of EMod1, Acetylation

A 100 L reactor was charged with 16533 g of Monomer E (45 mole, 1 eq.), 21.25 L acetic anhydride (225 mole, 5 eq.) and 60 L of dichloromethane. The reactor was purged with nitrogen and was chilled to −10° C. When the temperature was at −10° C., 1.14 L (1277 g) of boron trifluoride etherate ($BF_3.Et_2O$, 9.0 moles, 0.2 eq) were transferred into the reactor. After the complete addition of boron trifluoride etherate, the reaction was allowed to warm to room temperature. The completeness of the reaction was monitored by TLC (30:70 ethyl acetate/heptane) and HPLC. The reaction took approximately 3-6 hours to reach completion. When the reaction was completed, the mixture was extracted with 3×50 L of 10% sodium bicarbonate and 5OL of water. The organic phase (DCM) was evaporated to a syrup (bath temp. 40° C.) and allowed to dry overnight. The isolated yield of EMod1 was 97%.

Synthesis of the EDC Trimer

Step 2. Preparation of EMod2, De-Acetylation of Azidoglucose

A 100 L reactor was charged with 21016 g of 1,6-Diacetyl Monomer E (EMod1) (45 mole, 1 eq.), 5434 g of hydrazine acetate ($NH_2NH_2.HOAc$, 24.75 mole, 0.55 eq.) and 50 L of DMF (dimethyl formamide). The solution was stirred at room temperature and the reaction was monitored by TLC (30% ethyl acetate/hexane) and HPLC. The reaction took approximately 2-4 hours for completion. When the reaction was completed, 50 L of dichloromethane and 40 L of water were transferred into the reactor. This was stirred for 30 minutes and the layers were separated. This was extracted with an additional 40 L of water and the organic phase was dried in 6-8 Kg of anhydrous sodium sulfate. The solution was evaporated to a syrup (bath temp. 40° C.) and dried overnight at the same temperature. The syrup was purified in a 200 L silica column using 140-200 L each of the following gradient profiles: 20:80, 30:70, 40:60 and 50:50 (EtOAc/heptane). Pure fractions were pooled and evaporated to a syrup. The isolated yield of intermediate EMod2 was 100%.

Synthesis of the EDC Trimer

Step 3. Preparation of EMod3, Formation of 1-TCA

A 100 L reactor was charged with 12752 g of 1-Hydroxy Monomer E (EMod2) (30 mole, 1 eq.) in 40 L of dichloromethane. The reactor was purged with nitrogen and stirring was started, after which 2.25 L of DBU (15 moles, 0.5 eq.) and 15.13 L of trichloroacetonitrile (150.9 moles, 5.03 eq) were transferred into the reactor. Stirring was continued and the reaction was kept under nitrogen. After the reagent addition, the reaction was allowed to warm to ambient temperature. The reaction was monitored by TLC (30:70 ethyl acetate/Heptane) and HPLC. The reaction took approximately 2-3 hours to reach completion. When the reaction was complete, 40 L of water and 20 L of DCM were charged into the reactor. This was stirred for 30 min and the layers were separated. The organic layer (DCM layer) was extracted with 40 L water and the DCM solution was dried in 6-8 Kg of anhydrous sodium sulfate. The solution was evaporated to a syrup (bath temp. 40° C.). The crude product was purified in a 200 L silica column using 140-200 L each of the following gradient profiles: 10:90 (DCM/EtOAc/heptane), 20:5:75 (DCM/EtOAc/heptane) and 20:10:70 DCM/EtOAc/heptane). Pure fractions were pooled and evaporated to give Intermediate EMod3 as a syrup. Isolated yield was 53%.

Synthesis of the EDC Trimer

Step 4. Preparation of ED Dimer, Coupling of E-TCA with Monomer D

A 100 L reactor was charged with 10471 g of 6-Acetyl-1-TCA Monomer E (EMod3) (18.3 mole, 1 eq., FW: 571.8) and 6594 g of Monomer D (16.47 mole, 0.9 eq, FW: 400.4). The combined monomers were dissolved in 20 L toluene and co-evaporated at 40° C. This was repeated with co-evaporation with an additional 2×20 L of toluene, after which 60 L of dichloromethane (DCM) were transferred into the reactor and dissolved. The reactor was purged with nitrogen and was chilled to −40° C. When the temperature was between −30° C. and −40° C., 2423 g (2071 mL, 9.17 moles, 0.5 eq) of TES Triflate were transferred into the reactor. After complete addition of TES Triflate the reaction was allowed to warm and stiffing was continued. The completeness of the reaction was monitored by HPLC and TLC (35:65 ethyl acetate/Heptane). The reaction required 2-3 hours to reach completion. When the reaction was completed, 2040 mL of triethylamine (TEA, 1481 g, 0.8 eq.) were transferred into the reactor and stirred for an additional 30 minutes. The organic layer (DCM layer) was extracted with 2×20 L 25% 4:1 sodium chloride/sodium bicarbonate solution. The dichloromethane solution was dried in 6-8 Kg of anhydrous sodium sulfate. The syrup was purified in a 200 L silica column using 140-200 L each of the following gradient profiles: 15:85, 20:80, 25:75, 30:70 and 35:65 (EtOAc/heptane). Pure fractions were pooled and evaporated to a syrup. The ED Dimer was obtained in 81% isolated yield.

Synthesis of the EDC Trimer

Step 5. Preparation of ED1 TFA, Hydrolysis of ED Dimer

A 100 L reactor was charged with 7.5 Kg of ED Dimer (9.26 mol, 1 equiv). The reactor was chilled to <5° C. and 30.66 L of 90% TFA solution (TFA, 370.4 mol, 40 equiv) were transferred into the reactor. When the addition was completed the reaction was allowed to warm to room temperature. The reaction was monitored by TLC (40:60 ethyl acetate/hexanes) and HPLC. The reaction took approximately 3-4 hours to reach completion. When the reaction was completed, was chilled and 51.6 L of triethylamine (TEA, 37.5 Kg, 370.4 mole) were transferred into the reactor, after which 20 L of water & 20 L ethyl acetate were transferred into the reactor. This was stirred for 30 min and the layers were separated. The organic layer (EtOAc layer) was extracted with 20 L 5% sodium bicarbonate and 20 L 25% brine solutions. Ethyl acetate solution was dried in 4-6 Kg of anhydrous sodium sulfate. The solution was evaporated to a syrup (bath temp. 40° C.). The crude product was purified in a 200 L silica column using 140-200 L each of the following gradient profiles: 20:80, 30:70, 40:60, 50:50, 60:40 (EtOAc/heptane). The pure fractions were pooled and evaporated to a syrup. Isolated yield of ED1 was about 70%.

Synthesis of the EDC Trimer

Step 6. Preparation of ED2, Silylation of ED1

A 100 L reactor was charged with 11000 g of 1,2-diOH ED Dimer (ED1) (14.03 mol, 1 equiv), 1910.5 g of imidazole (28.06 mol, 2 equiv) and 30 L of dichloromethane. The reactor was purged with nitrogen and chilled to −20° C., after which 3.53 L butyldiphenylchloro-silane (TBDPS-Cl, 4.628 Kg, 16.835 mol, 1.2 equiv) was charged into the reactor. When the addition was complete, the chiller was turned off and the reaction was allowed to warm to ambient temperature. The reaction was monitored by TLC (50% ethyl acetate/hexane) and HPLC. The reaction required 4-6 hours to reach completion. When the reaction was completed, 20 L of water and 10 L of dichloromethane were transferred into the reactor and stirred for 30 min and the layers were separated. The organic layer (DCM layer) was extracted with 20 L water and 20 L 25% brine solutions. Dichloromethane solution was dried in 4-6 Kg of anhydrous sodium sulfate. The solution was evaporated to a syrup (bath temp. 40° C.). Intermediate ED2 was obtained in 75% isolated yield.

Synthesis of the EDC Trimer

Step 7. Preparation of ED3, D-Levulination

A 100 L reactor was charged with 19800 g of 1-Silyl ED Dimer (ED2) (19.37 moles, 1 equiv) and 40 L of dry tetrahydrofuran (THF) and agitated to dissolve. The reactor was purged with nitrogen and 237 g of dimethylaminopyridine (DMAP, 1.937 moles, 0.1 equiv) and 10.05 L of diisopropylethylamine (DIPEA, 63.9 moles, 3 equiv) were transferred into the reactor. The reactor was chilled to 10-15° C. and kept under a nitrogen atmosphere, after which 12.46 Kg of levulinic anhydride (58.11 moles, 3 eq) was charged into the reactor. When the addition was complete, the reaction was warmed to ambient temperature and stirred overnight or 12-16 hours. The completeness of the reaction was monitored by TLC (40:60 ethyl acetate/hexane) and by HPLC. 20 L of 10% citric acid, 10 L of water and 25 L of ethyl acetate were transferred into the reactor. This was stirred for 30 min and the layers were separated. The organic layer (EtOAc layer) was extracted with 20 L of water, 20 L 5% sodium bicarbonate and 20 L 25% brine solutions. The ethyl acetate solution was dried in 6-8 Kg of anhydrous sodium sulfate. The solution was evaporated to a syrup (bath temp. 40° C.). The ED3 yield was 95%.

Synthesis of the EDC Trimer

Step 8. Preparation of ED4, Desilylation of ED3

A 100 L reactor was charged with 19720 g of 1-Silyl-2-Lev ED Dimer (ED3) (17.6 mol, 1 equiv) in 40 L of THF. The reactor was chilled to 0° C., after which 6903 g of tetrabutylammonium fluoride trihydrate (TBAF, 26.4 mol, 1.5 equiv) and 1511 mL (26.4 mol, 1.5 equiv) of glacial acetic acid were transferred into the reactor. When the addition was complete, the reaction was stirred and allowed to warm to ambient temperature. The reaction was monitored by TLC (40:60 ethyl acetate/hexane) and HPLC. The reaction required 3 hours to reach completion. When the reaction was completed, 20 L of water and 10 L of dichloromethane were transferred into the reactor and stirred for 30 min and the layers were separated. The organic layer (DCM layer) was extracted with 20 L water and 20 L 25% brine solutions. The dichloromethane solution was dried in 6-8 Kg of anhydrous sodium sulfate. The solution was evaporated to a syrup (bath temp. 40° C.). The crude product was purified using a 200 L silica column using 140-200 L each of the following gradient profiles: 10:90, 20:80, 30:70, 40:60, 50:50, 60:40, 70:30, 80:20 (EtOAc/heptane) and 200 L 100% EtOAc. The pure fractions were pooled and evaporated to a syrup and used in the next step. The isolated yield of ED4 was about 92%.

Synthesis of the EDC Trimer

Step 9. Preparation of ED5, TCA Formation

A 100 L reactor was charged with 14420 g of 1-OH-2-Lev ED Dimer (ED4) (16.35 mol, 1 equiv) in 30 L of dichloromethane. The reactor was purged with nitrogen and stirring was begun, after which 1222 mL of diazabicycloundecene (DBU, 8.175 mol, 0.5 equiv) and 23.61 Kg of trichloroacetonitrile (TCA, 163.5 mol, 10 equiv) were transferred into the reactor. Stirring was continued and the reaction was kept under nitrogen. After reagent addition, the reaction was allowed to warm to ambient temperature. The reaction was monitored by HPLC and TLC (40:60 ethyl acetate/heptane). The reaction took approximately 2 hours for reaction completion. When the reaction was completed, 20 L of water and 10 L of DCM were transferred into the reactor and stirred for 30 min and the layers were separated. The organic layer (DCM layer) was extracted with 20 L water and 20 L 25% brine solutions. The dichloromethane solution was dried in 6-8 Kg of anhydrous sodium sulfate. The solution was evaporated to a syrup (bath temp. 40° C.). The crude product was purified using a 200 L silica column using 140-200 L each of the following gradient profiles: 10:90, 20:80, 30:70, 40:60 and 50:50 (EtOAc/heptane). The pure fractions were pooled and evaporated to a syrup and used in the next step. The isolated yield of intermediate ED5 was about 70%.

Synthesis of the EDC Trimer

Step 10. Preparation of EDC Trimer, Coupling of ED5 with Monomer C (6-O-acetyl-2-azido-3,4-di-O-benzyl-2-deoxy-α-D-glucopyranosyl-(1→4)-benzyl (3-O-benzyl-2-O-levulinoyl)-β-D-glucopyranosyluronate-(1→4)-(3-O-acetyl-1,6-anhydro-2-azido)-2-deoxy-β-D-glucopyranose)

Figure 3:
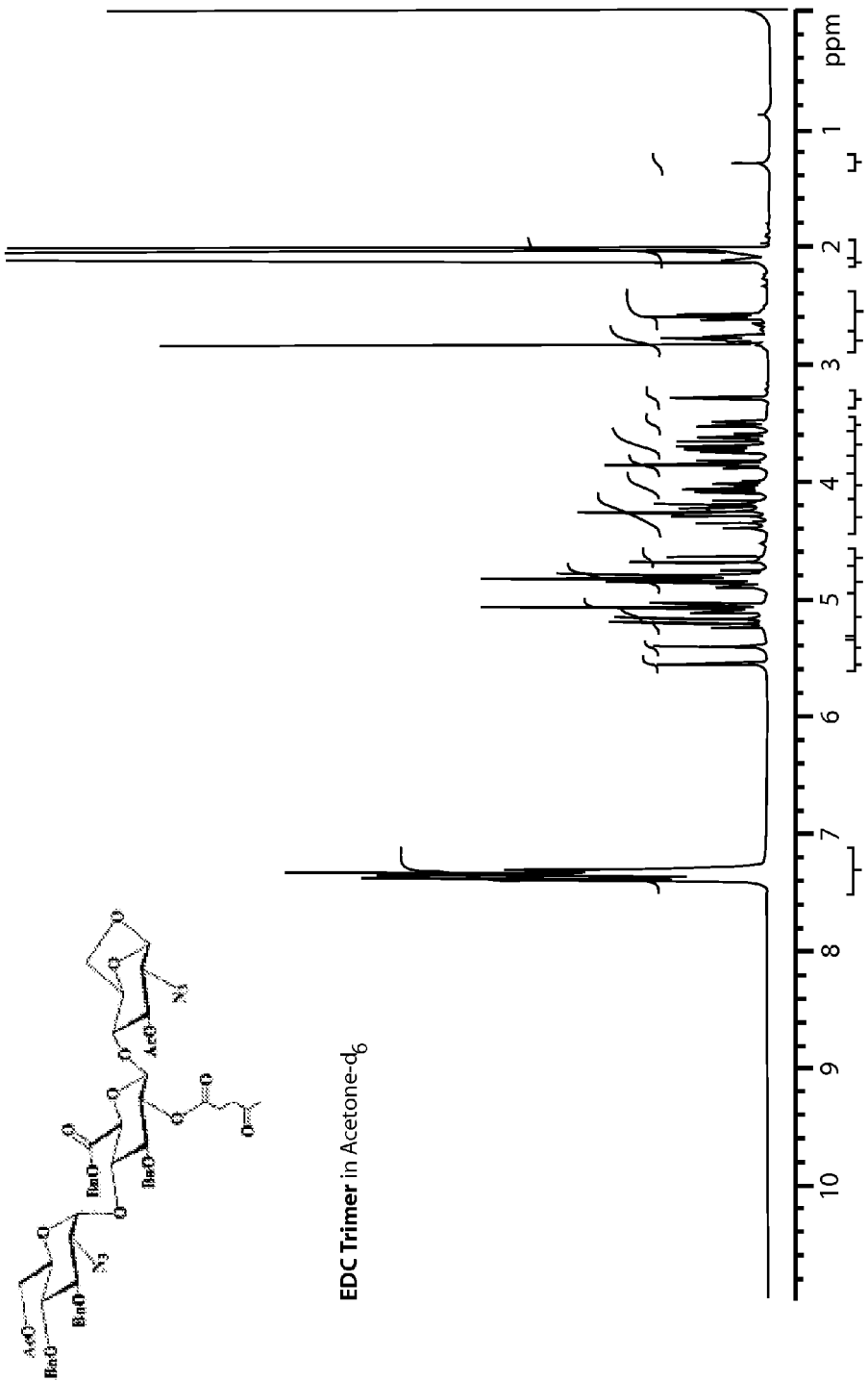
FIG. 3 is a $^1$H NMR spectrum of the EDC trimer.

A 100 L reactor was charged with 12780 g of 2-Lev 1-TCA ED Dimer (ED5) (7.38 mole, 1 eq., FW) and 4764 g of Monomer C (7.38 mole, 1 eq). The combined monomers were dissolved in 20 L toluene and co-evaporated at 40° C. Repeated was co-evaporation with an additional 2×20 L of toluene, after which 60 L of dichloromethane (DCM) was transferred into the reactor and dissolved. The reactor was purged with nitrogen and chilled to −20° C. When the temperature was between −20 and −10° C., 2962 g (11.2 moles, 0.9 eq) of TES Triflate were transferred into the reactor. After complete addition of TES Triflate the reaction was allowed to warm to 5° C. and stirring was continued. Completeness of the reaction was monitored by HPLC and TLC (35:65 ethyl acetate/Heptane). The reaction required 2-3 hours to reach completion. When the reaction was completed, 1133 g of triethylamine (TEA, 0.9 eq.) were transferred into the reactor and stirred for an additional 30 minutes. The organic layer (DCM layer) was extracted with 2×20 L 25% 4:1 sodium chloride/sodium bicarbonate solution. Dichloromethane solution was dried in 6-8 Kg of anhydrous sodium sulfate. The syrup was purified in a 200 L silica column using 140-200 L each of the following gradient profiles: 15:85, 20:80, 25:75, 30:70 and 35:65 (EtOAc/heptane). Pure fractions were pooled and evaporated to a syrup. The isolated yield of EDC Trimer was 48%. Formula: $C_{55}H_{60}N_6O_{18}$; Mol. Wt. 1093.09. The $^1$H NMR spectrum (d6-acetone) of the EDC trimer is shown in FIG. 3.

Preparation of EDC1

Step 1: Anhydro Ring Opening & Acetylation

Figure 4:
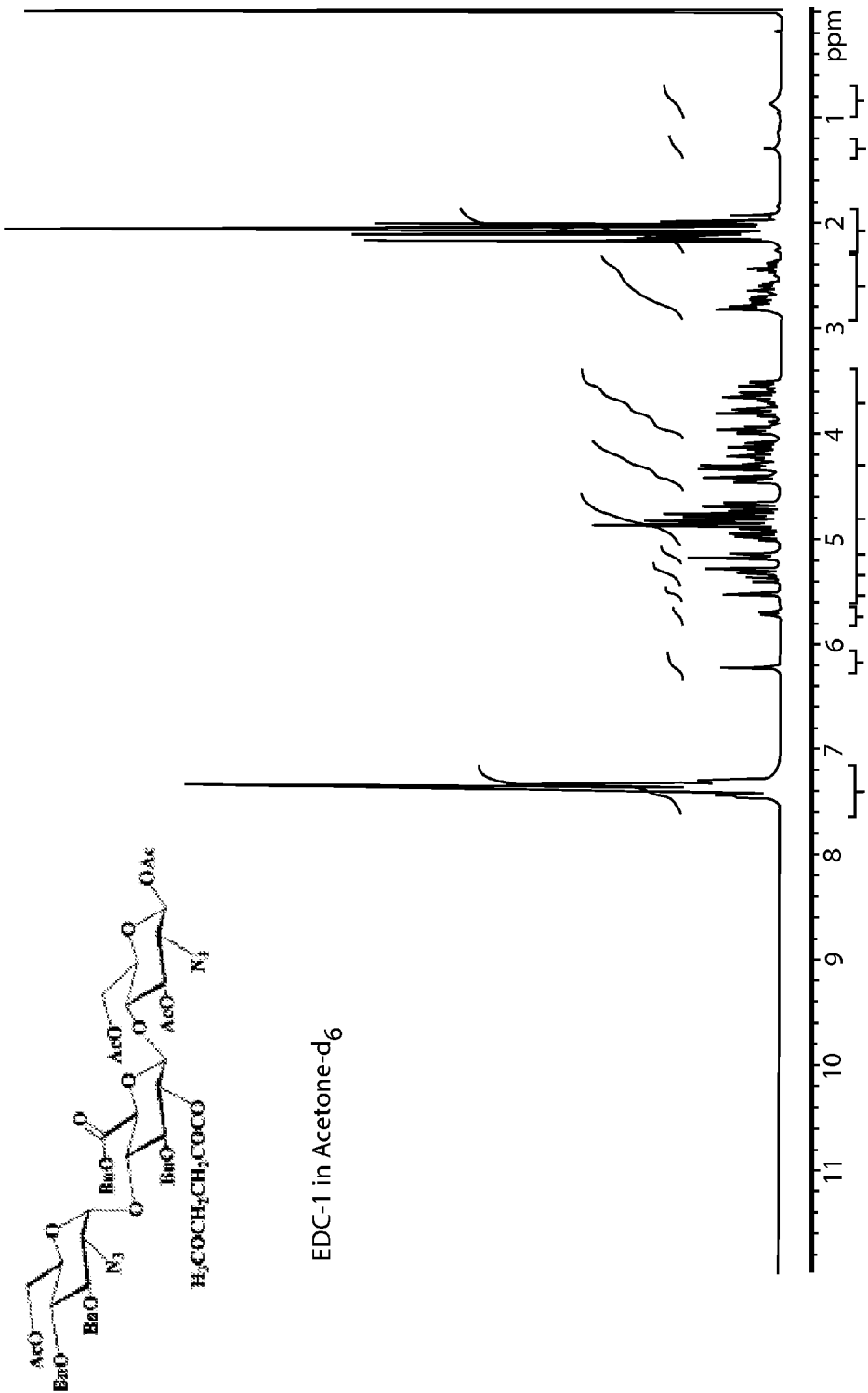
FIG. 4 is a $^1$H NMR spectrum of the EDC-1 trimer.

6-O-acetyl-2-azido-2-deoxy-3,4-di-O-benzyl-α-D-glucopyranosyl-(1→4)-O-[benzyl 3-O-benzyl-2-O-levulinoyl-β-D-glucopyranosyluronate]-(1→4)-O-2-azido-2-deoxy-1,3,6-tri-O-acetyl-β-D-glucopyranose 7.0 Kg (6.44 mol) of EDC Trimer was dissolved in 18 L anhydrous Dichloromethane. 6.57 Kg (64.4 mol, 10 eq) of Acetic anhydride was added. The solution was cooled to −45 to −35° C. and 1.82 Kg (12.9 mol, 2 eq) of Boron Trifluoride etherate was added slowly. Upon completion of addition, the mixture was warmed to 0-10° C. and kept at this temperature for 3 hours until reaction was complete by TLC and HPLC. The reaction was cooled to −20° C. and cautiously quenched and extracted with saturated solution of sodium bicarbonate (3×20 L) while maintaining the mixture temperature below 5° C. The organic layer was extracted with brine (1×20 L), dried over anhydrous sodium sulfate, and concentrated under vacuum to a syrup. The resulting syrup of EDC1 (6.74 Kg) was used for step 2 without further purification. The $^1$H NMR spectrum (d6-acetone) of the EDC-1 trimer is shown in FIG. 4.

Preparation of EDC2

Step 2: Deacetylation

6-O-acetyl-2-azido-2-deoxy-3,4-di-O-benzyl-α-D-glucopyranosyl-(1→4)-O-[benzyl 3-O-benzyl-2-O-levulinoyl-β-D-glucopyranosyluronate]-(1→4)-O-2-azido-2-deoxy-3,6-di-O-acetyl-β-D-glucopyranose The crude EDC1 product obtained from step 1 was dissolved in 27 L of Tetrahydrofuran and chilled to 15-20° C., after which 6 Kg (55.8 mol) of benzylamine was added slowly while maintaining the reaction temperature below 25° C. The reaction mixture was stirred for 5-6 hours at 10-15° C. Upon completion, the mixture was diluted with ethyl acetate and extracted and quenched with 10% citric acid solution (2×20 L) while maintaining the temperature below 25° C. The organic layer was extracted with 10% NaCl/1% sodium bicarbonate (1×20 L). The extraction was repeated with water (1×10 L), dried over anhydrous sodium sulfate and evaporated under vacuum to a syrup. Column chromatographic separation using silica gel yielded 4.21 Kg (57% yield over 2 steps) of EDC2 [also referred to as 1-Hydroxy-6-Acetyl EDC Trimer]. The $^1$H NMR spectrum (d6-acetone) of the EDC-2 trimer is shown in FIG. 5.

Preparation of EDC3

Step 3: Formation of TCA Derivative

Figure 6:
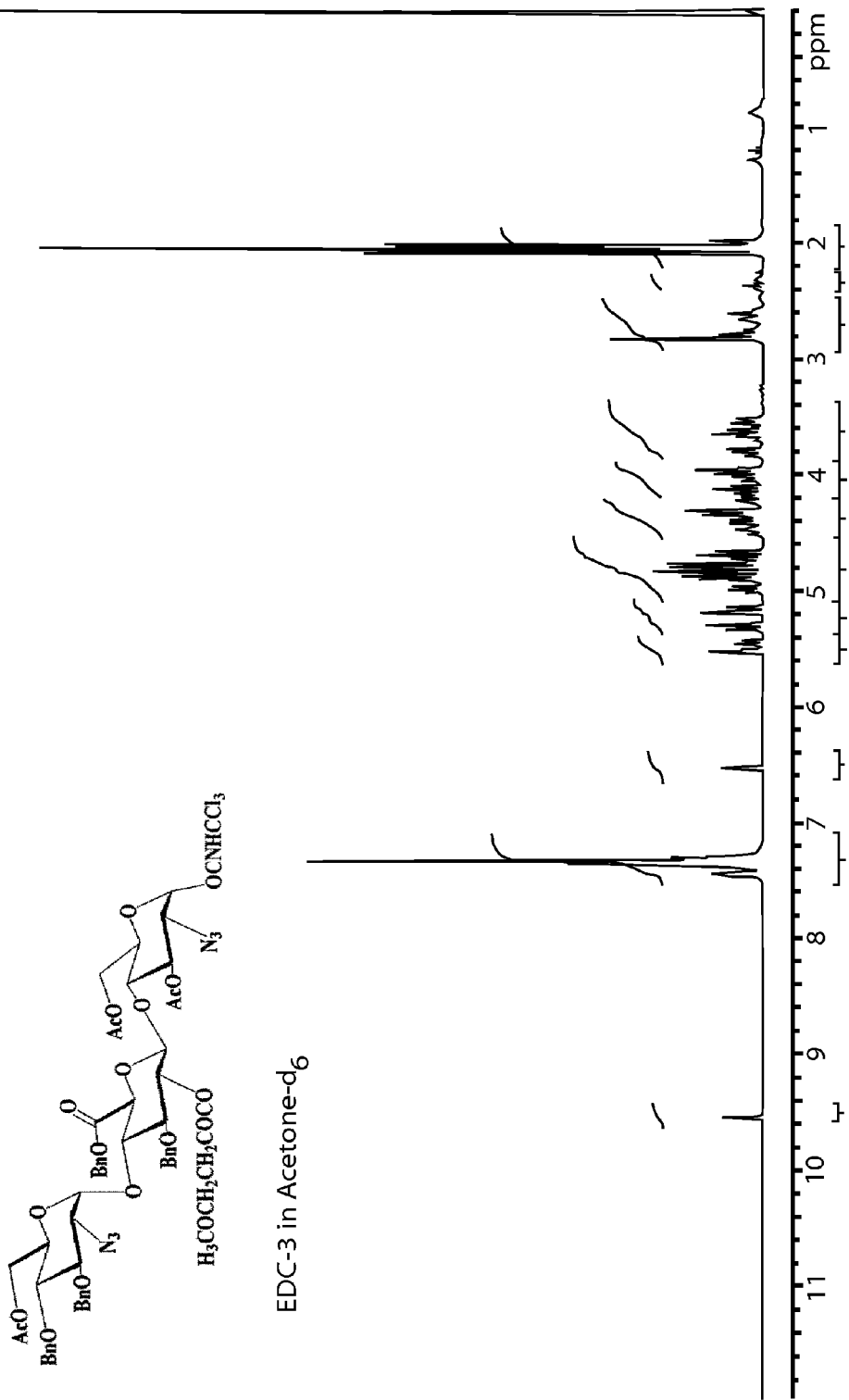
FIG. 6 is a $^1$H NMR spectrum of the EDC-3 trimer.

6-O-acetyl-2-azido-2-deoxy-3,4-di-O-benzyl-α-D-glucopyranosyl-(1→4)-O-[benzyl 3-O-benzyl-2-O-levulinoyl-β-D-glucopyranosyluronate]-(1→4)-O-2-azido-2-deoxy-3,6-di-O-acetyl-1-O-trichloroacetimidoyl-β-D-glucopyranose 4.54 Kg (3.94 mol) of EDC2 was dissolved in 20 L of Dichloromethane. 11.4 Kg (78.8 mol, 20 eq) of Trichloroacetonitrile was added. The solution was cooled to −15 to −20° C. and 300 g (1.97 mol, 0.5 eq) of Diazabicycloundecene was added. The reaction was allowed to warm to 0-10° C. and stirred for 2 hours or until reaction was complete. Upon completion, water (20 L) was added and the reaction was extracted with an additional 10 L of DCM. The organic layer was extracted with brine (1×20 L), dried over anhydrous sodium sulfate, and concentrated under vacuum to a syrup. Column chromatographic separation using silica gel and 20-60% ethyl acetate/heptane gradient yielded 3.67 Kg (72% yield) of 1-TCA derivative, EDC3. The $^1$H NMR spectrum (d6-acetone) of the EDC-3 trimer is shown in FIG. 6.

Preparation of EDCBA1

Step 4: Coupling of EDC3 with BA Dimer

Figure 7:
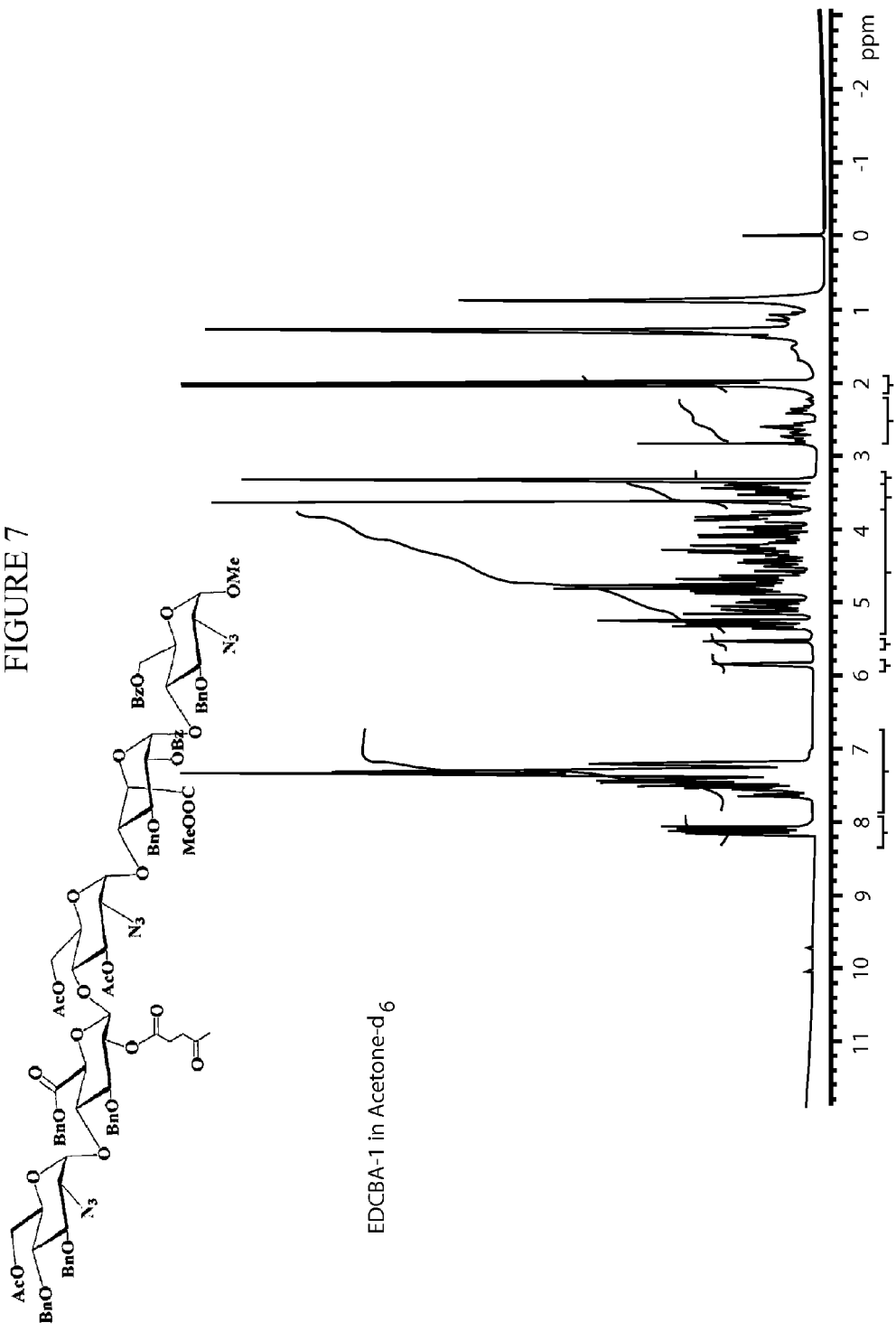
FIG. 7 is a $^1$H NMR spectrum of the EDCBA-1 pentamer.

Methyl O-6-O-acetyl-2-azido-2-deoxy-3,4-di-O-benzyl-α-D-glucopyranosyl)-(1→4)-O-[benzyl 3-O-benzyl-2-O-levulinoyl-β-D-glucopyranosyluronate]-(1→4)-O-2-azido-2-deoxy-3,6-di-O-acetyl-α-D-glucopyranosyl-(1→4)-O-[methyl 2-O-benzoyl-3-O-benzyl-α-L-Idopyranosyluronate]-(1→4)-2-azido-6-O-benzoyl-3-O-benzyl-2-deoxy-α-D-glucopyranoside 3.67 Kg (2.83 mol) of EDC3 and 3.16 Kg (3.96 mol, 1.4 eq) of BA Dimer was dissolved in 7-10 L of Toluene and evaporated to dryness. The resulting syrup was coevaporated with Toluene (2×15 L) to remove water. The dried syrup was dissolved in 20 L of anhydrous Dichloromethane, transferred to the reaction flask, and cooled to −15 to −20° C. 898 g (3.4 mol, 1.2 eq) of triethylsilyl triflate was added while maintaining the temperature below −5° C. When the addition was complete, the reaction was immediately warmed to −5 to 0° C. and stirred for 3 hours. The reaction was quenched by slowly adding 344 g (3.4 mol, 1.2 eq) of Triethylamine. Water (15 L) was added and the reaction was extracted with an additional 10 L of DCM. The organic layer was extracted with a 25% 4:1 Sodium Chloride/Sodium Bicarbonate solution (2×20 L), dried over anhydrous sodium sulfate, and evaporated under vacuum to a syrup. The resulting syrup of the pentasaccharide, EDCBA1 was used for step 5 without further purification. The $^1$H NMR spectrum (d6-acetone) of the EDCBA-1 pentamer is shown in FIG. 7.

Preparation of EDCBA2

Step 5: Hydrolysis of Levulinyl Moiety

Figure 8:
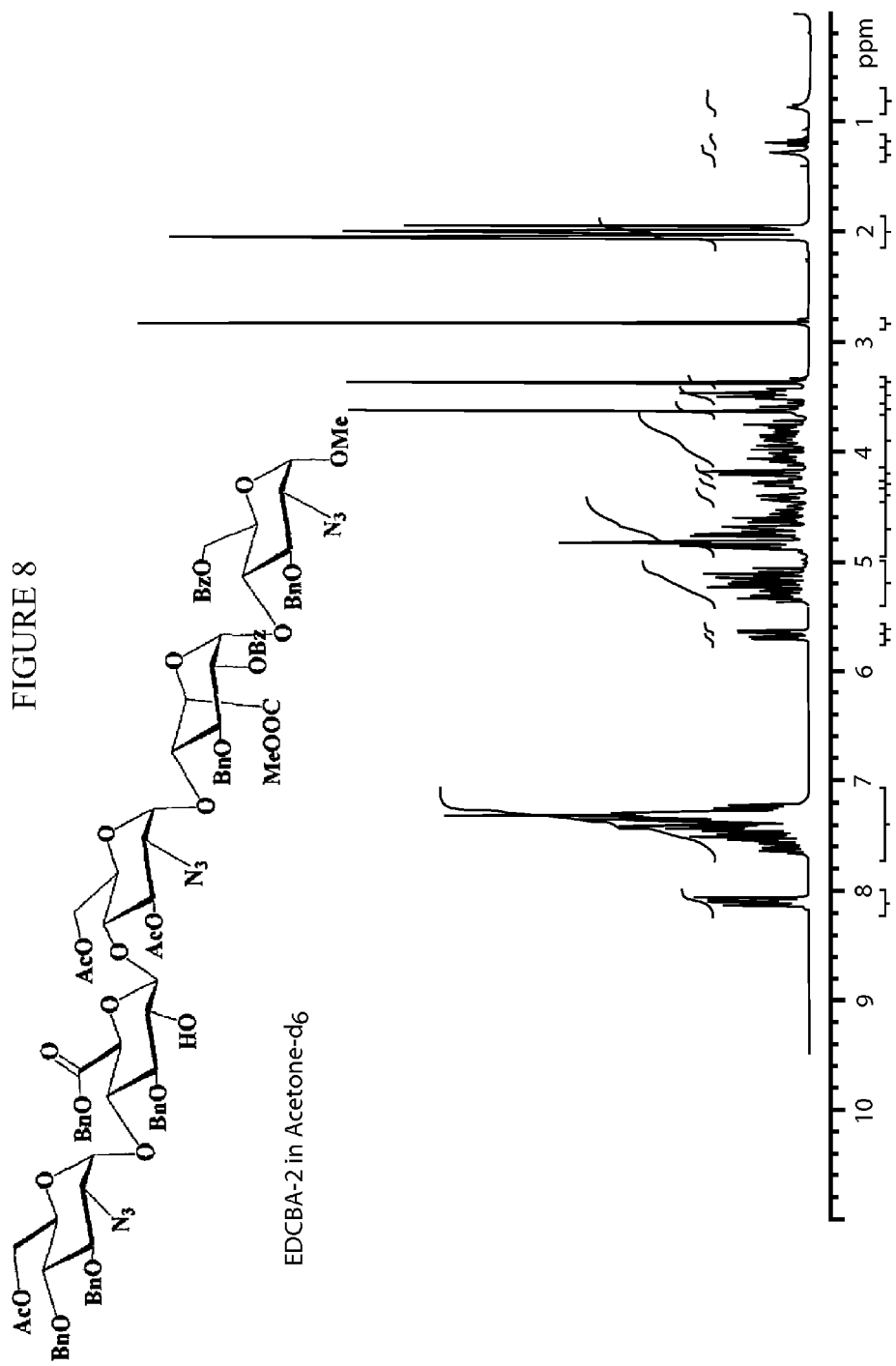
FIG. 8 is a $^1$H NMR spectrum of the EDCBA-2 pentamer.

Methyl O-6-O-acetyl-2-azido-2-deoxy-3,4-di-O-benzyl-α-D-glucopyranosyl)-(1→4)-O-[benzyl 3-O-benzyl-β-D-glucopyranosyluronate]-(1→4)-O-2-azido-2-deoxy-3,6-di-O-acetyl-α-D-glucopyranosyl)-(1→4)-O-[methyl 2-O-benzoyl-3-O-benzyl-α-L-Idopyranosyluronate]-(1→4)-2-azido-6-O-benzoyl-3-O-benzyl-2-deoxy-α-D-glucopyranoside The crude EDCBA1 from step 4 was dissolved in 15 L of Tetrahydrofuran and chilled to −20 to −25° C. A solution containing 679 g (13.6 mol) of Hydrazine monohydrate and 171 g (1.94 mol) of Hydrazine Acetate in 7 L of Methanol was added slowly while maintaining the temperature below −20° C. When the addition was complete, the reaction mixture was allowed to warm to 0-10° C. and stirred for several hours until the reaction is complete, after which 20 L of Ethyl acetate was added and the reaction was extracted with 10% citric acid (2×12 L). The organic layer was washed with water (1×12 L), dried over anhydrous sodium sulfate, and evaporated under vacuum to a syrup. Column chromatographic separation using silica gel and 10-45% ethyl acetate/heptane gradient yielded 2.47 Kg (47.5% yield over 2 steps) of EDCBA2. The $^1$H NMR spectrum (d6-acetone) of the EDCBA-2 pentamer is shown in FIG. 8.

Preparation of EDCBA Pentamer

Step 6: THP Formation

Figure 9:
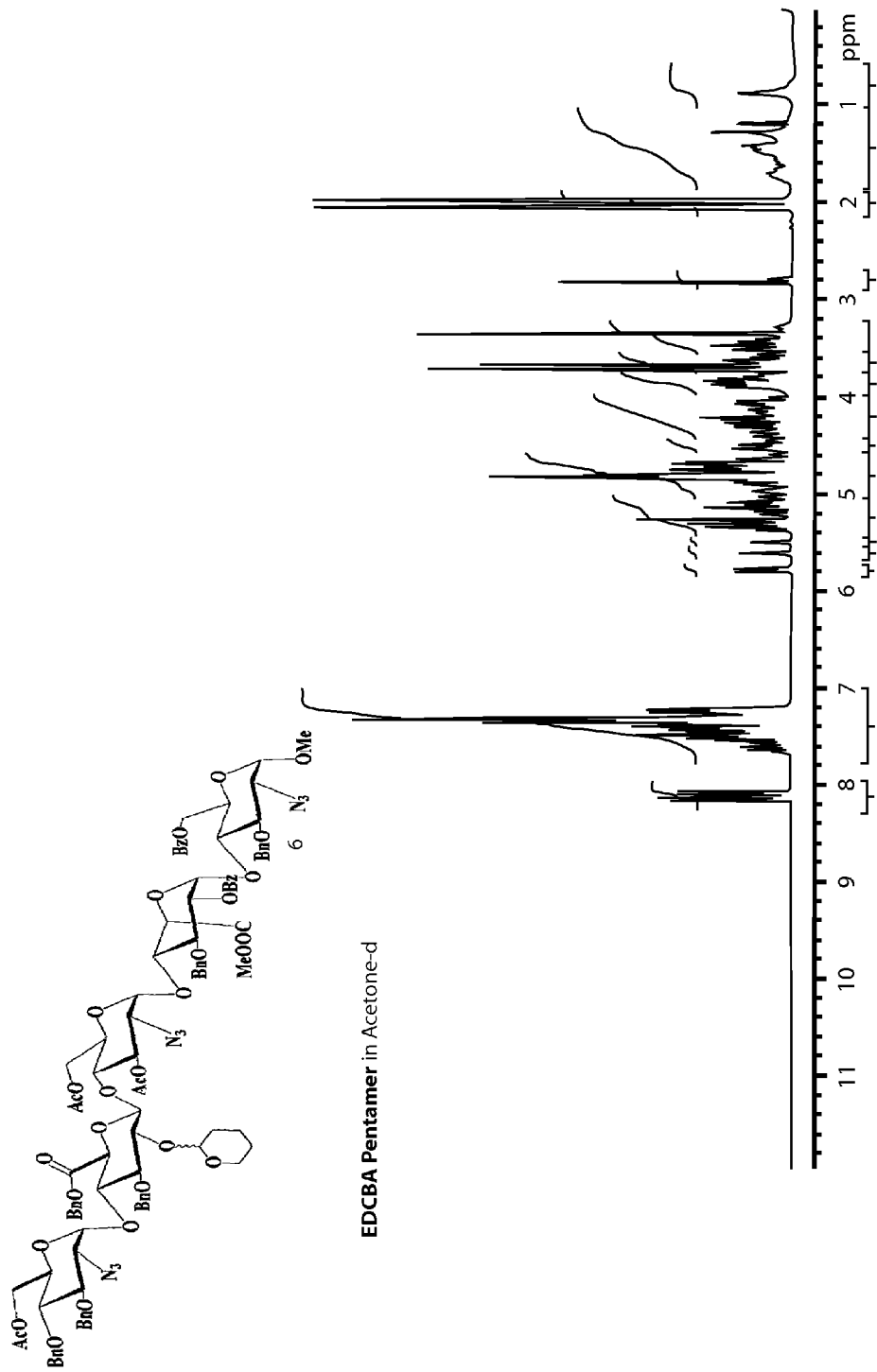
FIG. 9 is a $^1$H NMR spectrum of the EDCBA pentamer.

Methyl O-6-O-acetyl-2-azido-2-deoxy-3,4-di-O-benzyl-α-D-glucopyranosyl-(1→4)-O-[benzyl 3-O-benzyl-2-O-tetrahydropyranyl-β-D-glucopyranosyluronate]-(1→4)-O-2-azido-2-deoxy-3,6-di-O-acetyl-α-D-glucopyranosyl-(1→4)-O-[methyl 2-O-benzoyl-3-O-benzyl-α-L-Idopyranosyluronate]-(1→4)-2-azido-6-O-benzoyl-3-O-benzyl-2-deoxy-α-D-glucopyranoside 2.47 Kg (1.35 mol) of EDCBA2 was dissolved in 23 L Dichloroethane and chilled to 10-15° C., after which 1.13 Kg (13.5 mol, 10 eq) of Dihydropyran and 31.3 g (0.135 mol, 0.1 eq) of Camphorsulfonic acid were added. The reaction was allowed warm to 20-25° C. and stirred for 4-6 hours until reaction was complete. Water (15 L) was added and the reaction was extracted with an additional 10 L of DCE. The organic layer was extracted with a 25% 4:1 Sodium Chloride/Sodium Bicarbonate solution (2×20 L), dried over anhydrous sodium sulfate, and evaporated under vacuum to a syrup. Column chromatographic separation using silica gel and 10-35% ethyl acetate/heptane gradient yielded 2.28 Kg (88.5% yield) of fully protected EDCBA Pentamer. The $^1$H NMR spectrum (d6-acetone) of the EDCBA pentamer is shown in FIG. 9.

Preparation of API1

Step 1: Saponification

Methyl O-2-azido-2-deoxy-3,4-di-O-benzyl-α-D-glucopyranosyl-(1→4)-O-3-O-benzyl-2-O-tetrahydropyranyl-β-D-glucopyranosyluronosyl-(1→4)-O-2-azido-2-deoxy-α-D-glucopyranosyl-(1→4)-O-3-O-benzyl-α-L-Idopyranosyluronosyl-(1→4) 2-azido-3-O-benzyl-2-deoxy-α-D-glucopyranoside disodium salt To a solution of 2.28 Kg (1.19 mol) of EDCBA Pentamer in 27 L of Dioxane and 41 L of Tetrahydrofuran was added 45.5 L of 0.7 M (31.88 mol, 27 eq) Lithium hydroxide solution followed by 5.33 L of 30% Hydrogen peroxide. The reaction mixture was stirred for 10-20 hours to remove the acetyl groups. Then, 10 L of 4 N (40 mol, 34 eq) sodium hydroxide solution was added. The reaction was allowed to stir for an additional 24-48 hours to hydrolyze the benzyl and methyl esters completely. The reaction was then extracted with ethyl acetate. The organic layer was extracted with brine solution and dried with anhydrous sodium sulfate. Evaporation of the solvent under vacuum gave a syrup of API1 [also referred to as EDCBA(OH)$_5$] which was used for the next step without further purification.

Preparation of API2

Step 2: O-Sulfonation

Figure 10:
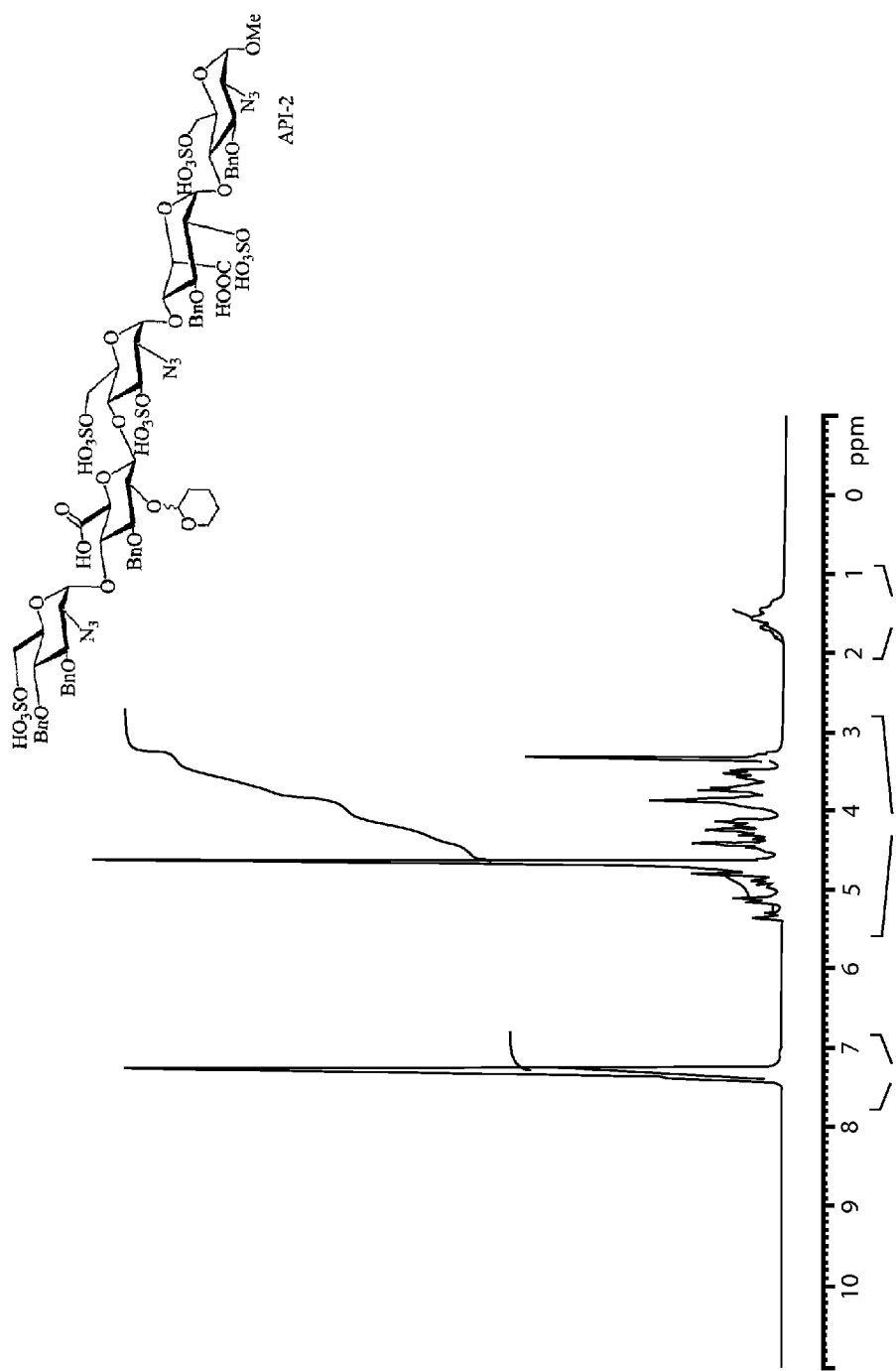
FIG. 10 is a $^1$H NMR spectrum of API-2 pentamer.

Methyl O-2-azido-2-deoxy-3,4-di-O-benzyl-6-O-sulfo-α-D-glucopyranosyl-(1→4)-O-3-O-benzyl-2-O-tetrahydropyranyl-β-D-glucopyranosyluronosyl-(1→4)-O-2-azido-2-deoxy-3,6-di-O-sulfo-α-D-glucopyranosyl-(1→4)-O-3-O-benzyl-2-O-sulfo-α-L-idopyranuronosyl-(1→4)-2-azido-2-deoxy-6-O-sulfo-α-D-glucopyranoside, heptasodium salt The crude product of API1 [aka EDCBA(OH)$_5$] obtained in step 1 was dissolved in 10 L Dimethylformamide. To this was added a previously prepared solution containing 10.5 Kg (66 moles) of sulfur trioxide-pyridine complex in 10 L of Pyridine and 25 L of Dimethylformamide. The reaction mixture was heated to 50° C. over a period of 45 min After stiffing at 1.5 hours at 50° C., the reaction was cooled to 20° C. and was quenched into 60 L of 8% sodium bicarbonate solution that was kept at 10° C. The pH of the quench mixture was maintained at pH 7-9 by addition of sodium bicarbonate solution. When all the reaction mixture has been transferred, the quench mixture was stirred for an additional 2 hours and pH was maintained at pH 7 or greater. When the pH of quench has stabilized, it was diluted with water and the resulting mixture was purified using a preparative HPLC column packed with Amberchrom CG161-M and eluted with 90%-10% Sodium Bicarbonate (5%) solution/Methanol over 180 min. The pure fractions were concentrated under vacuum and was then desalted using a size exclusion resin or gel filtration (Biorad) G25 to give 1581 g (65.5% yield over 2 steps) of API2 [also referred to as EDCBA(OSO$_3$)$_5$]. The $^1$H NMR spectrum (d6-acetone) of API-2 pentamer is shown in FIG. 10.

Preparation of API3

Step 3: Hydrogenation

Figure 11:
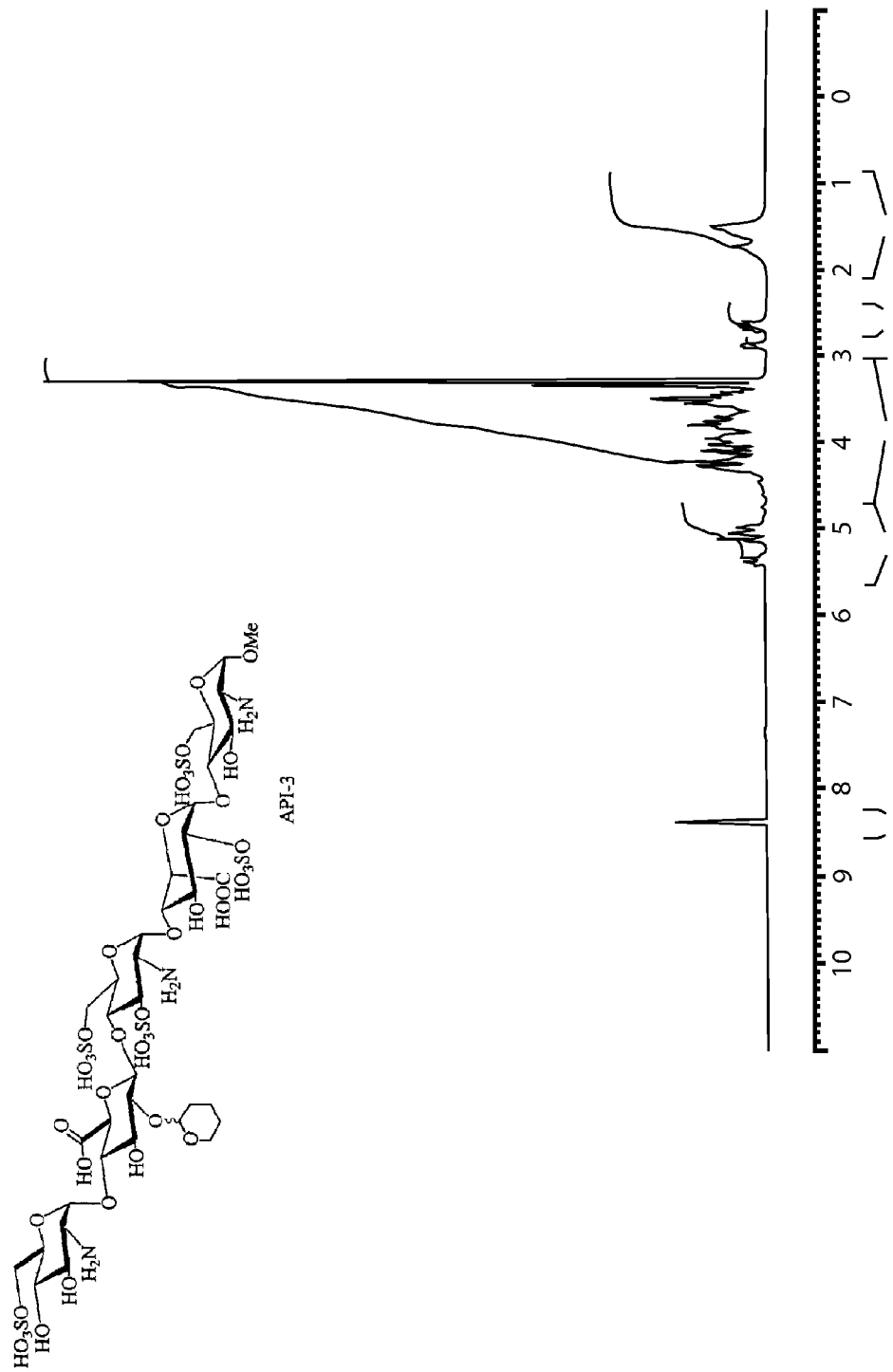
FIG. 11 is a $^1$H NMR spectrum of API-3 pentamer.

Methyl O-2-amino-2-deoxy-6-O-sulfo-α-D-glucopyranosyl-(1→4)-O-2-O-tetrahydropyranyl-β-D-glucopyranosyluronosyl-(1→4)-O-2-amino-2-deoxy-3,6-di-O-sulfo-α-D-glucopyranosyl-(1→4)-O-2-O-sulfo-α-L-idopyranuronosyl-(1→4)-2-amino-2-deoxy-6-O-sulfo-α-D-glucopyranoside, heptasodium salt A solution of 1581 g (0.78 mol) of O-Sulfated pentasaccharide API2 in 38 L of Methanol and 32 L of water was treated with 30 wt % of Palladium in Activated carbon under 100 psi of Hydrogen pressure at 60-65° C. for 60 hours or until completion of reaction. The mixture was then filtered through 1.0µ and 0.2µ filter cartridges and the solvent evaporated under vacuum to give 942 g (80% yield) of API3 [also referred to as EDCBA(OSO$_3$)$_5$(NH$_2$)$_3$]. The $^1$H NMR spectrum (d6-acetone) of API-3 pentamer is shown in FIG. 11.

Preparation of Fondaparinux Sodium

Step 4: N-Sulfation & Removal of THP

Methyl O-2-deoxy-6-O-sulfo-2-(sulfoamino)-α-D-glucopyranosyl-(1→4)-O-β-D-glucopyranuronosyl-(1→4)-O-2-deoxy-3,6-di-O-sulfo-2-(sulfoamino)-α-D-glucopyranosyl-(1→4)-O-2-O-sulfo-α-L-idopyranuronosyl-(1→4)-2-deoxy-6-O-sulfo-2-(sulfoamino)-α-D-glucopyranoside, decasodium salt To a solution of 942 g (0.63 mol) of API3 in 46 L of water was slowly added 3.25 Kg (20.4 mol, 32 eq) of Sulfur trioxide-pyridine complex, maintaining the pH of the reaction mixture at pH 9-9.5 during the addition using 2 N sodium hydroxide solution. The reaction was allowed to stir for 4-6 hours at pH 9.0-9.5. When reaction was complete, the pH was adjusted to pH 7.0 using 50 mM solution of Ammonium acetate at pH 3.5. The resulting N-sulfated EDCBA(OSO$_3$)$_5$ (NHSO$_3$)$_3$ mixture was purified using Ion-Exchange Chromatographic Column (Varian Preparative 15 cm HiQ Column) followed by desalting using a size exclusion resin or gel filtration (Biorad G25). The resulting mixture was then treated with activated charcoal and the purification by ion-exchange and desalting were repeated to give 516 g (47.6% yield) of the purified Fondaparinux Sodium form.

Analysis of the Fondaparinux sodium identified the presence of P1, P2, P3, and P4 in the fondaparinux. P1, P2, P3, and P4 were identified by standard analytical methods.

We claim:
1. A process for making a compound of Formula I

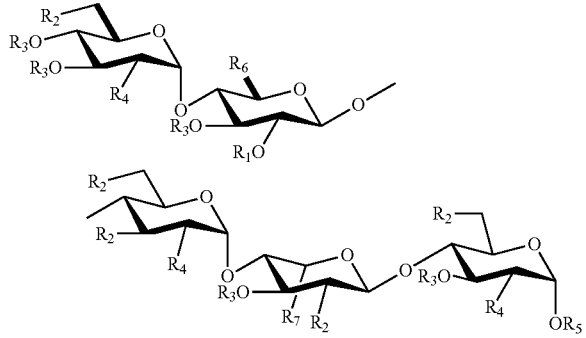

Formula I

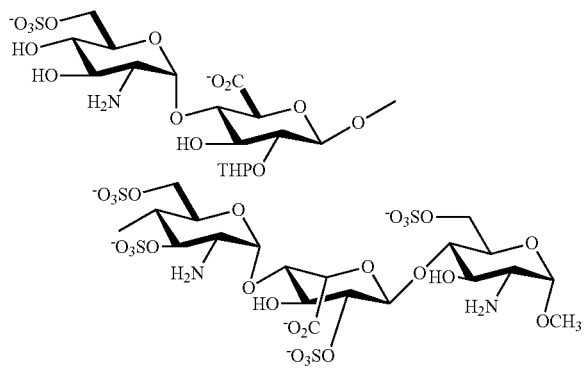

wherein R$_1$ is tetrahydropyran (THP), R$_2$ is —OSO$_3$ Na, R$_3$ is H, R$_4$ is NHSO$_3$ Na, R$_5$ is methyl, and R$_6$ and R$_7$ are —CO$_2$ Na, the process comprising the step of sulfating a compound of or a salt thereof.

2. A process for making a compound of Formula I:

Formula I

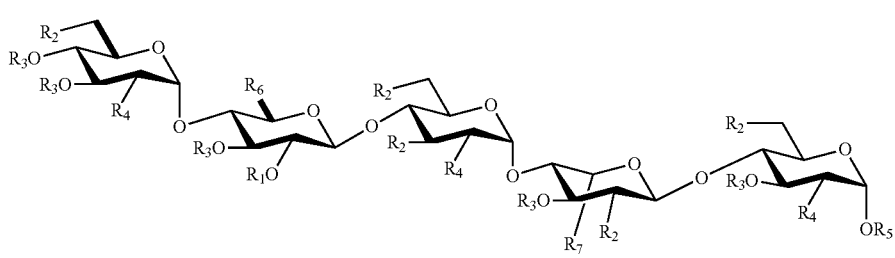

wherein $R_1$ is H, $R_2$ is —$OSO_3$ Na, $R_3$ is H, $R_4$ is $NHSO_3$ Na, $R_5$ is methyl, and $R_6$ and $R_7$ are —$CO_2$ Na;
the process comprising deprotecting a compound of the formula:
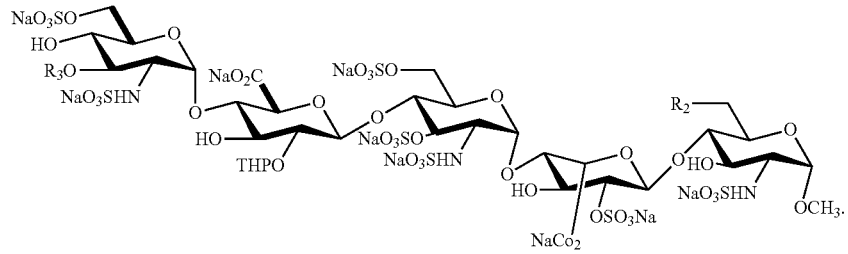
3. A process for making a compound of Formula 8:
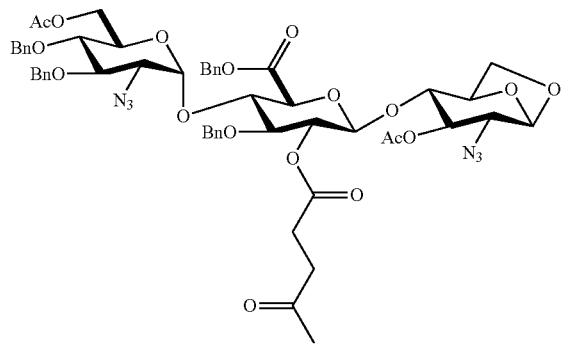
Formula 8
comprising reacting a compound of Formula 9:
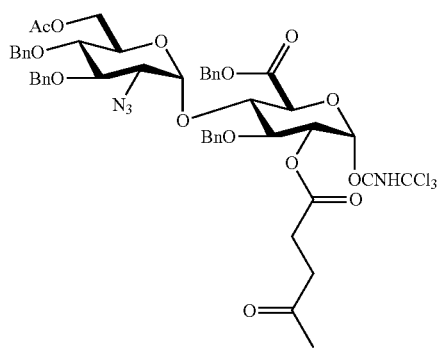
Formula 9
with a compound of Formula 10:
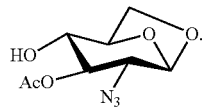
Formula 10
* * * * *